US009878023B1

(12) United States Patent
Bermudes

(10) Patent No.: US 9,878,023 B1
(45) Date of Patent: *Jan. 30, 2018

(54) PROTEASE INHIBITOR: PROTEASE SENSITIVE EXPRESSION SYSTEM COMPOSITION AND METHODS IMPROVING THE THERAPEUTIC ACTIVITY AND SPECIFICITY OF PROTEINS DELIVERED BY BACTERIA

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/754,113

(22) Filed: Jun. 29, 2015

Related U.S. Application Data

(62) Division of application No. 14/016,407, filed on Sep. 3, 2013, now Pat. No. 9,068,187, which is a division of application No. 13/024,172, filed on Feb. 9, 2011, now Pat. No. 8,524,220.

(60) Provisional application No. 61/302,938, filed on Feb. 9, 2010.

(51) Int. Cl.
*A61K 48/00* (2006.01)
*A61K 38/48* (2006.01)
*A01N 63/02* (2006.01)
*A61K 38/55* (2006.01)
*C12N 9/22* (2006.01)
*A61K 38/16* (2006.01)

(52) U.S. Cl.
CPC ............ *A61K 38/55* (2013.01); *A61K 38/164* (2013.01); *C12N 9/22* (2013.01)

(58) Field of Classification Search
None
See application file for complete search history.

(56) References Cited

U.S. PATENT DOCUMENTS

| | | | |
|---|---|---|---|
| 4,436,727 A | 3/1984 | Ribi |
| 4,906,567 A | 3/1990 | Connelly |
| 5,021,234 A | 6/1991 | Ehrenfeld |
| D320,325 S | 10/1991 | Barfield |
| 5,087,569 A | 2/1992 | Gabay et al. |
| 5,126,257 A | 6/1992 | Gabay et al. |
| 5,143,830 A | 9/1992 | Holland et al. |
| 5,223,409 A | 6/1993 | Ladner et al. |
| 5,278,049 A | 1/1994 | Baker et al. |
| 5,281,530 A | 1/1994 | Sick et al. |
| 5,318,900 A | 6/1994 | Habuka et al. |
| 5,338,724 A | 8/1994 | Gabay et al. |
| 5,344,762 A | 9/1994 | Karapetian |
| 5,354,675 A | 10/1994 | Iida et al. |
| 5,399,490 A | 3/1995 | Balganesh et al. |
| 5,403,484 A | 4/1995 | Ladner et al. |
| 5,466,463 A | 11/1995 | Ford |
| 5,466,672 A | 11/1995 | Kushnaryov et al. |
| 5,495,001 A | 2/1996 | McGrogan et al. |
| 5,506,139 A | 4/1996 | Loosmore et al. |
| 5,569,597 A | 10/1996 | Grimsley et al. |
| 5,571,698 A | 11/1996 | Ladner et al. |
| 5,604,201 A | 2/1997 | Thomas et al. |
| 5,651,965 A | 7/1997 | Payne |
| 5,656,436 A | 8/1997 | Loosmore et al. |
| 5,665,353 A | 9/1997 | Loosmore et al. |
| 5,705,151 A | 1/1998 | Dow et al. |
| 5,712,369 A | 1/1998 | Old et al. |
| 5,824,538 A | 10/1998 | Branstrom et al. |
| 5,830,702 A | 11/1998 | Portnoy et al. |
| 5,837,500 A | 11/1998 | Ladner et al. |

(Continued)

FOREIGN PATENT DOCUMENTS

| | | |
|---|---|---|
| EP | 0973911 | 1/2000 |
| EP | 1513924 | 3/2005 |

(Continued)

OTHER PUBLICATIONS

Callaway, E; www.newscientist.com, 2008 "Counting in a Bacterial World".*
Soghomonyan, Surren A., et al. "Positron emission tomography (PET) imaging of tumor-localized *Salmonella* expressing HSV1-TK." Cancer gene therapy 12.1 (2005): 101-108.
Honée, Guy, Wim Vriezen, and Bert Visser. "A translation fusion product of two different insecticidal crystal protein genes of Bacillus thuringiensis exhibits an enlarged insecticidal spectrum." Applied and environmental microbiology 56.3 (1990): 823-825.
Gumbmann, M. R., et al. "The USDA trypsin inhibitor study. IV. The chronic effects of soy flour and soy protein isolate on the pancreas in rats after two years." Plant Foods for Human Nutrition 35.3 (1985): 275-314.
Bacillus thuringiensis, Wikipedia, Mar. 21, 2016.

(Continued)

*Primary Examiner* — James D Schultz
(74) *Attorney, Agent, or Firm* — Steven M. Hoffberg; Tully Rinckey PLLC

(57) ABSTRACT

Bacteria which co-express protease inhibitors and protease sensitive therapeutic agents, which are surface displayed, secreted and/or released and result in their localized production and maintenance within a target tissue and inactivation outside of the target tissue, thereby increasing therapeutic activity and reducing the systemic toxicity. The bacteria may be attenuated, non-pathogenic, low pathogenic or a probiotic. Protease sensitivity may be further accomplished by engineering protease degradation sites within the therapeutic agents, further enhancing the inactivation outside of the target tissue while retaining activity within the target tissue through co-expression of a protease inhibitor. Novel chimeric proteins secreted by bacteria, including chimeric toxins targeted to neoplastic cells, tumor matrix cells and cells of the immune system, and combination therapies of these protease inhibitor:chimeric toxin-expressing bacteria together with small-molecule and biologic agents are also described. Non-conjugative bacteria limiting exchange of genetic material, and antibody resistant bacteria are also provided.

19 Claims, 11 Drawing Sheets

(56) References Cited

U.S. PATENT DOCUMENTS

| | | |
|---|---|---|
| 5,869,302 A | 2/1999 | Loosmore et al. |
| 5,877,159 A | 3/1999 | Powell et al. |
| 5,935,573 A | 8/1999 | Loosmore et al. |
| 5,939,297 A | 8/1999 | Loosmore et al. |
| 5,945,102 A | 8/1999 | de Faire et al. |
| 5,958,406 A | 9/1999 | de Faire et al. |
| 5,962,430 A | 10/1999 | Loosmore et al. |
| 5,981,503 A | 11/1999 | Loosmore et al. |
| 5,997,881 A | 12/1999 | Powell et al. |
| 6,004,562 A | 12/1999 | Campagnari |
| 6,020,183 A | 2/2000 | Loosmore et al. |
| 6,022,855 A | 2/2000 | Thomas et al. |
| 6,025,342 A | 2/2000 | Loosmore et al. |
| 6,030,612 A | 2/2000 | de Faire et al. |
| 6,030,780 A | 2/2000 | Vinkemeier et al. |
| 6,037,526 A | 3/2000 | Grimsley et al. |
| 6,051,237 A | 4/2000 | Paterson |
| 6,080,849 A | 6/2000 | Bermudes et al. |
| 6,114,125 A | 9/2000 | Loosmore et al. |
| 6,143,551 A | 11/2000 | Goebel |
| 6,147,057 A | 11/2000 | Loosmore et al. |
| 6,150,170 A | 11/2000 | Powell et al. |
| 6,153,580 A | 11/2000 | Loosmore et al. |
| 6,177,083 B1 | 1/2001 | Lubitz |
| 6,190,657 B1 | 2/2001 | Pawelek et al. |
| 6,207,156 B1 | 3/2001 | Kuchroo et al. |
| 6,232,110 B1 | 5/2001 | Pallas et al. |
| 6,245,892 B1 | 6/2001 | Oaks et al. |
| 6,251,406 B1 | 6/2001 | Haefliger et al. |
| 6,277,379 B1 | 8/2001 | Oaks et al. |
| 6,348,344 B1 | 2/2002 | Ayal-Hershkovitz et al. |
| 6,355,790 B1 | 3/2002 | Rosenblatt et al. |
| 6,376,234 B1 | 4/2002 | Grimsley et al. |
| 6,410,012 B1 | 6/2002 | Sizemore et al. |
| 6,447,777 B1 | 9/2002 | Terman et al. |
| 6,447,784 B1 | 9/2002 | Bermudes et al. |
| 6,475,482 B1 | 11/2002 | Bermudes et al. |
| 6,475,763 B1 | 11/2002 | Ayal-Hershkovitz et al. |
| 6,537,558 B2 | 3/2003 | Kaniga |
| 6,548,287 B1 | 4/2003 | Powell et al. |
| 6,605,286 B2 | 8/2003 | Steidler et al. |
| 6,605,697 B1 | 8/2003 | Kwon et al. |
| 6,638,912 B2 | 10/2003 | Bhatnagar et al. |
| 6,680,374 B2 | 1/2004 | Oaks et al. |
| 6,685,935 B1 | 2/2004 | Pawelek et al. |
| 6,743,893 B2 | 6/2004 | Engler et al. |
| 6,746,671 B2 | 6/2004 | Steidler et al. |
| 6,841,535 B2 | 1/2005 | Divita et al. |
| 6,863,894 B2 | 3/2005 | Bermudes et al. |
| 6,923,972 B2 | 8/2005 | Bermudes et al. |
| 6,962,696 B1 | 11/2005 | Bermudes et al. |
| 6,979,538 B2 | 12/2005 | Ladner et al. |
| 7,001,884 B2 | 2/2006 | Komiyama et al. |
| 7,033,991 B2 | 4/2006 | Lindberg et al. |
| 7,118,879 B2 | 10/2006 | Ladner et al. |
| 7,208,293 B2 | 4/2007 | Ladner et al. |
| 7,258,863 B2 | 8/2007 | Oaks et al. |
| 7,354,592 B2 | 4/2008 | Bermudes et al. |
| 7,358,084 B2 | 4/2008 | Kolkman |
| 7,390,646 B2 | 6/2008 | Andino-Pavlovsky et al. |
| 7,413,877 B2 | 8/2008 | Collier et al. |
| 7,452,531 B2 | 11/2008 | Bermudes et al. |
| 7,514,089 B2 | 4/2009 | Bermudes et al. |
| 7,569,547 B2 | 8/2009 | Lindberg et al. |
| 7,635,682 B2 | 12/2009 | Denmeade et al. |
| 7,666,627 B2 | 2/2010 | Gal et al. |
| 7,691,599 B2 | 4/2010 | Rubin |
| 7,696,173 B2 | 4/2010 | Collier et al. |
| 7,700,349 B2 | 4/2010 | Romaine et al. |
| 7,700,830 B2 | 4/2010 | Corbin et al. |
| 7,705,195 B2 | 4/2010 | French et al. |
| 7,718,618 B2 | 5/2010 | Gallo et al. |
| 7,776,823 B2 | 8/2010 | Gallo et al. |
| 7,803,918 B2 | 9/2010 | van der Hoek |
| 7,846,678 B2 | 12/2010 | Pepe et al. |
| 7,850,970 B2 | 12/2010 | Shapiro |
| 7,887,794 B2 | 2/2011 | Luquet et al. |
| 7,888,321 B2 | 2/2011 | Cooper et al. |
| 7,892,803 B2 | 2/2011 | Tanner et al. |
| 7,892,825 B2 | 2/2011 | Barr et al. |
| 7,893,007 B2 | 2/2011 | Ladner et al. |
| 7,943,754 B2 | 5/2011 | Bentwich et al. |
| 7,947,822 B2 | 5/2011 | Nabel et al. |
| 7,964,362 B2 | 6/2011 | Lee et al. |
| 7,989,202 B1 | 8/2011 | Mach et al. |
| 8,030,447 B2 | 10/2011 | Motin et al. |
| 8,030,542 B2 | 10/2011 | Corbin et al. |
| 8,062,885 B2 | 11/2011 | Mach et al. |
| 8,101,349 B2 | 1/2012 | Garcia et al. |
| 8,101,826 B2 | 1/2012 | Romano |
| 8,119,354 B2 | 2/2012 | Katanaev |
| 8,128,922 B2 | 3/2012 | Wu et al. |
| 8,153,414 B2 | 4/2012 | Caplan et al. |
| 8,173,397 B2 | 5/2012 | Gal et al. |
| 8,206,700 B2 | 6/2012 | Horwitz et al. |
| 8,231,878 B2 | 7/2012 | Colonna et al. |
| 8,236,315 B2 | 8/2012 | Lazarides et al. |
| 8,241,623 B1 | 8/2012 | Bermudes |
| 8,244,484 B2 | 8/2012 | Lee et al. |
| 8,246,945 B2 | 8/2012 | Caplan et al. |
| 8,283,319 B2 | 10/2012 | Schulte et al. |
| 8,323,961 B2 | 12/2012 | Nabel et al. |
| 8,349,570 B2 | 1/2013 | Pepe et al. |
| 8,372,620 B2 | 2/2013 | Sibbesen et al. |
| 8,440,207 B2 | 5/2013 | Bermudes |
| 8,445,650 B2 | 5/2013 | Simpson et al. |
| 8,507,249 B2 | 8/2013 | Finlay et al. |
| 8,524,220 B1 | 9/2013 | Bermudes |
| 8,603,824 B2 | 12/2013 | Ramseier et al. |
| 8,609,358 B2 | 12/2013 | Sebastian et al. |
| 8,623,350 B1 | 1/2014 | Bermudes |
| 8,628,782 B2 | 1/2014 | Berkower |
| 8,633,305 B2 | 1/2014 | Shapiro |
| 8,647,642 B2 | 2/2014 | Bermudes |
| 8,685,392 B2 | 4/2014 | Helmerhorst et al. |
| 8,686,218 B2 | 4/2014 | Romaine et al. |
| 8,741,313 B2 | 6/2014 | Sable et al. |
| 8,748,373 B2 | 6/2014 | Chai et al. |
| 8,758,771 B2 | 6/2014 | Finlay et al. |
| 8,759,086 B2 | 6/2014 | Mach et al. |
| 8,771,669 B1 | 7/2014 | Bermudes |
| 8,771,671 B2 | 7/2014 | Spencer et al. |
| 8,791,237 B2 | 7/2014 | Paterson et al. |
| 8,795,730 B2 | 8/2014 | Vachon |
| 8,815,251 B2 | 8/2014 | Caplan et al. |
| 8,821,893 B2 | 9/2014 | Dattwyler et al. |
| 8,835,107 B2 | 9/2014 | Van Der Hoek |
| 8,853,362 B2 | 10/2014 | Tissot et al. |
| 8,906,662 B2 | 12/2014 | Nataro et al. |
| 8,920,809 B2 | 12/2014 | Dirienzo |
| 8,926,993 B2 | 1/2015 | Dubensky, Jr. et al. |
| 8,951,992 B2 | 2/2015 | Nathan et al. |
| 8,956,859 B1 | 2/2015 | Bermudes |
| 8,962,816 B2 | 2/2015 | Ertl et al. |
| 8,969,542 B2 | 3/2015 | Buyse et al. |
| 8,981,061 B2 | 3/2015 | Colonna et al. |
| 8,999,949 B2 | 4/2015 | Spencer et al. |
| 9,068,187 B1 | 6/2015 | Bermudes |
| 9,109,229 B2 | 8/2015 | Ramseier et al. |
| 9,161,974 B2 | 10/2015 | Dubensky et al. |
| 9,187,523 B2 | 11/2015 | Motin et al. |
| 9,187,762 B2 | 11/2015 | Albert et al. |
| 9,198,960 B2 | 12/2015 | Dubensky, Jr. et al. |
| 9,200,251 B1 | 12/2015 | Bermudes |
| 9,200,289 B1 | 12/2015 | Bermudes |
| 9,206,456 B2 | 12/2015 | Lenormand |
| 9,486,513 B1* | 11/2016 | Bermudes .............. A61K 35/74 |
| 2001/0006642 A1 | 7/2001 | Steidler et al. |
| 2001/0009957 A1 | 7/2001 | Oaks et al. |
| 2001/0029024 A1 | 10/2001 | Kodadek |
| 2001/0029043 A1 | 10/2001 | Haefliger et al. |
| 2002/0016982 A1 | 2/2002 | Romaine et al. |
| 2002/0026655 A1 | 2/2002 | Bermudes et al. |
| 2002/0106380 A1 | 8/2002 | Hung et al. |

(56) References Cited

U.S. PATENT DOCUMENTS

| | | |
|---|---|---|
| 2002/0107374 A1 | 8/2002 | Pallas et al. |
| 2002/0123053 A1 | 9/2002 | Luo et al. |
| 2002/0150881 A1 | 10/2002 | Ladner et al. |
| 2002/0197276 A1 | 12/2002 | Oaks et al. |
| 2003/0059400 A1 | 3/2003 | Szalay |
| 2003/0082219 A1 | 5/2003 | Warren et al. |
| 2003/0087827 A1 | 5/2003 | Lindberg et al. |
| 2003/0092066 A1 | 5/2003 | Vinkemeier et al. |
| 2003/0106096 A1 | 6/2003 | Barry |
| 2003/0109026 A1 | 6/2003 | Bermudes et al. |
| 2003/0113293 A1 | 6/2003 | Bermudes et al. |
| 2003/0113717 A1 | 6/2003 | Ladner et al. |
| 2003/0115630 A1 | 6/2003 | Romano |
| 2003/0124561 A1 | 7/2003 | Mach et al. |
| 2003/0131372 A1 | 7/2003 | Copenhaver et al. |
| 2003/0131376 A1 | 7/2003 | Okubara et al. |
| 2003/0144490 A1 | 7/2003 | Edwards et al. |
| 2003/0165875 A1 | 9/2003 | Colonna et al. |
| 2003/0166140 A1 | 9/2003 | Chen et al. |
| 2003/0170276 A1 | 9/2003 | Bermudes et al. |
| 2003/0186416 A1 | 10/2003 | Pallas et al. |
| 2003/0188336 A1 | 10/2003 | Corbin et al. |
| 2003/0203377 A1 | 10/2003 | Milne Edwards et al. |
| 2003/0211476 A1 | 11/2003 | O'Mahony et al. |
| 2003/0219722 A1 | 11/2003 | Ladner et al. |
| 2003/0219886 A1 | 11/2003 | Ladner et al. |
| 2004/0005539 A1 | 1/2004 | Ladner et al. |
| 2004/0013658 A1 | 1/2004 | Fulton et al. |
| 2004/0023205 A1 | 2/2004 | Ladner et al. |
| 2004/0023282 A1 | 2/2004 | Luo et al. |
| 2004/0038307 A1 | 2/2004 | Lee et al. |
| 2004/0096426 A1 | 5/2004 | Chen et al. |
| 2004/0101531 A1 | 5/2004 | Curtiss et al. |
| 2004/0110939 A1 | 6/2004 | Dumas Milne Edwards et al. |
| 2004/0115788 A1 | 6/2004 | Zheng et al. |
| 2004/0133930 A1 | 7/2004 | Cooper et al. |
| 2004/0180380 A1 | 9/2004 | Lee et al. |
| 2004/0191787 A1 | 9/2004 | Tanner et al. |
| 2004/0219169 A1 | 11/2004 | Bermudes et al. |
| 2004/0229338 A1 | 11/2004 | King |
| 2004/0234956 A1 | 11/2004 | Kabat et al. |
| 2004/0234998 A1 | 11/2004 | Sibbesen et al. |
| 2004/0266674 A1 | 12/2004 | Mills et al. |
| 2005/0013822 A1 | 1/2005 | Oaks et al. |
| 2005/0032157 A1 | 2/2005 | Gal et al. |
| 2005/0036987 A1 | 2/2005 | Pawelek et al. |
| 2005/0055746 A1 | 3/2005 | Michaud et al. |
| 2005/0063994 A1 | 3/2005 | Caplan et al. |
| 2005/0069532 A1 | 3/2005 | Weinrauch et al. |
| 2005/0069911 A1 | 3/2005 | Lee et al. |
| 2005/0070007 A1 | 3/2005 | Romaine et al. |
| 2005/0074463 A1 | 4/2005 | Autran et al. |
| 2005/0079573 A1 | 4/2005 | Sibbesen |
| 2005/0084972 A1 | 4/2005 | Barr et al. |
| 2005/0106151 A1 | 5/2005 | Shapiro |
| 2005/0112139 A1 | 5/2005 | Karp |
| 2005/0118193 A1 | 6/2005 | Andino-Pavlovsky et al. |
| 2005/0148504 A1 | 7/2005 | Katunuma et al. |
| 2005/0158295 A1 | 7/2005 | Swiercz et al. |
| 2005/0166274 A1 | 7/2005 | French et al. |
| 2005/0180963 A1 | 8/2005 | Adams et al. |
| 2005/0202535 A1 | 9/2005 | Collier et al. |
| 2005/0203007 A1 | 9/2005 | Komiyama et al. |
| 2005/0208033 A1 | 9/2005 | Luquet et al. |
| 2005/0227917 A1 | 10/2005 | Williams et al. |
| 2005/0241015 A1 | 10/2005 | Mach et al. |
| 2005/0241016 A1 | 10/2005 | Mach et al. |
| 2005/0249706 A1 | 11/2005 | Bermudes et al. |
| 2005/0251885 A1 | 11/2005 | Michaud et al. |
| 2005/0255088 A1 | 11/2005 | Bermudes et al. |
| 2005/0257282 A1 | 11/2005 | Mach et al. |
| 2005/0260670 A1 | 11/2005 | Colonna et al. |
| 2005/0266560 A1 | 12/2005 | Preuss et al. |
| 2005/0268359 A1 | 12/2005 | Mach et al. |
| 2005/0273882 A1 | 12/2005 | Romano |
| 2005/0281828 A1 | 12/2005 | Bowdish et al. |
| 2006/0009633 A9 | 1/2006 | Dimas et al. |
| 2006/0014212 A1 | 1/2006 | Benkovic et al. |
| 2006/0024668 A1 | 2/2006 | Hoek |
| 2006/0035270 A1 | 2/2006 | Lee et al. |
| 2006/0035320 A1 | 2/2006 | Tissot et al. |
| 2006/0035371 A1 | 2/2006 | Zheng et al. |
| 2006/0084113 A1 | 4/2006 | Ladner et al. |
| 2006/0088910 A1 | 4/2006 | Nguyen |
| 2006/0110747 A1 | 5/2006 | Ramseier et al. |
| 2006/0156440 A1 | 7/2006 | Michaud et al. |
| 2006/0160152 A1 | 7/2006 | Vinkemeier et al. |
| 2006/0174357 A1 | 8/2006 | Velander et al. |
| 2006/0182762 A1 | 8/2006 | Irene Martina Maas et al. |
| 2006/0223142 A1 | 10/2006 | Dumas Milne Edwards et al. |
| 2006/0229336 A1 | 10/2006 | Kazmierski et al. |
| 2006/0241050 A1 | 10/2006 | Cameron et al. |
| 2006/0269561 A1 | 11/2006 | Paterson et al. |
| 2006/0275823 A1 | 12/2006 | Kodadek |
| 2006/0275897 A1 | 12/2006 | Nabel et al. |
| 2006/0286639 A1 | 12/2006 | Dumas Milne Edwards et al. |
| 2007/0009489 A1 | 1/2007 | Bermudes et al. |
| 2007/0020327 A1 | 1/2007 | Fikes et al. |
| 2007/0028324 A1 | 2/2007 | Corbin et al. |
| 2007/0037744 A1 | 2/2007 | Gallo et al. |
| 2007/0041997 A1 | 2/2007 | Finlay et al. |
| 2007/0059799 A1 | 3/2007 | Sette et al. |
| 2007/0065908 A1 | 3/2007 | Gallo et al. |
| 2007/0071773 A1 | 3/2007 | Hanski et al. |
| 2007/0143871 A1 | 6/2007 | French et al. |
| 2007/0192905 A1 | 8/2007 | Piller et al. |
| 2007/0254329 A1 | 11/2007 | Rubin |
| 2007/0259417 A1 | 11/2007 | Ladner et al. |
| 2007/0275423 A1 | 11/2007 | Sebastian et al. |
| 2007/0298012 A1 | 12/2007 | King et al. |
| 2008/0019994 A1 | 1/2008 | Brunham et al. |
| 2008/0038296 A1 | 2/2008 | Brahmbhatt et al. |
| 2008/0070255 A1 | 3/2008 | Tanner et al. |
| 2008/0089862 A1 | 4/2008 | Benhar et al. |
| 2008/0090770 A1 | 4/2008 | Belmares et al. |
| 2008/0124355 A1 | 5/2008 | Bermudes |
| 2008/0181892 A1 | 7/2008 | Ledbetter et al. |
| 2008/0261869 A1 | 10/2008 | Shapiro |
| 2008/0269070 A1 | 10/2008 | Ramseier et al. |
| 2008/0286306 A1 | 11/2008 | Nabel et al. |
| 2008/0288264 A1 | 11/2008 | Mach et al. |
| 2008/0311081 A1 | 12/2008 | Fruehauf et al. |
| 2009/0011974 A1 | 1/2009 | Bocharov et al. |
| 2009/0019609 A1 | 1/2009 | Romano |
| 2009/0023157 A1 | 1/2009 | Lee et al. |
| 2009/0042248 A1 | 2/2009 | Gal et al. |
| 2009/0042278 A1 | 2/2009 | Barr et al. |
| 2009/0069248 A1 | 3/2009 | Motin et al. |
| 2009/0081199 A1 | 3/2009 | Colonna et al. |
| 2009/0111160 A1 | 4/2009 | Collier et al. |
| 2009/0123426 A1 | 5/2009 | Li et al. |
| 2009/0162356 A1 | 6/2009 | Lookeren Campagne |
| 2009/0169517 A1 | 7/2009 | Bermudes et al. |
| 2009/0169566 A1 | 7/2009 | Rawlin et al. |
| 2009/0209749 A1 | 8/2009 | Mach et al. |
| 2009/0214506 A1 | 8/2009 | Hardy et al. |
| 2009/0217396 A1 | 8/2009 | Kyrkanides et al. |
| 2009/0232804 A1 | 9/2009 | Lazarides et al. |
| 2009/0234101 A1 | 9/2009 | Ladner et al. |
| 2009/0239797 A1 | 9/2009 | Cooper et al. |
| 2009/0240073 A1 | 9/2009 | Barry |
| 2009/0246220 A1 | 10/2009 | Ertl et al. |
| 2009/0258935 A1 | 10/2009 | Zheng et al. |
| 2009/0294288 A1 | 12/2009 | May et al. |
| 2009/0297560 A1 | 12/2009 | Dattwyler et al. |
| 2009/0305296 A1 | 12/2009 | Bengtsson et al. |
| 2009/0317418 A1 | 12/2009 | Catanzaro et al. |
| 2010/0022584 A1 | 1/2010 | Kenyon et al. |
| 2010/0086546 A1 | 4/2010 | Lee et al. |
| 2010/0111998 A1 | 5/2010 | Nabel et al. |
| 2010/0135961 A1 | 6/2010 | Bermudes |
| 2010/0136048 A1 | 6/2010 | Bermudes |
| 2010/0137162 A1 | 6/2010 | Retallack et al. |
| 2010/0137192 A1 | 6/2010 | Shapiro |

(56) References Cited

U.S. PATENT DOCUMENTS

| | | |
|---|---|---|
| 2010/0166802 A1 | 7/2010 | Caplan et al. |
| 2010/0169988 A1 | 7/2010 | Kohli et al. |
| 2010/0184613 A1 | 7/2010 | Lee et al. |
| 2010/0189774 A1 | 7/2010 | Lenormand |
| 2010/0215679 A1 | 8/2010 | Horwitz et al. |
| 2010/0215682 A1 | 8/2010 | Berkower |
| 2010/0239546 A1 | 9/2010 | Fruehauf et al. |
| 2010/0247544 A1 | 9/2010 | Vachon |
| 2010/0247560 A1 | 9/2010 | Simpson et al. |
| 2010/0261201 A1 | 10/2010 | Katanaev |
| 2010/0272750 A1 | 10/2010 | Buyse et al. |
| 2010/0278819 A1 | 11/2010 | Bossuyt et al. |
| 2010/0279923 A1 | 11/2010 | Schulte et al. |
| 2010/0286251 A1 | 11/2010 | Rubin |
| 2010/0305306 A1 | 12/2010 | Colonna et al. |
| 2010/0310560 A1 | 12/2010 | Colonna et al. |
| 2010/0319087 A1 | 12/2010 | Corbin et al. |
| 2010/0333235 A1 | 12/2010 | Mach et al. |
| 2011/0014701 A1 | 1/2011 | Ghosh |
| 2011/0021416 A1 | 1/2011 | Shapiro |
| 2011/0027349 A1 | 2/2011 | Sable et al. |
| 2011/0028397 A1 | 2/2011 | Tozser et al. |
| 2011/0038917 A1 | 2/2011 | Kappers et al. |
| 2011/0065091 A1 | 3/2011 | Van Der Hoek |
| 2011/0104146 A1 | 5/2011 | Faraday |
| 2011/0152176 A1 | 6/2011 | Horswill |
| 2011/0189774 A1 | 8/2011 | Mach et al. |
| 2011/0190234 A1 | 8/2011 | Nathan et al. |
| 2011/0195423 A1 | 8/2011 | Selinfreund et al. |
| 2011/0201109 A1 | 8/2011 | Zwaka et al. |
| 2011/0223241 A1 | 9/2011 | Tardi et al. |
| 2011/0257080 A1 | 10/2011 | Chai et al. |
| 2011/0262474 A1 | 10/2011 | Du et al. |
| 2011/0274721 A1 | 11/2011 | Nabel et al. |
| 2011/0275585 A1 | 11/2011 | Brahmbhatt et al. |
| 2011/0277180 A1 | 11/2011 | Romano |
| 2011/0287037 A1 | 11/2011 | Gentschev et al. |
| 2011/0293608 A1 | 12/2011 | Jaffee et al. |
| 2011/0305724 A1 | 12/2011 | Paterson et al. |
| 2012/0027785 A1 | 2/2012 | Dirienzo |
| 2012/0042413 A1 | 2/2012 | Albert et al. |
| 2012/0045474 A1 | 2/2012 | Motin et al. |
| 2012/0064062 A1 | 3/2012 | Goguen et al. |
| 2012/0064572 A1 | 3/2012 | Finlay et al. |
| 2012/0071545 A1 | 3/2012 | Shapiro |
| 2012/0088314 A1 | 4/2012 | Katanaev |
| 2012/0093773 A1 | 4/2012 | Li et al. |
| 2012/0142080 A1 | 6/2012 | Bermudes |
| 2012/0142623 A1 | 6/2012 | Lagunoff et al. |
| 2012/0164687 A1 | 6/2012 | Bereta et al. |
| 2012/0219545 A1 | 8/2012 | Ayuso et al. |
| 2012/0230976 A1 | 9/2012 | Helmerhorst et al. |
| 2012/0271036 A1 | 10/2012 | Smith et al. |
| 2012/0276132 A1 | 11/2012 | Feng et al. |
| 2012/0308575 A1 | 12/2012 | Guo et al. |
| 2013/0017173 A1 | 1/2013 | Nataro et al. |
| 2013/0023472 A1 | 1/2013 | Bristow |
| 2013/0028901 A1 | 1/2013 | Colonna et al. |
| 2013/0028924 A1 | 1/2013 | Ertl et al. |
| 2013/0102017 A1 | 4/2013 | Pfaendler et al. |
| 2013/0122043 A1 | 5/2013 | Guimaraes et al. |
| 2013/0129713 A1 | 5/2013 | Rescigno et al. |
| 2013/0150559 A1 | 6/2013 | Colonna et al. |
| 2013/0171109 A1 | 7/2013 | Helmerhorst et al. |
| 2013/0196432 A1 | 8/2013 | Poehlmann et al. |
| 2013/0202557 A1 | 8/2013 | Li et al. |
| 2013/0209405 A1 | 8/2013 | Curtiss et al. |
| 2013/0269057 A1 | 10/2013 | Fosu-Nyarko et al. |
| 2013/0276168 A1 | 10/2013 | Romaine et al. |
| 2013/0344033 A1 | 12/2013 | Vergnolle et al. |
| 2014/0005108 A1 | 1/2014 | Bristow |
| 2014/0056841 A1 | 2/2014 | Vachon |
| 2014/0057940 A1 | 2/2014 | Mankowski et al. |
| 2014/0093528 A1 | 4/2014 | Berkower |
| 2014/0150134 A1 | 5/2014 | Li et al. |
| 2014/0155343 A1 | 6/2014 | Brahmbhatt et al. |
| 2014/0162279 A1 | 6/2014 | Ramseier et al. |
| 2014/0162952 A1 | 6/2014 | Katagiri et al. |
| 2014/0173774 A1 | 6/2014 | Pareddy et al. |
| 2014/0173780 A1 | 6/2014 | Pareddy et al. |
| 2014/0194346 A1 | 7/2014 | Aebi et al. |
| 2014/0220661 A1 | 8/2014 | Bermudes |
| 2014/0227286 A1 | 8/2014 | Jaffee et al. |
| 2014/0234310 A1 | 8/2014 | Shapiro |
| 2014/0287419 A1 | 9/2014 | Althoff et al. |
| 2014/0289906 A1 | 9/2014 | Althoff et al. |
| 2014/0296480 A1 | 10/2014 | Sanchez Garcia et al. |
| 2014/0322790 A1 | 10/2014 | Sebastian et al. |
| 2014/0370036 A1 | 12/2014 | Shapiro |
| 2015/0004705 A1 | 1/2015 | Lu et al. |
| 2015/0017138 A1 | 1/2015 | Fruehauf et al. |
| 2015/0017204 A1 | 1/2015 | Bermudes |
| 2015/0030573 A1 | 1/2015 | Fruehauf et al. |
| 2015/0044256 A1 | 2/2015 | Dattwyler et al. |
| 2015/0050308 A1 | 2/2015 | van der Hoek |
| 2015/0057191 A1 | 2/2015 | Tissot et al. |
| 2015/0071957 A1 | 3/2015 | Kelly et al. |
| 2015/0125849 A1 | 5/2015 | Yeh et al. |
| 2015/0132330 A1 | 5/2015 | Garcia-Sastre et al. |
| 2015/0139940 A1 | 5/2015 | Bermudez Humaran et al. |
| 2015/0153358 A1 | 6/2015 | Ayuso et al. |
| 2015/0184220 A1 | 7/2015 | Sebastian et al. |
| 2015/0197748 A1 | 7/2015 | Liu et al. |
| 2015/0216965 A1 | 8/2015 | Diamond et al. |
| 2015/0225692 A1 | 8/2015 | Bhatia et al. |
| 2015/0231207 A1 | 8/2015 | Kaspar |
| 2015/0246137 A1 | 9/2015 | Guo et al. |
| 2015/0291667 A1 | 10/2015 | Dirienzo |
| 2015/0337321 A1 | 11/2015 | Mach et al. |
| 2015/0351390 A1 | 12/2015 | Castle et al. |
| 2015/0355172 A1 | 12/2015 | Kraus et al. |

FOREIGN PATENT DOCUMENTS

| | | |
|---|---|---|
| EP | 1655370 | 5/2006 |
| JP | 2009269922 | 11/2009 |
| WO | WO1991000014 | 1/1991 |
| WO | WO9638159 | 12/1996 |
| WO | WO9640238 | 12/1996 |
| WO | WO1996040238 | 12/1996 |
| WO | WO9714782 | 4/1997 |
| WO | WO1997014782 | 4/1997 |
| WO | WO9833923 | 8/1998 |
| WO | WO1999010014 | 3/1999 |
| WO | WO1999010485 | 3/1999 |
| WO | WO0004919 | 2/2000 |
| WO | WO2000004919 | 2/2000 |
| WO | WO2001014579 | 3/2001 |
| WO | WO0125397 | 4/2001 |
| WO | WO2001025397 | 4/2001 |
| WO | WO02070645 | 9/2002 |
| WO | WO2002070645 | 9/2002 |
| WO | WO03072125 | 9/2003 |
| WO | WO2003072125 | 9/2003 |
| WO | WO03102168 | 12/2003 |
| WO | WO2003102168 | 12/2003 |
| WO | WO2004076484 | 9/2004 |
| WO | WO2004103404 | 12/2004 |
| WO | WO2005014618 | 2/2005 |
| WO | WO2005018332 | 3/2005 |
| WO | WO2005054477 | 6/2005 |
| WO | WO2006010070 | 1/2006 |
| WO | WO2006013441 | 2/2006 |
| WO | WO2006048344 | 5/2006 |
| WO | WO2006116545 | 11/2006 |
| WO | WO2007083193 | 7/2007 |
| WO | WO2008073148 | 6/2008 |
| WO | WO2008091375 | 7/2008 |
| WO | WO2008156702 | 12/2008 |
| WO | WO2009006450 | 1/2009 |
| WO | WO2009006453 | 1/2009 |
| WO | WO2009014650 | 1/2009 |
| WO | WO2009086116 | 7/2009 |
| WO | WO2009126189 | 10/2009 |

(56) References Cited

FOREIGN PATENT DOCUMENTS

| WO | WO2009139985 | 11/2009 |
| WO | WO2009145956 | 12/2009 |
| WO | WO2009150433 | 12/2009 |
| WO | WO2009152480 | 12/2009 |
| WO | WO2010036391 | 4/2010 |
| WO | WO2010057009 | 5/2010 |
| WO | WO2011017137 | 2/2011 |
| WO | WO2011086172 | 7/2011 |
| WO | WO2012104025 | 8/2012 |
| WO | WO2012150269 | 11/2012 |
| WO | WO2013067185 | 5/2013 |

OTHER PUBLICATIONS

Hu, Yan, et al. "Bacillus subtilis strain engineered for treatment of soil-transmitted helminth diseases." Applied and environmental microbiology 79.18 (2013): 5527-5532.
Bermudes, David, et al. "Tumour-selective Salmonella-based cancer therapy." Biotechnology and Genetic Engineering Reviews 18.1 (2001): 219-233.
Pawelek, John M., K. Brooks Low, and David Bermudes. "Tumor-targeted Salmonella as a novel anticancer vector." Cancer research 57.20 (1997): 4537-4544.
Carroll, J., J. Li, and D. J. Ellar. "Proteolytic processing of a coleopteran-specific δ-endotoxin produced by Bacillus thuringiensis var. tenebrionis." Biochemical Journal 261.1 (1989): 99-105.
Friedlos, Frank, et al. "Attenuated Salmonella targets prodrug activating enzyme carboxypeptidase G2 to mouse melanoma and human breast and colon carcinomas for effective suicide gene therapy." Clinical Cancer Research 14.13 (2008): 4259-4266.
Efficacy, Wikipedia, Mar. 21, 2016.
Bacillus thuringiensis, University of Califonia San Diego, Mar. 21, 2016; http://www.bt.ucsd.edu/how_bt_work.html.
Gaofu, Qi, et al. "In vitro assessment of plant lectins with anti-pinwood nematode activity." Journal of invertebrate pathology 98.1 (2008): 40-45.
Clairmont, C., et al. "Biodistribution and Genetic Stability of the Novel Antitumor Agent VNP20009, a Genetically Modified Strain of Salmonella typhimuvium." Journal of Infectious Diseases 181.6 (2000): 1996-2002.
Murray, Sean R., et al. "Extragenic Suppressors of Growth Defects inmsbB Salmonella." Journal of bacteriology 183.19 (2001): 5554-5561.
Larsson, Helena, et al. "A novel anti-angiogenic form of antithrombin with retained proteinase binding ability and heparin affinity." Journal of Biological Chemistry 276.15 (2001): 11996-12002.
Sznol, Mario, et al. "Use of preferentially replicating bacteria for the treatment of cancer." The Journal of clinical investigation 105.8 (2000): 1027-1030.
Wang, Suming, et al. "Design of peptide inhibitors for furin based on the C-terminal fragment of histone H1.2." Acta biochimica et biophysica Sinica 40.10 (2008): 848-854.
Laskowski Jr, Michael, and Ikunoshin Kato. "Protein inhibitors of proteinases." Annual review of biochemistry 49.1 (1980): 593-626.
Shiga, Yasuhiro, et al. "Characterization of an extracellular protease inhibitor of Bacillus brevis HPD31 and nucleotide sequence of the corresponding gene." Applied and environmental microbiology 58.2 (1992): 525-531.
Taguchi, Seiichi, Izumi Kumagai, and Kin-ichiro Miura. "Comparison of secretory expression in Escherichia coli and Streptomyces of Streptomyces subtilisin inhibitor (SSI) gene." Biochimica et Biophysica Acta (BBA)-Gene Structure and Expression 1049.3 (1990): 278-285.
MacIntosh, Susan C., et al. "Potentiation of Bacillus thuringiensis insecticidal activity by serine protease inhibitors." Journal of Agricultural and Food Chemistry 38.4 (1990): 1145-1152.
Wasilewski, Margaret M., et al. "Cysteine protease inhibitors block schistosome hemoglobin degradation in vitro and decrease worm burden and egg production in vivo." Molecular and biochemical parasitology 81.2 (1996): 179-189.
Deist, Benjamin R et al. "Bt toxin modification for enhanced efficacy." Toxins 6.10 (2014): 3005-3027.
Thaul, Susan. "How FDA approves drugs and regulates their safety and effectiveness." (2012).
Oppert, Brenda. "Protease interactions with Bacillus thuringiensis insecticidal toxins." Archives of insect biochemistry and physiology 42 (1999): 1-12.

Mourão, Caroline BF, and Elisabeth F. Schwartz. "Protease inhibitors from marine venomous animals and their counterparts in terrestrial venomous animals " Marine drugs 11.6 (2013): 2069-2112.

Wei, Jun-Zhi, et al. "Bacillus thuringiensis crystal proteins that target nematodes." Proceedings of the National Academy of Sciences 100.5 (2003): 2760-2765.

Hu, Yan, et al. "Mechanistic and single-dose in vivo therapeutic studies of Cry5B anthelmintic action against hookworms." PLoS Negl Trop Dis 6.11 (2012): e1900.

Urban Jr, Joseph F., et al. "Bacillus thuringiensis-derived Cry5B has potent anthelmintic activity against Ascaris suum." PLoS Negl Trop Dis 7.6 (2013): e2263.

Suming Wang, Jinbo Han, Yanfang Wang, Wuyuan Lu, and Chengwu Chi, "Design of peptide inhibitors for furin based on the C-terminal fragment of histone H1.2", Acta Biochim Biophys Sin (2008), vol. 40, Issue 10, p. 848-854.

http://en.wikipedia.org/wiki/Neutrophil (accesed Jul. 1, 2014).

http://en.wikipedia.org/wiki/Macrophage (Acessed Jul. 1, 2014).

http://en.wikipedia.org/wild/T-cell (Accessed Jul. 1, 2014).

http://www.uniprot.org/uniprot/Q4GWU5, Q4GWU5 (SFTI1. sub.—Helan) Reviewed, UniProtKB/Swiss-Prot, Trypsin inhibitor 1 (SFTI-1) (Acessed Jul. 1, 2014).

http://www.ebi.ac.uk/pdbe-site/pdbemotif/sequence?accessionCode=1o8y (Acessed Jul. 1, 2014) Enzymatic Cyclization of a Potent Bowman-Birk Protease Inhibitor, Sunflower Trypsin Inhibitor-1, and Solution Structure of an Acyclic Precursor Peptide, Marx, U.C.search; Korsinczky, M.search; Schirra, H.search; Jones, A. search; Condie, B.search; Otvos, L.; Craik, D.J., J.Biol.Chem.search vol. 278, pag:21782 (2003), PubMed ID (U.S. Appl. No. 12/621,047) DOI (10.1074/jbc.M212996200).

* cited by examiner

A) Hly CABD from E. Coli

B) Hx CABD from Actinobacillus

C) Hybrid CABD from E. Coli and Actinobacillus

D) Hybrid CABD from E. Coli and Actinobacillus with a chimeric A which has the C-terminus of the E. coli A

PROTEASE INHIBITOR: PROTEASE SENSITIVE EXPRESSION SYSTEM COMPOSITION AND METHODS IMPROVING THE THERAPEUTIC ACTIVITY AND SPECIFICITY OF PROTEINS DELIVERED BY BACTERIA

CROSS REFERENCE TO RELATED APPLICATIONS

The present application is a Division of U.S. patent application Ser. No. 14/016,407, filed Sep. 3, 2013, now U.S. Pat. No. 9,068,187, issued Jun. 30, 2015, which is a Division of U.S. patent application Ser. No. 13/024,172, filed Feb. 9, 2011, now U.S. Pat. No. 8,524,220, issued Sep. 3, 2013, which is a non-provisional of U.S. Provisional Patent Application No. 61/302,938, filed Feb. 9, 2010, each of which is expressly incorporated herein by reference in its entirety.

1. FIELD OF THE INVENTION

This invention is generally in the field of therapeutic delivery systems, systems and methods for providing co-expression of protease inhibitors with genetically engineered protease sensitive therapeutic constructs, and chimeric proteins.

2. BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41). However, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella Typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO 2009/126189, WO 03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, each of which is expressly incorporated herein by reference), but these approaches pose risks of systemic toxicity.

Use of protein toxins for treatment of various disorders including inflammation, autoimmunity, neurological disorders and cancer has long-suffered from off-target toxicity. Enhancing toxin specificity, which offers the potential to eliminate side effect, has been achieved by several different means, such as attachment of a specific antibodies or peptide ligand (e.g., *Pseudomonas* endotoxin A (PE-ToxA) antibody conjugate, known as an immunotoxin). Based upon the binding specificity of the attached antibody moiety for a specific target, enhanced specificity of the target is achieved. Other toxins have been engineered to achieve specificity based upon their site of activation. For example, proaerolysin requires proteolytic activation to become the cytotoxic protein aerolysin. Substitution of the natural protease cleavage site for a tumor-specific protease cleavage site (e.g., that of the prostate specific antigen (PSA) protease or urokinase) results in a toxin selectively activated within tumors (Denmeade et al. WO 03/018611 and Denmeade et al. U.S. Pat. No. 7,635,682). Another similar activation system has utilized ubiquitin fusion, coupled with a hydrolysable tumor protease (e.g., PSA) sequence and a toxin (e.g., saporin), as described by Tschrniuk et al. 2005 (Construction of tumor-specific toxins using ubiquitin fusion technique, Molecular Therapy 11: 196-204). However, while some specificity is engendered and thus these activated protein types are useful in the present invention as modified herein, in these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258: 417-424), resulting in a dose-limiting toxicity. Renal injury has occurred in some patients treated with immunotoxins, which may be due to micro-aggregates of the immunotoxin (Frankel et al., 2001, Blood 98: 722a). Liver damage from immunotoxins is a frequent occurrence that is believed to be multifactorial (Frankel, 2002, Clinical Cancer Research 8: 942-944). To date, antibodies linked to proteinaceous toxins have limited success clinically. One explanation for the off target toxicity is that although a specific agent is targeted to the tumor and/or specifically activated there, the agent is also toxic if it diffuses out of the tumor, which is likely to occur due to the high osmotic pressure that occurs within tumors (Jain, R. K., 1994, Barriers to drug delivery in solid tumors, Scientific American 271 (11): 58-65). Once activated inside the tumor and having diffused back outside, toxins such as aerolysin remain active and are able to contribute to non-target toxicity. Never-the-less, delivery of targeted pro-toxins is of interest by targeted bacteria if systemic toxicity can be overcome and the toxin remains active only at the target site.

Seed et al., WO/2009/014650 have suggested the fusion of proteases with *Vibrio cholerae* exotoxins. These authors suggest that protease (proteinase) inhibitors may hamper the activity of the fusions. They teach ways to maintain fusion protein activity and conclude for example: "Thus, it is possible to keep granzyme fusion proteins active in plasma through formulations using chondroitin sulfates". In the context of delivery by a tumor-localized vector, such activity would be expected to contribute to toxic side effects since the toxin would remain active in the blood and reach other organs of the body.

Use of secreted proteins in live bacterial vectors has been demonstrated by several authors. Holland et al. (U.S. Pat. No. 5,143,830, expressly incorporated in its entirety herein by reference) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Micobiology 71: 656-662) using a modified hlyB, and by Gupta and Lee (2008 Biotechnology and Bioengineering, 101: 967-974) by addition of rare codons to the hlyA gene, each of which is expressly incorporated by reference in their entirety herein. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154, expressly incorporated by reference in its entirety herein). The autotransporter surface display has been described by Berthet et al., WO/2002/070645, expressly incorporated by reference herein. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999) demonstrated hybrid proteins containing the □-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella* muenchen (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, expressly incorporated by reference in their entirety herein). Multihybrid FliC insertions of up to 302 amino acids have also been prepared (Tanskanen et al. 2000, Appl. Env. Microbiol. 66: 4152-4156, expressly incorporated by reference in its entirety herein). Trimerization of antigens can be achieved using the T4 fibritin foldon trimerization sequence (Wei et al. 2008 J. Virology 82: 6200-6208) and VASP tetramerization domains (Kühnel et al., 2004 PNAS 101: 17027-17032), expressly incorporated by reference in their entirety herein. The multimerization domains are used to create, bi-specific, tri-specific, and quad-specific targeting agents, whereby each individual agent is expressed with a multimerization tag, each of which may have the same or separate targeting peptide, such that following expression, surface display, secretion and/or release, they form multimers with multiple targeting domains.

Surprisingly, although bacteria have been used vectors for neoplastic disease and several authors have suggested delivering cytotoxins and other agents, no means of conferring safety and specificity of the actual cytotoxic agent has been developed within the delivery platform itself. Therapeutic protein activity proximal to the delivery vector at the target site, such as a solid tumor, lymphoma or leukemic bone marrow, and inactivation distal to the delivery vector, has remained to be achieved.

3. SUMMARY OF THE INVENTION

3.1 Therapeutic Molecules and Protease Inhibitors

The present invention consists of known and/or novel chimeric proteins, or combination of proteins, that are expressed, secreted, surface displayed and/or released by bacteria and result in anti-cancer activity or have direct inhibitory or cytotoxic anti-neoplastic activity. The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intrathecally (intrathecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic benefit by reducing or eliminating the disease, malignancy and/or neoplasia.

The present invention further consists of the co-expression by a bacterial expression system, or a combination of bacterial expression systems, of one or more protease inhibitors together with one or more protease sensitive therapeutic agent. The therapeutic agent may be inherently sensitive to proteases, or engineered to have enhanced sensitivity. Within the local high-concentration of the targeted tissue or cells such as the confines of a solid tumor, lymph node or lumen of a bone, the protease inhibitor prevents the degradation of the therapeutic agent that is therapeutically active against the target tissue such as colon cancer cells within a tumor, lymphoma cells within a lymph node, or leukemic cells within the lumen of a bone. Upon egress from the confined space of the targeted tissue, the inhibitor falls below the inhibitory concentration, and the therapeutic agent which is protease sensitive is freely degraded, thus deactivating it outside the target site, resulting in cell or tissue-specific activity as well as increased activity and inactivation in non-target cell or tissues (Table I). A schematic diagram comparing the relative effect of co-expression is shown in FIG. 1. This surprising solution to the problem of off target toxicity by a tumor targeting vector stems from the unique localized production of therapeutic agents by tumor-targeted vectors, wherein the active agent is produced locally and subsequently diffuses out resulting in systemic exposure rather than being injected peripherally with intent to treat distal sites.

TABLE 1

Projected relative effects of toxin forms with and without protease sensitivity and protease inhibitor(s).

| Composition | Tumor Efficacy | Systemic Toxicity |
|---|---|---|
| Unmodified toxins | +++ | +++ |
| Protease activated and/or insensitive toxin e.g., prostate protease activated Aerolysin | +++ | ++ |
| Protease sensitive (i.e., deactivated) toxin | + | — |
| Protease sensitive toxin + protease inhibitor | +++++ | — |

The types of cancers or neoplasias to which the present invention is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, aids-related cancers, aids-related lymphoma, anal cancer, appendix cancer, astrocytomas, childhood, teratoid/rhabdoid tumor, childhood, central nervous system tumors, basal cell carcinoma, bile duct cancer, extrahepatic bladder cancer, bladder cancer, bone cancer, osteosarcoma and malignant fibrous histiocytoma, brain stem glioma, brain tumor, brain stem glioma, central nervous system atypical teratoid/rhabdoid tumor, central nervous system embryonal tumors, brain tumor, astrocytomas, craniopharyngioma, ependymoblastoma, ependymoma, medulloblastoma, medulloepithelioma, pineal parenchymal tumors, supratentorial primitive neuroectodermal tumors and pineoblastoma, spinal cord tumors, breast cancer (female), breast cancer (male), bronchial tumors, burkitt lymphoma, carcinoid tumor, gastrointestinal, nervous system atypical teratoid/rhabdoid tumor, central nervous system embryonal tumors, central nervous system lymphoma, primary cervical cancer, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, embryonal tumors, endometrial cancer, ependymoblastoma, ependymoma, esophageal cancer, ewing sarcoma family of tumors, extracranial germ cell tumor, extrahepatic bile duct cancer, eye cancer, intraocular melanoma, eye cancer, retinoblastoma gallbladder cancer, gastric (stomach) cancer, gastrointestinal carcinoid tumor, gastrointestinal stromal tumor (gist), gastrointestinal stromal cell tumor, germ cell tumor, extracranial germ cell tumor, extragonadal germ cell tumor, ovarian gestational trophoblastic tumor, glioma, hairy cell leukemia, head and neck cancer, hepatocellular (liver) cancer, primary hepatocellular (liver) cancer, histiocytosis, langerhans cell, hodgkin lymphoma, hypopharyngeal cancer, intraocular melanoma, islet cell tumors (endocrine pancreas), kaposi sarcoma, kidney (renal cell) cancer, kidney cancer, langerhans cell histiocytosis, laryngeal cancer, leukemia, acute lymphoblastic leukemia, acute myeloid leukemia, chronic lymphocytic leukemia, chronic myelogenous leukemia, hairy cell leukemia, lip and oral cavity cancer, liver cancer, adult (primary) liver cancer, (primary) lung cancer, non-small cell lung cancer, small cell lymphoma, aids-related lymphoma, burkitt lymphoma, cutaneous T-cell lymphoma, hodgkin lymphoma, non-hodgkin lymphoma, primary central nervous system lymphoma, macroglobulinemia, Waldenström malignant fibrous histiocytoma of bone and osteosarcoma, medulloblastoma, melanoma, intraocular (eye) melanoma, merkel cell carcinoma, mesothelioma, metastatic squamous neck cancer with occult primary, mouth cancer, multiple endocrine neoplasia syndrome, childhood multiple myeloma/plasma cell neoplasm, mycosis fungoides, myelodysplastic syndromes, myelodysplastic/myeloproliferative diseases, myelogenous leukemia, chronic myeloid leukemia, adult acute myeloid leukemia, childhood acute myeloma, multiple myeloproliferative disorders, nasal cavity and paranasal sinus cancer, nasopharyngeal cancer, nasopharyngeal cancer, neuroblastoma, non-hodgkin lymphoma, non-small cell lung cancer, oral cancer, oral cavity cancer, lip and oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, islet cell tumors, papillomatosis, paranasal sinus and nasal cavity cancer, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter, transitional cell cancer, respiratory tract carcinoma involving the nut gene on chromosome 15, retinoblastoma, rhabdomyosarcoma, salivary gland cancer, sarcoma, ewing sarcoma family of tumors, kaposi sarcoma, soft tissue sarcoma, uterine sarcoma, Sézary syndrome, skin cancer (nonmelanoma), melanoma, skin carcinoma, merkel cell, small cell lung cancer, small intestine cancer, soft tissue sarcoma, squamous cell carcinoma, see skin cancer (nonmelanoma), squamous neck cancer with occult primary, metastatic stomach (gastric) cancer, stomach (gastric) cancer, supratentorial primitive neuroectodermal tumors, T-cell lymphoma, cutaneous T-cell lymphoma, mycosis fungoides and Sézary syndrome, testicular cancer, throat cancer, thymoma and thymic carcinoma, thyroid cancer, transitional cell cancer of the renal pelvis and ureter, trophoblastic tumor, (gestational), unknown primary site, carcinoma of, unknown primary site carcinoma, ureter and renal pelvis, transitional cell cancer, urethral cancer, uterine cancer, endometrial uterine sarcoma, vaginal cancer, vulvar cancer, Waldenström macroglobulinemia, and Wilms tumor.

The therapeutic agent can be a peptide or protein, toxin, chimeric toxin, cytokine, antibody, bispecific antibody including single chain antibodies, camel antibodies and nanobodies chemokine, prodrug converting enzyme or metabolite-degrading enzyme such as thiaminase, methionase (methioninase, L-methionine γ-lyase) or asparaginase. In a preferred embodiment the therapeutic agent is a toxin, or modified toxin.

Toxins, therapeutic cytokines and other molecules, homologs or fragments thereof useful in conjunction with the present invention include small lytic peptides, larger lytic peptides, pore-forming toxins, protein inhibitors, extracellular DNAases (DNase), intracellular DNAases, apoptosis inducing peptides, cytokines, prodrug converting enzymes, metabolite destroying enzymes, ribonucleases, antibody inactivating toxins and other anticancer peptides. In a preferred embodiment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting system described herein, including but not limited to the proteins azurin, carboxyesterase Est55 (a prodrug converting enzyme from *Geobacillus* that activates CPT-11 to SN-38), thiaminase (e.g., from *Bacillus*), methionase (methioninase), asparaginase, apoptin, bax, bim, p53, BAK, BH3 peptide (BCL2 homology domain 3), cytochrome C, thrombospondin, platelet factor 4 (PF4) peptide, *Bacillus* sp. *cytolysins*, *Bacillus* sp. nheABC toxins, cytolethal distending toxins (cldt), typhoid toxins (pertussis like toxin) (pltAB), pertussis toxin, cldt:plt hybrids, actAB, cytotoxic nectrotic factor (cnf), dermonecrotic factor (dnf), shiga toxins and shiga-like toxins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press) including membrane depolarizing (or pore-forming), DNAases (including colicin DNase, Staphylococcal Nuclease A:OmpA fusions (Takahara et al., 1985 J Biol. Chem 260: 2670-2674), *Serratia marcescens* DNase (Clegg and Allen, 1985, FEMS Microbiology Letters 27: 257-262; Vibrio DNase Newland et al., 1985 Infect Immun 47: 691-696) or other bacterial DNase), RNAases, and tRNAases, including but not limited colicin A, colicin D, colicin E5, colicin E492, microcin M24, colE1, colE2, colE3, colE5 colE7, coleE8, colE9, col-Ia, colicin N and colicin B, membrane lytic peptides from *Staphalococcus* (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48, Eschericia *coli, Vibrio* and *Yersinia* species heat stable enterotoxins, Alouf and Popoff (eds), 2006, Comprehensive Sourcebook of Bacterial Protein Toxins, Third Edition, Academic Press), autotransporter toxins including but not limited to IgA protease, picU espC, and sat, *Staphalococcus* protein A, *clostridium* enterotoxin, *Clostridium difficile* toxin A, scorpion chlorotoxin, aerolysin, subtilase, cereolysin, *Staphalococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-haemolysins, HlgA/HlgB and HlgC/HlgB and leukocidin Panton-Valentine, LukS-PV/LukF-PV (Luk-PV, PVL)) TRAIL, fasL, IL-18, CCL-21, human cytokine LIGHT, agglutinins (*Maackia amurensis*, wheat germ, *Datura stramonium, Lycopersicon* (tomato) plant lectin, leukoagglutinin (L-PHA, *Helix pomatia*) saporin, ricin, pertussis toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press; each of which is expressly incorporated by reference in their entirety herein).

Metabolite toxins such as the *Chromobacterium violacium* dipsepeptides (Shigeatsu et al., 1994, FR901228, a novel antitumor bicyclic depsipeptide produced by *Chromobacterium violaceum* No. 968. II. Structure determination. J Antibiot (Tokyo) 47(3):311-4) or those from *Serratia* are also of use in the present invention.

Bacterial collagenases (Harrington, 1996, Infect. Immun. 64: 1885-1891) useful in the invention include but not limited to those from *Actinobacillus actinomycetemcomitans, Acinomadura* (*Streptomyces*) *madurae*, *Bacillus cereus*, *Bacteroides* spp., *Bifidobacterium* sp., *Bruecella melitensis, Capnocytophaga ochracea, Clostridium* spp., *Enterococcus faecalis, Echerichia coli, Eubacterium alactolyticum, Flavobacterium meningosepticum, Fusobacterium nucleatum, Peptococcus* sp., *Peptostreptococcus* spp., *Porphyromoas* (*Bacteroides*) spp., *Prevotella* (*Bacteroides*) spp., *Proteus mirabilis, Pseudomaons aeruginosa, Serratia marsescensm Serratia*, spp., *Staphalococcus* spp., *Streptococcus agalactiae* (group B *streptococcus*), *Streptococcus mutans, Streptococcus sobrinus* (*S. mutans* 6715), *Treponema* spp. and *Vibro vulnificus*), and those described in the MEROPS Database (Rawlings et al., 2010, MEROPS: The Peptidase Database, Nucleic Acids Res. 2010 (Database issue):D227-33.) including but not limited to those from *Clostridium histolyticum* (bacterial collagenase G/A), *Cytophaga* (cytophagalysin), *Empedobacter collagenolyticum* (*Empdeobacter* collagenase), *Helicobacter* (*Helicobacter*-type collagenase), *Porphyromonas* (*Porphyromonase*-type collagenase), *Geobacillus* sp. MO-1 (collagenolytic endopeptidase) and *Salmonella* sp. (*Salmonella*-type collegenase, including the collagenase from *Salmonella* DT-104), Alternatively, an endogenous collagenase may be activated by a transactivator, such as SlyA. (Carlson 2006, Microbial Pathogenesis 38: 181-187).

The chimeras may be further modified by addition of one or more multimerization domains, such as the T4 foldon trimerization domain (Meier et al., 2004, Journal of Molecular Biology, 344: 1051-1069; Bhardwaj et al., Protein Sci. 2008 17: 1475-1485) or tetramerization domains such as VASP (Kühnel et al., 2004 PNAS 101: 17027-17032). Chimeric toxins may be further modified by the addition of known cell penetrating (ferry) peptide which further improves their entry into target cells. Cell penetrating peptides include those derived from the HIV TAT protein (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or "Chariot" (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen (PPKKKRKV SEQ ID NO:1) monopartite NLS, or the nucleoplamin bipartite NLS (KR[PAATKKAGQA]KKKK SEQ ID NO:2, or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13: 495-508; Backendor et al., 2008, Apoptin: Therapeutic potential of an early sensor of carcinogenic transformation, Ann Rev Pharmacol Toxicol 48: 143-69).

The toxin may be further modified by addition of one or more protease cleavage sites that enhance its degradation outside of the tumor. Preferred protease cleavage sites are those for proteases that are under-expressed within the tumor compared to normal tissues (rather than over-expressed within the tumor as utilized for aerolysin activation). However, the expression levels of many proteases are elevated within tumors (e.g., Edwards et al., (eds) 2008, The Cancer Degradome: Proteases and Cancer Biology, Springer, expressly incorporated in its entirety herein). Preferred examples of proteases for which inhibitory peptides may be coexpressed including but not limited to furin, tissue plasminogen activator, activated protein C, factor Xa, granzymes (A, B & M), cathepsins (A, B, C, D, E, F, G, H, K, L, S, W & X), thrombin, plasmin, urokinase, matrix metalloproteases (1-28) membrane matrix metalloproteases (1-28), prostate specific antigen (PSA) and kallikrein 2. Furin, for example, recognizes a number of specific cleavage sites, including RXKR☐SX SEQ ID NO:3. In accordance with the present invention, the presence of this cleavage site, whether naturally occurring or introduced through genetic modification, may be compensated for within the target tissue by co-expression of a furin inhibitor, stabilizing its activity unless it escapes the target tissue such as a tumor, lymph node or lumen of a bone whereupon the inhibitor concentration drops and the effector protein is degraded. Use of protease inhibitors alone or in combination by bacterial delivery vectors has not previously been suggested. Indeed, Wang et al. 2008 (Acta Biochim Biophys Sin (Shanghai). 2008 October; 40(10):848-54) suggested furin inhibitors could be used as antibiotics to suppress bacterial infection which would thereby interfere with delivery by a bacterial vector. Therefore, it has not been considered desirable to use a furin inhibitor or other protease inhibitors to have a positive effect on the bacteria and/or the therapeutics they release.

The peptide inhibitors are engineered to be secreted from the gram negative bacteria secretion signals known to those skilled in the arts, including *E. coli* cytolethal distending toxin, Shiga toxin, LPP:OmpA, M13pIII, M13pVIII, zirS (Finlay et al., 2008, PLoS Pathogens 4 (4), e100003), heat-stable (ST; thermostable) toxins from *Escherichia* and *Vibrio* (U.S. Pat. No. 5,399,490), *E. coli* enterotoxin II (Kwon et al., U.S. Pat. No. 6,605,697) N-terminal signal sequences, or hlyA C-terminal signal sequence (requires addition of hlyBD and TolC), or by colicin fusions together with colicin lysis proteins, or using autotransporter (autodisplay) fusions. Fusion to the M13 pIX may also be used (WO 2009/086116) or fusions to type III secretion system of *Salmonella* or other bacteria (Wilmaier et al., 2009 Mol Sys Biol 5: 309. The inhibitors can be further modified to have the protease cleavage signal of the protease that they inhibit or for a different protease. Secretion signal from gram positive bacteria include that from listerialysin O (LLO), alkaline phosphatase (phoZ) (Lee et al., 1999, J Bacteriol. 181: 5790-5799), ClTase gene (Shiroza and Kuramitsu 1998, Methods in Cell Science, 20: 127-136) or the twin arginine translocation system (Berks et al., 2005, Protein targeting by the bacterial twin-arginine translocation (Tat) pathway, Current Opinion in Microbiology 8: 174-181). Enhanced secretion may be achieved as described in U.S. Pat. No. 7,358,084, WO/2009/139985 Methods and materials for gastrointestinal delivery of a pathogentoxin binding agent; van Asseldonk, M et al. 1990, Cloning of usp45, a gene encoding a secreted protein from *Lacotococcs lactis* subsp. *lactis* MG1363 Gene 95, 15-160; Kim et al., Display of heterologous proteins on the surface of *Lactococcus lactis* using the H and W domain of PrtB from *Lactobacillus delburueckii* subsp. *bulgaricus* as an anchoring matrix J Appl Microbiol. 2008 June; 104(6):1636-43. Epub 2008 Feb. 19).

The chimeric proteins may have one or more additional features or protein domains known to those skilled in the arts which are designed to be active or catalytic domains that result in the death of the cell, allow or facilitate them being secreted or released by autolytic peptides such as those associated with colicins or bacteriophage release peptides have targeting peptides that direct them to the target cells, and protease cleavage sites for activation (e.g., release from parent peptide), and thioredoxin or glutathione S-transferase (GST) fusions that improve solubility.

The present invention also provides in accordance with some embodiments, unique chimeric modifications of the above listed toxins that contain specific combinations of components resulting in secretion by selective anti-tumor activity. The invention also provides extracellular protease sensitivity (deactivation) that may include the addition of protease cleavage sites and may be co-expressed with a protease inhibitor. The chimeric proteins may have one or more additional features or protein domains known to those skilled in the arts which are designed to 1) be active or catalytic domains that result in the death of the cell or make them susceptible to other known anticancer agents, 2) allow or facilitate them being secreted or released by autolytic peptides such as colicin release peptides, 3) membrane protein transduction (ferry) peptides, 4) autotransporter domains, 5) have targeting peptides that direct them to the target cells, and 6) protease cleavage sites for activation (e.g., release from parent peptide). However, the specific organization and combination of these domains is unique and specific to the invention.

Bombesin and gastrin are amidated peptides. Amidation of these peptides would not be expected to occur in gram-negative bacteria. A unique composition in accordance with one embodiment of the present invention is the co-expression of the C-terminal amidating enzyme, which results in amidating these peptides in order for them to confer their targeting specificity.

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10: 2299-2310, the entirety of which is expressly incorporated herein by reference). Small lytic peptides useful in the invention are those derived from *Staphaloccus aureus, S. epidermidis* and related species, including the phenol-soluble modulin (PSM) peptides and delta-lysin (Wang et al., 2007 Nature Medicine 13: 1510-1514, expressly incorporated herein by reference). Larger lytic peptides that may be used includes the actinoporins from sea anemones or other coelenterates, such as SrcI, FraC equinatoxin-II and sticholysin-II (Anderluh and Macek 2002, Toxicon 40: 111-124). The selection of the lytic peptide depends upon the primary purpose of the construct, which may be used in combination with other constructs providing other anticancer features. Construct designed to be directly cytotoxic to cells employ the more cytoxic peptides, particularly PSM-alpha-3 and actinoporins. Constructs which are designed to use the lytic peptide to affect escape from the endosome use the peptides with the lower level of cytotoxicity, such as PSM-alpha-1, PSM-alpha-2 or delta-lysin.

Promoters, i.e., genetic regulatory elements that control the expression of the genes encoding the therapeutic molecules described above that are useful in the present invention include constitutive and inducible promoters. A preferred constitutive promoter is that from the vector pTrc99a (Promega). Preferred inducible promoters include the tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397), the arabinose inducible promoter (Ara$_{BAD}$) (Lossner et al., 2007, Cell Microbiol. 9: 1529-1537; WO/2006/048344) the salicylate (Aspirin) derivatives inducible promoter (Royo et al., 2007, Nature Methods 4: 937-942; WO/2005/054477), or a tumor-specific promoter (Arrach et al., 2008, Cancer Research 68: 4827-4832; WO/2009/152480). A single promoter may be used to drive the expression of more than one gene, such as a protease sensitive toxin and a protease inhibitor. The genes may be part of a single synthetic operon (polycistronic), or may be separate, monocistronic constructs, with separate individual promoters of the same type used to drive the expression of their respective genes. The promoters may also be of different types, with different genes expressed by different constitutive or inducible promoters. Use of two separate inducible promoter for more than one cytotoxin or other effector type peptide allows, when sufficient X-ray, tetracycline, arabinose or salicylic acid is administered following administration of the bacterial vector, their expression to occur simultaneously, sequentially, or alternatingly (repeated).

3.2 Non-Conjugative, Bacteria

The present invention provides, according to some embodiments, a composition that would minimize the effect of bacteria released into the environment by eliminating the ability of the bacteria to exchange genetic information with related bacteria, as well as provide a delivery enhancing bacteria resulting in a greater therapeutic effect. Conjugative transfer is a major genetic exchange mechanism that may occur between *Salmonella* and the normal commensal gut bacterium *E. coli*, requiring the presence of an F' factor. The present invention provides gram-negative bacteria including *E. coli, Vibrio, Shigella* and *Salmonella* that are genetically modified in one or more ways to eliminate conjugative transfer of DNA with closely related species including *E. coli*. One of the modifications works on both male (F'+) and female (F'−) bacteria. These modifications facilitate the safety of a bacteria carrying expressing chimeric toxins. The F' factor provides functions which may be undesirable in conjunction with aspects of the present invention, including mating stabilization and DNA transfer. The present invention therefore provides, according to one aspect, a composition lacking these features by their genetic disruption on the F' factor or by the cloning of the pilus factor genes into the tumor-targeted bacterium in the absence of the other factors, and hence, resulting in a strain which is non-conjugative and significantly less likely to transfer DNA to other bacteria. The invention may also incorporate entry exclusion into the bacteria and the fertility inhibition complex (finO and finP) and/or TraO, alone or in combination, and thus, even in tumor-targeted bacterial strains in which the pilus factors are not incorporated (i.e., F−), the bacterial strain will remain resistant to mating with F' bacteria.

3.3. Novel Methods for Testing the Efficacy of Engineered Effector Proteins Using Strains with Low-Level Tumor Targeting and/or Lower Antitumor Effects.

As cited above, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella Typhimurium* (VNP20009) administered by direct Intra-tumoral (IT) injection, Proc Am Soc Clin Oncol 20: abstr 1043; Nemunaitis et al., 2003, Pilot trial of genetically modified, attenuated *Salmonella* expressing the *E. coli* cytosine deaminase gene in refractory cancer patients, Cancer Gene Therapy 10: 737-744). However, one of the main differences between the murine studies (e.g., Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41), is that in most patients, the levels of the bacteria were significantly lower. For example, whereas in the murine models the bacteria frequently achieved levels of $1 \times 10^9$ per gram of tumor tissue, in humans the levels were significantly lower, e.g., $1 \times 10^6$ was achieved in 3 patients (Meir et al., 2001). Generally, it has been perceived that the murine studies should precede using bacteria with the greatest amount of tumor targeting. For example, Pawelek et al., WO/1996/040238 selected "super infective" bacteria by cycling through tumors. The novel cycling and selection procedure they employed selected for increased targeting numbers which was correlated with a greater antitumor effect. A similar study was performed by Zhao et al., 2005, (Tumor-targeting bacterial therapy with amino acid auxotrophs of GFP-expressing *Salmonella typhimurium*. Proc Natl Acad Sci USA. 102: 755-760).

In the isolation of the *Salmonella* strain A1-R by re-isolation form a tumor, as described by the same group in a later study (Hayashi et al., 2009, Cancer metastasis directly eradicated by targeted therapy with a modified *Salmonella Typhimurium*, Journal of Cellular Biochemistry 106: 992-998). "The idea was to increase the tumor targeting capability of the bacteria." Thus, developing and testing bacteria with enhanced tumor targeting has been a focus within the field. However, while it is desirable to find ways to improve the levels of bacteria within tumors, including the present invention, the importance of selecting an appropriate model to assess the contribution that an effector system might have in a human, or how it might improve tumor colonization levels, wherein the model should provide lower (rather than higher) levels of tumor colonization, has not been appreciated. It has not been understood that to evaluate how an effector system such as the herpes simplex thymidine kinase or cytosine deaminase described by Pawelek et al., WO/1996/040238, or those provided in the present invention, would function in humans where lower targeting numbers might be expected (at least at the outset; greater number could be achieved if the effector system is effective), such that the murine system where the tumor-targeting level is similar to the level achieved in humans represents an appropriate model.

As described by Pawelek et al., fir A is a mutation within the gene that encodes the enzyme UDP-3-O(R-30 hydroxymyristoyl)-glycocyamine N-acyltransferase, that regulates the third step in endotoxin biosynthesis (Kelley et al., 1993, J. Biol. Chem. 268:19866-19874). *Salmonella typhimurium* and *E. coli* strains bearing this type of mutation produce a lipid A that differs from wild type lipid A in that it contains a seventh fatty acid, a hexadecanoic acid (Roy and Coleman, 1994, J. Bacteriol. 176:1639-1646). Roy and Coleman demonstrated that in addition to blocking the third step in endotoxin biosynthesis, the firA' mutation also decreases enzymatic activity of lipid A 4' kinase that regulates the sixth step of lipid A biosynthesis. *Salmonella typhimurium* strain SH5014 and its firA' derivative SH7622 are described in Hirvas et al, 1991, EMBO J. 10:1017-1023. The genotypes of these strains are as follows: strain SH5014 ilv-1178 thr-914 ήis-6116 metA22 metE551 trpB2 xyl-404 H1-b H2-e, n, x flaA66 rpsL120 rfaJ4041; strain SH7622 ilv-1178 thr-914 his-6116 metA22 metE551 trpB2 xyl-404 H1-b H2-e, n, x flahββ rpsL120 rfaJ4041, ssc-1 (firA$^{ts}$). A derivative of *Salmonella typhimurium* firA' strain SH7622 was picked, designated SH7622-64, and used as the firA' strain for the experiments. SH7622-64 was selected for its supersensitivity to the antibiotic novobiocin and temperature-sensitive growth, characteristics of the firA' SH7622 strain. When studies in two different tumor models, Pawelek et al. found *Salmonella*/g tissue: Primary Tumor of M27 lung cancer, 2.9×10$^6$ per gram and in B16 melanoma, 3.2×10$^5$ per gram, yet retaining a similar 3200:1 tumor to liver targeting ratio. This strain, while never used in any subsequent studies represents a surprising solution to translating murine to human studies, wherein both systems tend to have the same number of bacteria per gram of target tissue.

In an alternative approach, as opposed to selecting bacteria with optimal antitumor effects as is commonly applied (Zhao et al., 2005 (Tumor-targeting bacterial therapy with amino acid auxotrophs of GFP-expressing *Salmonella typhimurium*. Proc Natl Acad Sci USA. 102: 755-760).), bacterial mutants are selected for suboptimal or low antitumor effects. The bacterial mutants can be generated by any standard method of mutation (e.g., UV, nitrosoguanadine, Tn10, Tn5), or can be a spontaneous mutation such as a suppressor mutation (e.g., Murray et al., 2001, Extragenic suppressors of growth defects in msbB *Salmonella*, J. Bacteriol. 183: 5554-5561).

4. OBJECTS OF THE INVENTION

The present invention provides, according to one embodiment, live attenuated therapeutic bacterial strains that express one or more therapeutic molecules together with one or more protease inhibitor polypeptides that inhibit local proteases that could deactivate the therapeutic molecules. In particular, one aspect of the invention relates to live attenuated tumor-targeted bacterial strains that may include *Salmonella*, group B *Streptococcus* or *Listeria* vectoring chimeric anti-tumor toxins to an individual to elicit a therapeutic response against cancer. Another aspect of the invention relates to live attenuated tumor-targeted bacterial strains that may include *Salmonella*, group B *Streptococcus* or *Listeria* vectoring chimeric anti-tumor toxin molecules to an individual to elicit a therapeutic response against cancer including cancer stem cells. The toxins may also be targeted to tumor matrix cells, and/or immune cells.

Whereas the prior strains of *Salmonella* studied in human clinical trials used either no heterologous antitumor protein (i.e., VNP20009) or an antitumor protein located within the cytoplasm of the bacterium (i.e., cytosine deaminase expressed by TAPET-CD), or secreted proteins (Bermudes et al., WO 2001/025397) the invention provides, according to some embodiments, methods and compositions comprising bacterial vectors that express, secrete, surface display and/or release protease inhibitors that protect coexpressed protease sensitive antitumor molecules that are also secreted, surface displayed and/or released into the tumor, lymphoma-containing lymph node, leukemic bone lumen, or proximally or topically on a carcinoma or precancerous lesion for the treatment of the neoplasia.

The bacteria according to a preferred embodiment of the present invention include those modified to have little or no ability to undergo bacterial conjugation, limiting incoming and outgoing exchange of genetic material, whereas the prior art fails to limit exchange of genetic material. In addition, certain of the therapeutic molecules have co-transmission requirements (e.g., colicin proteins and colicin immunity) that are distal (i.e., genetically dissected and separated) to the therapeutic molecule location further limiting known forms of genetic exchange.

Aspects of the present invention also provide bacteria with antibody deactivating proteins that minimize the neutralizing effect of any vector specific antibodies and/or complement at the time of injection, or thereafter. The neutralizing proteins may be induced prior to injection into the host using known inducible promoters such that the bacteria are only temporarily antibody resistant, and may be optionally continuously produced thereafter at low level. Upon reaching the tumor site where the antibody penetration is poor, the bacteria no longer make the protein in sufficient quantity to have substantial spread to other tissues, except other tumor tissues and are controlled by neutralizing antibodies systemically, maintaining the safety of the bacteria.

Aspects of the present invention also provide novel chimeric bacterial toxins particularly suited for expression by gram-negative bacteria. The toxins may have added targeting ligands that render them selectively cytotoxic for tumor cells, tumor stem cells and/or matrix and tumor-infiltrating immune cells. The invention also provides means to determine optimal toxin combinations which are preferably additive or more preferably synergistic. The invention also provides means to determine the optimal combination of protein toxin with conventional cancer chemotherapeutics, liposomal agents or biologics, including immunosuppressive anti-complement agents (e.g., anti-C5B). Accordingly, administration to an individual, of a live *Salmonella* bacterial vector, in accordance with an aspect of the present invention, that is genetically engineered to express one or more protease inhibitors as described herein co-expressed with one or more cytotoxic proteins has the ability to establish a population in the tumor, kill tumor cells, tumor stem cells as well as tumor matrix and immune infiltrating cells, resulting in a therapeutic benefit.

Aspects of the present invention also provide novel methods to test the efficacy of the protease inhibitor and effector gene combinations described herein. The methods employ bacteria with low tumor colonization capability in order to establish the ability of low numbers of tumor-targeted bacteria to result in the desired effect, and bacteria with low inherent antitumor activity, such that the innate antitumor activity of a bacterial strain is minimized, and therefore less likely to mask the results of the effector systems.

A preferred composition will contain, for example, a sufficient amount of live bacteria expressing the protease inhibitors and cytotoxin(s) or effector proteins/peptides to produce a therapeutic response in the patient. Accordingly, the attenuated *Salmonella* strains described herein are both safe and useful as live bacterial vectors that can be orally administered to an individual to provide therapeutic benefit for the treatment of cancer.

Although not wishing to be bound by any particular mechanism, an effective antitumor response in humans by administration of genetically engineered, attenuated strains of *Salmonella* strains as described herein may be due to the ability of such mutant strains to persist within the tumor, lymphoma or leukemic bone marrow and to supply their own nutrient needs by killing tumor cells, tumor matrix and or immune infiltrating cells and further expanding the zone of the tumor that they occupy. Bacterial strains useful in accordance with a preferred aspect of the invention may carry the ability to produce a therapeutic molecule expressing plasmid or chromosomally integrated cassette that encodes and directs expression of one or more therapeutic molecules together with one or more protease inhibitors, as described herein. The protease inhibitors serve to prevent the destruction of the therapeutic molecule while within the tumor. The protease inhibitor may also have an anticlotting effect, wherein a blood clot may prevent spread of the bacteria throughout the tumor. The protease inhibitor may also have direct or indirect anticancer effects. If the cytotoxin and protease inhibitor diffuse outside of the tumor, lymph node, bone lumen, proximity to a carcinoma or other neoplasia-localized distribution, they fall below the protease inhibitory concentration, no longer inhibit proteolysis of the cytotoxins or effector genes, and are then inactivated. Thus the protease inhibitor system both increases activity and provides tumor specificity.

The serovars of S. enterica that may be used as the attenuated bacterium of the live compositions described in accordance with various embodiments herein include, without limitation, Salmonella enterica serovar Typhimurium ("S. typhimurium"), Salmonella montevideo, Salmonella enterica serovar Typhi ("S. typhi"), Salmonella enterica serovar Paratyphi B ("S. paratyphi 13"), Salmonella enterica serovar Paratyphi C ("S. paratyphi C"), Salmonella enterica serovar Hadar ("S. hadar"), Salmonella enterica serovar Enteriditis ("S. enteriditis"), Salmonella enterica serovar Kentucky ("S. kentucky"), Salmonella enterica serovar Infantis ("S. infantis"), Salmonella enterica serovar Pullorum ("S. pullorum"), Salmonella enterica serovar Gallinarum ("S. gallinarum"), Salmonella enterica serovar Muenchen ("S. muenchen"), Salmonella enterica serovar Anatum ("S. anatum"), Salmonella enterica serovar Dublin ("S. dublin"), Salmonella enterica serovar Derby ("S. derby"), Salmonella enterica serovar Choleraesuis var. kunzendorf ("S. cholerae kunzendorf"), and Salmonella enterica serovar minnesota (S. minnesota). A preferred serotype for the treatment of bone marrow related diseases is S. dublin.

By way of example, live bacteria in accordance with aspects of the invention include known strains of S. enterica serovar Typhimurium (S. typhimurium) and S. enterica serovar Typhi (S. typhi) which are further modified as provided by the invention to form vectors for the prevention and/or treatment of neoplasia. Such Strains include Ty21a, CMV906, CMV908, CMV906-htr, CMV908-htr, Ty800, aroA-/serC-, holavax, M01ZH09, VNP20009. These strains contain defined mutations within specific serotypes of bacteria. The invention also includes the use of these same mutational combinations contained within alternate serotypes or strains in order to avoid immune reactions which may occur in subsequent administrations. In a preferred embodiment, S. Typhimurium, S. montevideo, and S. typhi which have non-overlapping O-antigen presentation (e.g., S. typhimurium is O-1, 4, 5, 12 and S. typhi is Vi, S. montevideo is O-6, 7) may be used. Thus, for example, S. typhimurium is a suitable serotype for a first injection and another serotype such as S. typhi or S. montevideo are used for a second injection and third injections. Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles.

Novel strains of Salmonella are also encompassed that are, for example, attenuated in virulence by mutations in a variety of metabolic and structural genes. The invention therefore may provide a live composition for treating cancer comprising a live attenuated bacterium that is a serovar of Salmonella enterica comprising an attenuating mutation in a genetic locus of the chromosome of said bacterium that attenuates virulence of said bacterium and wherein said attenuating mutation is a combinations of other known attenuating mutations. Other attenuating mutation useful in the Salmonella bacterial strains described herein may be in a genetic locus selected from the group consisting of phoP, phoQ, edt, cya, crp, poxA, rpoS, htrA, nuoG, pmi, pabA, pts, damA, met, cys, pur, purA, purB, purI, purF, leu, ilv, arg, lys, zwf, aroA, aroB, aroC, aroD, serC, gua, cadA, rfc, rjb, rfa, ompR, msbB, pfkAB, crr, glk, ptsG, ptsHl, manXYZ and combinations thereof. The strain may also contain a mutation known as "Suwwan", which is an approximately 100 kB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes tlyA, tlyC patI and pld from Rickettsia, whereby the bacteria exhibit enhanced invasion and/or escape from the phagolysosome (Witworth et al., 2005, Infect. Immun. 73: 6668-6673), thereby enhancing the activity of the effector genes described below. The strain may also be engineered to be deleted in an avirulence (anti-virulence) gene, such as .zirTS, grvA and/or pcgL, or express the E. coli lac repressor, which is also an avirulence gene in order to compensate for over-attenuation. The strain may also express SlyA, a known transcriptional activator. In a preferred embodiment, the Salmonella strains are msbB mutants (msbB-). In a more preferred embodiment, the strains are msbB- and Suwwan. In a more preferred embodiment the strains are msbB-, Suwwan and zwf-. Zwf has recently been shown to provide resistance to CO2, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). In a more preferred embodiment, the strains are msbB-, Suwwan, zwf- and trxA-. In a most preferred embodiment, the strains are msbB-, Suwwan, zwf-, trxA- and gor-.

The invention also encompasses according to a preferred embodiment, gram-positive bacteria. Preferred bacteria of the invention are group B Streptococcus including S. agalaciae, and Listeria species including L. monocytogenes. It is known to those skilled in the arts that minor variations in molecular biology techniques such as use of gram-positive origins of replication, gram-positive signal sequences gram-positive promoters (e.g., Lactococcus expression, Mohamadzadeh et al., PNAS Mar. 17, 2009 vol. 106 no. 11 4331-4336; Geertsma and Poolman, 2007, High-throughput cloning and expression in recalcitrant bacteria, Nature Methds 4: 705-707; Prudhomme et al., 2006, Antibiotic stress induces genetic transformability in the human pathogen Streptococcus pneumoniae, Science 313: 89-92; WO/2009/139985 Methods and materials for gastrointestinal delivery of a pathogentoxin binding agent; van Asseldonk, M et al. 1990, Cloning of usp45, a gene encoding a secreted protein from Lacotococcs lactis subsp. lactis MG1363 Gene 95, 15-160; Kim et al., J Appl Microbiol. 2008 June; 104(6):1636-43. Epub 2008 Feb. 19. Display of heterologous proteins on the surface of *Lactococcus lactis* using the H and W domain of PrtB from *Lactobacillus delburueckii* subsp. *bulgaricus* as an anchoring matrix; Lee et al., 1999, Characterization of *Enterococcus faecalis* alkaline phosphatase and use in identifying *Streptococcus agalactiae* secreted proteins, J. Bacteriol 181(18):5790-9.) are required and substituted as needed.

Mutational backgrounds of *Listeria* vectors include those previously isolated, including the delta-actA strain 142 (Wallecha et al., 2009, Construction and characterization of an attenuated *Listera monocytogenes* strain for clinical use in cancer immunotherapy, Clin Vaccine Immunol 16: 96-103), the double D-alanine (D-ala) strain described by Jiang et al., 2007, Vaccine 16: 7470-7479, Yoshimura et al., 2006, Cancer Research 66: 1096-1104, Lenz et al., 2008, Clinical and Vaccine Immunology 15: 1414-1419, Roberts et al., 2005, Definition of genetically distinct attenuation mechanisms in naturally virulent *Listeria* monotytogenes by comparative cell culture and molecular characterization, Appl. Environ. Microbiol 71: 3900-3910, the actA, prfA strain by Yan et al., Infect Immun 76: 3439-3450, and those described by Portnoy et al., EP1513924 and Portnoy et al., WO/2003/102168.

Mutational backgrounds of the group B *Streptococcus, S. agalactiae*, include wild type (no mutations), of any of the nine serotypes that depend on the immunologic reactivity of the polysaccharide capsule and among nine serotypes, preferably types Ia, Ib, II, III, and V capable of being invasive in humans. The strain may be deleted in the beta-heolysin/cytolysin (beta-H/C), including any member of the cly operon (clyXDGZAEFLJK SEQ ID NO:4), preferably the clyE gene, or the CspA protease associated with virulence (Shelver and Bryan, 2008, J Bacteriol. 136: 129-134), or the hyaluronate lyse C5a peptidase CAMP factor, oligopeptidase (Liu and Nizet 2004, Frontiers in Biosci 9: 1794-1802; Doran and Nizet 2004, Mol Microbiol 54: 23-31; Herbert et al., 2004, Curr Opin Infect Dis 17: 225-229). The strains may further have mutations in metabolic genes pur, purA, aroA, aroB, aroC, aroD, pgi (glucose-6-phosphate isomerase), fructose-1,6-bisphosphatase, ptsH, ptsI, and/or one or more amino acid transporters and/or amino acid permeases. In a preferred embodiment, the strain is clyE deficient.

Other bacterial strains are also encompassed, including non-pathogenic bacteria of the gut such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Shigella* sp., *Yersinia* sp., *Streptococcus* sp. and *Listeria* sp. Bacteria of low pathogenic potential to humans such as *Clostridium* spp. and attenuated *Clostridium* spp., *Proteus mirabilis*, insect pathogenic Xenorhabdus sp., *Photorhabdus* sp. and human wound *Photorhabdus* (Xenorhabdus) are also encompassed. Probiotic strains of bacteria are also encompassed, including *Lactobacillus* sp., *Lactococcus* sp., *Leuconostoc* sp., *Pediococcus* sp., *Streptococcus* sp., *Streptococcus agalactiae, Lactococcus* sp., *Bacillus* sp., *Bacillus* natto, *Bifidobacterium* sp., *Bacteroides* sp., and *Escherichia coli* such as the 1917 Nissel strain.

The invention also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of *Salmonella* sp), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced. Administration of the strain to the patient is therapeutic for the treatment of cancer.

The present invention provides, for example, and without limitation, live bacterial compositions that are genetically engineered to express one or more protease inhibitors combined with antitumor effector molecules for the treatment of cancers or neoplasias.

According to various embodiments, the invention provides pharmaceutical compositions comprising pharmaceutically acceptable carriers and one or more bacterial mutants. The invention also provides pharmaceutical compositions comprising pharmaceutically acceptable carriers and one or more bacterial mutants comprising nucleotide sequences encoding one or more therapeutic molecules. The pharmaceutical compositions of the invention may be used in accordance with the methods of the invention for the prophylaxis or treatment of neoplastic disease. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is chimeric toxin.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is a molecule with direct anti-cancer lytic capability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cancer cytotoxic or inhibitory ability.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cellular activity against other cells of a tumor, including neutrophils, macrophages, T-cells, stromal cells, endothelial cells (tumor vasculature) and/or cancer stem cells.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules co-expressed with a protease inhibitor.

In a specific embodiment, a pharmaceutical composition comprises a pharmaceutically acceptable carrier and one or more attenuated bacterial mutants, wherein the bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules, prodrug converting enzymes, metabolite degrading enzymes, lytic peptides, DNAases or anti-cancer peptides.

In a specific embodiment, a pharmaceutical composition comprises a pharmaceutically acceptable carrier and one or more attenuated bacterial mutants, wherein the bacterial mutants are a *Streptococcus* sp. In another specific embodiment, a pharmaceutical composition comprises a pharmaceutically acceptable carrier and one or more attenuated gram-positive bacterial mutants, wherein the attenuated gram-positive bacterial mutants are a *Streptococcus* sp., and the attenuated gram-positive bacterial mutants comprise one or more nucleic acid molecules encoding one or more therapeutic molecules, prodrug converting enzymes, metabolite degrading enzyme, lytic peptides, DNAases or anti-cancer peptides.

In a specific embodiment, a pharmaceutical composition comprises a pharmaceutically acceptable carrier and one or more attenuated bacterial mutants, wherein the bacterial mutants are a *Listeria* sp. In another specific embodiment, a pharmaceutical composition comprises a pharmaceutically acceptable carrier and one or more attenuated bacterial mutants, wherein the attenuated gram-positive bacterial mutants are a *Listeria* sp., and the attenuated gram-positive bacterial mutants comprise one or more nucleic acid molecules encoding one or more therapeutic molecules, prodrug converting enzymes, metabolite degrading enzyme, lytic peptides, DNAases or anti-cancer peptides.

The present invention encompasses treatment protocols that provide a better therapeutic effect than current existing anticancer therapies. In particular, the present invention provides methods for prophylaxis or treatment of neoplastic diseases in a subject comprising administering to said subject and one or more bacterial mutants. The present invention also provides methods for the prophylaxis or treatment of neoplastic diseases in a subject comprising administering to said subject one or more bacterial mutants, wherein said bacterial mutants comprise one or more nucleic acid molecules encoding one or more therapeutic molecules together with one or more protease inhibitors.

The methods of the present invention permit lower dosages and/or less frequent dosing of the bacterial mutants to be administered to a subject for prophylaxis or treatment of neoplastic disease to achieve a therapeutically effective amount of one or more therapeutic molecules. In a preferred embodiment, the genetically modified bacteria are used in animals, including humans, dogs, cats, and/or horses for protection or treatment against neoplastic diseases.

Accordingly, when administered to an individual, a live *Salmonella*, *Listeria* or *Streptococcus* bacterial vector or therapeutic, in accordance with the present invention, that is genetically engineered to express one or more anti-neoplastic disease molecules or molecules against other cells within the neoplastic milieu in combination with a protease inhibitor and have improved stability due to the presence of the protease inhibitor and result in anti-neoplastic activity.

5. DEFINITIONS

In order that the invention may be more fully understood, the following terms are defined.

As used herein, "attenuated", "attenuation", and similar terms refer to elimination or reduction of the natural virulence of a bacterium in a particular host organism, such as a mammal.

"Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium.

As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, inducible promoters (including tetracycline, arabinose, (EP1,655,370 A1, expressly incorporated in its entirety herein), salicylic acid, hypoxic, tumor cell specific inducible promoters) regulatory site (including transcriptional terminator sites, ribosome binding sites, transcriptional inhibitor binding sites, transcriptional activator binding sites), origin of replication, intercistronic region, and portions therein. It is understood that all protein expression constructs require a stop signal. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

Cassette, or expression cassette is used to describe a nucleic acid sequence comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter. The cassette may also contain a multiple cloning site (MCS) and transcriptional terminator within the 5' and 3' restriction endonuclease cleavage sites. The cassette may also contain cloned genes of interest.

As used herein, the term "*salmonella*" (plural, "salmonellae") and "*Salmonella*" refers to a bacterium that is a serovar of *Salmonella enterica*. A number of serovars of *S. enterica* are known. Particularly preferred *salmonella* bacteria useful in the invention are attenuated strains of *Salmonella enterica* serovar Typhimurium ("*S. typhimurium*") and serovar Typhi ("*S. typhi*") as described herein.

As used herein, the terms "strain" and "isolate" are synonymous and refer to a particular isolated bacterium and its genetically identical progeny. Actual examples of particular strains of bacteria developed or isolated by human effort are indicated herein by specific letter and numerical designations (e.g. strains Ty21a, CMV906, CMV908, CMV906-htr, CMV908-htr, Ty800, holavax, M01ZH09, VNP20009).

The definitions of other terms used herein are those understood and used by persons skilled in the art and/or will be evident to persons skilled in the art from usage in the text.

As used herein, the terms "homology" and "identity" are used interchangeably, but homology for proteins can include conservative amino acid changes. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer. Gribskov, M. and Devereux, J., eds., M Stockton Press, New York, 1991; Carillo et al. (1988) SIAM J Applied Math 48:1073).

As use herein, "sequence identity" refers to the number of identical amino acids (or nucleotide bases) in a comparison between a test and a reference polypeptide or polynucleotide. Homologous polypeptides refer to a pre-determined number of identical or homologous amino acid residues. Homology includes conservative amino acid substitutions as well identical residues. Sequence identity can be determined by standard alignment algorithm programs used with default gap penalties established by each supplier. Homologous nucleic acid molecules refer to a pre-determined number of identical or homologous nucleotides. Homology includes substitutions that do not change the encoded amino acid (i.e., "silent substitutions") as well identical residues. Substantially homologous nucleic acid molecules hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule. (For determination of homology of proteins, conservative amino acids can be aligned as well as identical amino acids; in this case, percentage of identity and percentage homology vary). Whether any two nucleic acid molecules have nucleotide sequences (or any two polypeptides have amino acid sequences) that are at least 80%, 85%, 90%, 95%, 96%, 97%, 98% or 99% "identical" can be determined using known computer algorithms such as the "FAST A" program, using for example, the default parameters as in Pearson et al. Proc. Natl. Acad. Sci. USA 85: 2444 (1988) (other programs include the GCG program package (Devereux, J., et al., Nucleic Acids Research 12(1): 387 (1984)), BLASTP, BLASTN, FASTA (Atschul, S. F., et al., J. Molec. Biol. 215:403 (1990); Guide to Huge Computers, Martin J. Bishop, ed., Academic Press, San Diego (1994), and Carillo et al. SIAM J Applied Math 48: 1073 (1988)). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. J. Mol. Biol. 48: 443 (1970), as revised by Smith and Waterman (Adv. Appl. Math. 2: 482 (1981)). Briefly, a GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al. Nucl. Acids Res. 14: 6745 (1986), as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polynucleotide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often without relying on software.

The phrase or term "substantially identical" or "homologous" or similar varies with the context as understood by those skilled in the relevant art and generally means at least 60% or 70%, preferably means at least 80%, more preferably at least 90%, and most preferably at least 95%, 96%, 97%, 98%, 99% or greater identity. As used herein, substantially identical to a product means sufficiently similar so that the property of interest is sufficiently unchanged so that the substantially identical product can be used in place of the product.

As used herein, Salmonella encompasses all Salmonella species, including: Salmonella typhi, Salmonella choleraesuis, and Salmonella enteritidis. Serotypes of Salmonella are also encompassed herein, for example, typhimurium, a subgroup of Salmonella enteritidis, commonly referred to as Salmonella typhimurium.

As used herein, the term "analog" refers to a polypeptide that possesses a similar or identical function as a primary or secondary effector molecule but does not necessarily comprise a similar or identical amino acid sequence of a primary or secondary effector molecule, or possess a similar or identical structure of a primary or secondary effector molecule. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least .sup.85%, at least 90%, at least 95% or at least 99% identical to the amino acid sequence of a primary or secondary effector molecule described herein; (b) a polypeptide encoded by a nucleotide sequence that hybridizes under stringent conditions to a nucleotide sequence encoding a primary or secondary effector molecule described herein of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 200 contiguous amino acid residues, at least 300 contiguous amino acid residues, at least 500 contiguous amino acid residues, or at least 1000 contiguous amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a primary or secondary effector molecule described herein. A polypeptide with similar structure to a primary or secondary effector molecule described herein refers to a polypeptide that has a similar secondary, tertiary or quaternary structure of primary or secondary effector molecule described herein. The structure of a polypeptide can be determined by methods known to those skilled in the art, including but not limited to, peptide sequencing, X-ray crystallography, nuclear magnetic resonance, circular dichroism, and crystallographic electron microscopy.

The phrase "anti-angiogenic factor" relates to any proteinaceous molecule which has anti-angiogenic activity, or a nucleic acid encoding such a proteinaceous molecule. In a preferred embodiment, the anti-angiogenic factor is a peptide fragment or cleavage fragment of a larger protein.

The term "attenuation" relates to a modification so that a microorganism or vector is less pathogenic. The end result of attenuation is that the risk of toxicity as well as other side-effects is decreased, when the microorganism or vector is administered to the patient.

The term "bacteriocin" relates to a bacterial proteinaceous toxin with selective activity, in that the bacterial host is immune to the toxin. Bacteriocins may be encoded by the bacterial host genome or by a plasmid, may be toxic to a broad or narrow range of other bacteria, and may have a simple structure comprising one or two subunits or may be a multi-subunit structure. In addition, a host expressing a bacteriocin has immunity against the bacteriocin. Bacteriocins include a number of bacterial antibiotics, including colicins and microcins.

The phrase "chelating agent sensitivity" is defined as the effective concentration at which bacteria proliferation is affected, or the concentration at which the viability of bacteria, as determined by recoverable colony forming units (c.f.u.), is reduced.

As used herein, the term "derivative" in the context of a "derivative of a polypeptide" refers to a polypeptide that comprises an amino acid sequence of a polypeptide, such as a primary or secondary effector molecule, which has been altered by the introduction of amino acid residue substitutions, deletions or additions, or by the covalent attachment of any type of molecule to the polypeptide.

The term "derivative" as used herein in the context of a "derivative of a primary or a secondary effector molecule" refers to a primary or secondary effector molecule which has been so modified, e.g., by the covalent attachment of any type of molecule to the primary or secondary molecule. For example, but not by way of limitation, a primary or secondary effector molecule may be modified, e.g., by proteolytic cleavage, linkage to a cellular ligand or other protein, etc. A derivative of a primary or secondary effector molecule may be modified by chemical modifications using techniques known to those of skill in the art (e.g., by acylation, phosphorylation, carboxylation, glycosylation, selenium modification and sulfation). Further, a derivative of a primary or secondary effector molecule may contain one or more non-classical amino acids. A polypeptide derivative possesses a similar or identical function as a primary or secondary effector molecule described herein.

The term "derivative" in the context of a "derivative of an msbB⁻ attenuated tumor-targeted Salmonella mutant" refers to a modified msbB Salmonella mutant as defined in International Publication No. WO 99/13053 at page 17, incorporated herein by reference in its entirety.

As used herein, the term "fragment" refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, at least contiguous 250 amino acid residues, at least contiguous 300 amino acid residues, at least contiguous 500 amino acid residues, or at least contiguous 1000 amino acid residues of the amino acid sequence of a primary or secondary effector molecule.

As used herein, the term "functional fragment" refers to a fragment of a primary or secondary effector molecule that retains at least one function of the primary or secondary effector molecule (e.g., enzymatic activity, anti-angiogenic activity, or anti-tumor activity of the effector molecule).

As used herein, the term "fusion protein" refers to a polypeptide that comprises an amino acid sequence of primary or secondary effector molecule, or functional fragment or derivative thereof, and an amino acid sequence of a heterologous polypeptide (e.g., a non-primary or non-secondary effector molecule).

As used herein, "purified" attenuated tumor-targeted bacterial strain is substantially free of contaminating proteins or amino acids (e.g., debris from dead bacteria), or media. An attenuated tumor-targeted bacterial strain that is substantially free of contaminating proteins or amino acids includes preparations of attenuated tumor-targeted bacteria having less than about 30%, 20%, 10%, or 5% (by dry weight) of contaminating protein or amino acid.

As used herein, a "release factor" includes any protein, or functional portion thereof which enhances release of bacterial components. In one embodiment a release factor is a bacteriocin release protein. Release factors include, but are not limited to, the bacteriocin release protein (BRP) encoded by the colicin D13 plasmid, the BRPs encoded by the colicin E1-E9 plasmids, or BRPs encoded by the colicin A, N or D plasmids.

"Septic shock" is a state of internal organ failure due to a complex cytokine cascade, initiated by TNF-α. The relative ability of a microorganism or vector to elicit TNF-α. is used as one measure to indicate its relative ability to induce septic shock.

"Tumor-targeted" is defined as the ability to preferentially localize to a cancerous or neoplastic target cell or tissue relative to a non-cancerous counterpart cell or tissue and replicate. Thus, a tumor-targeted bacteria such as *Salmonella* preferentially attaches to, infects and/or remains viable in the cancerous target cell or the tumor, carcinoma, lymphoma or leukemic bone marrow environment.

"Virulence" is a relative term describing the general ability to cause disease, including the ability to kill normal cells or the ability to elicit septic shock (see specific definition below).

As used herein, the strain designations VNP20009 (International Publication No. WO 99/13053), YS1646 and 41.2.9 are used interchangeably and each refer to the strain deposited with the American Type Culture Collection and assigned Accession No. 202165. As used herein, the strain designations YS1456 and 8.7 are used interchangeably and each refer to the strain deposited with the American Type Culture Collection and assigned Accession No. 202164.5.

6. DETAILED DESCRIPTION OF THE INVENTION

Figure 1A:
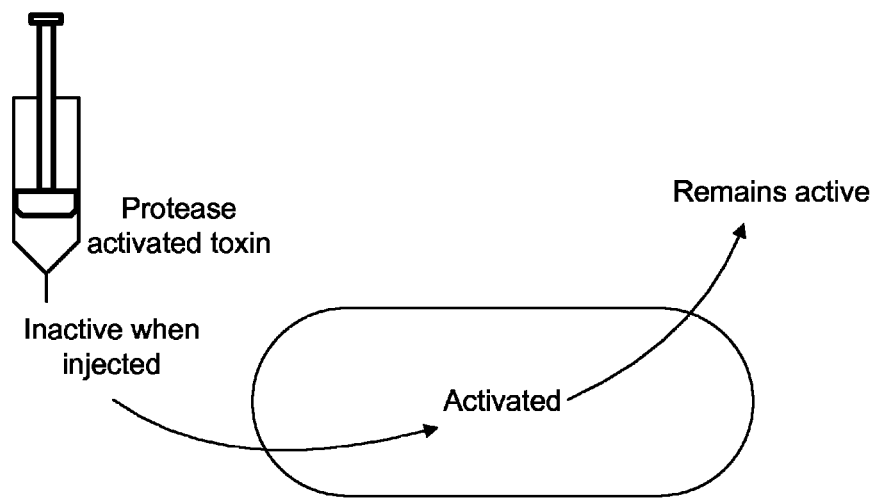
FIG. 1A shows a tumor-protease activated toxin and FIG. 1B shows a tumor protease inhibitor and protease sensitive toxin expression system.

The present invention provides, according to various embodiments, live attenuated therapeutic bacterial strains that express one or more therapeutic molecules together with one or more protease inhibitor polypeptides that inhibit local proteases that could deactivate the therapeutic molecules. In particular, one aspect of the invention relates to live attenuated tumor-targeted bacterial strains that may include *Salmonella, Streptococcus* or *Listeria* vectoring novel chimeric anti-tumor toxins to an individual to elicit a therapeutic response against cancer. The types of cancer may generally include solid tumors, carcinomas, leukemias, lymphomas and multiple myelomas. In addition, certain of the therapeutic molecules have co-transmission requirements that are genetically unlinked to the therapeutic molecule(s), limiting certain forms of genetic exchange, i.e., distal to rather than adjacent to). Another aspect of the invention relates to live attenuated tumor-targeted bacterial strains that may include *Salmonella, Streptococcus*, and *Listeria* that encode anti-neoplastic molecules to an individual to elicit a therapeutic response against cancers including cancer stem cells, immune infiltrating cells and or tumor matrix cells. The therapeutic agents also relates to reducing or eliminating the bacteria's ability to undergo conjugation, further limiting incoming and outgoing exchange of genetic material.

For reasons of clarity, the detailed description is divided into the following subsections: protease sensitivity; protease inhibitors; targeting ligands; lytic peptides; antibody deactivating proteins; chimeric bacterial toxins; expression of proteins without generating chimeras; limiting bacterial conjugation; expression of DNase, or colicin DNase as active extracellular enzymes; co-expression of protease inhibitors with bacterial toxins; co-expression of protease inhibitors with bacterial toxins; segregation of required colicin cofactors; characteristics of therapeutic bacteria.

6.1. Protease Sensitivity.

The therapeutic proteins of the invention are sensitive to extracellular proteases (in contrast pro-aerolysin or urokinase chimeric toxins that are activated by proteases). Proteases may be classified by several different systems, for example, into six groups: serine proteases, threonine proteases, cysteine proteases, aspartate proteases, metalloproteases and glutamic acid proteases. Alternatively, proteases may be classified by the optimal pH in which they are active: acid proteases, neutral proteases, and basic proteases (or alkaline proteases). Protease digestion sites may be added to the therapeutic agent to enhance protease sensitivity when coexpressed with a corresponding protease inhibitor as discussed below within the localized confines of the bacteria and its surroundings, e.g., within a solid tumor, carcinoma, lymphoma or leukemic bone marrow, the extracellular protease sensitive protein is protected from degradation whereas if it and its protective inhibitor leak outside the confines, the inhibitor falls below the level necessary to cause inhibition and the effector molecule is degraded. Preferred proteases for conferring greater sensitivity are those that are under-expressed in tumors and over-expressed in normal tissues. However, many proteases are over-expressed within tumors. Proteases for which sensitivity sights may be added and for which protease inhibitors may be co-expressed include but are not limited to those described by Edwards et al. (eds) 2008 (The Cancer Degradome: Proteases and Cancer Biology, Springer, 926 pp). as well as proteases of lysosomes and the gut such as tissue plasminogen activator, activated protein C, factor Xa, granzyme (A, B, M), cathepsins (e.g., cathepsin B and S), thrombin, plasmin, urokinase, matrix metaloproteaes (types 1-28) membrane matrix metalloproteases (types 1-4), prostate specific antigens (PSA; kallikrein 3-related peptidase), kallikrein 2, elastin, trypsin, chymotrypsin. A variety of protease assays are known to those skilled in the arts. Many protease assays are commercially available, such as the QuantiCleave Fluorescent Protease Assay Kit, and QuantiCleave Protease Assay Kit II (Thermo/Fisher, Rockford, Ill.), Protease Assay Kit (G Biosciences, Maryland Heights, Mo.), PepTag Protease Assay (Promega, Madison, Wis.; 1993 Promega Notes Magazine 44: 2), Viral Protease Assay Kits (AnaSpec, Fremont, Calif.), Protease Assay Kit from Calbiochem (Calbiochem, San Diego, Calif.). Standard laboratory techniques to measure protease activity, and thus the reduced activity of protease inhibitors, include densiometric, spectrophotometric, colorimetric and fluorometric assays, sodium dodecyl sulfate (SDS) polyacrylamide gel electrophoresis (PAGE), two dimensional SDS-PAGE, high pressure liquid chromatography (HPLC) and mass spectroscopy (mass-spec). High sensitivity methods have also been described US Patent Pub. 2009/0294288.

Protease sensitivity may be enhance either by the complete addition of protease cleavage sites, or minor alteration of the amino acid sequence by making amino acid changes that are "conservative" or "tolerated", resulting in addition or enhancement of a cleavage site. Determination of conservative or tolerated amino acids is generally known to those skilled in the arts by their chemistry, whereby amino acids are grouped into hydrophilic [ala, pro, gly, glu, asp, gln, asn, ser, thr], sulfhydryl [cys], aliphatic [val, ile, leu, met], basic [lys, arg, his], and aromatic [phe, tyr, trp] (French and Robson, What is a conservative substitution? J. Mol. Evol. 19: 171-175), but may also be determined by methods such as SIFT (Ng and Henikoff 2003, SIFT: predicting amino acids changes that affect protein function, Nucleic Acids Research 31: 3812-3814; Kumar et al., 2009, Predicting the effects of coding non-synonymous variants on protein function using the SIFT algorithm, Nat Protoc 4: 1073-1081; Altschul 1991, Amino acid substitutions matrices from an information theoretic perspective, Journal of Molecular Biology 219: 555-665; Henikoff and Henikoff, 1992, Amino acid substitution matrices from protein blocks, Proceedings of the National Academy of Sciences USA 89: 10915-10919). PAM (percent absent mutations), PMB (probability matrix from blocks) and BLOSUM (blocks of amino acid substitution matrix) matrices are well known and may be used. Addition of cleavage sites by minor sequence alteration is conducted preferably in knowledge of the protein 3 dimensional crystal structure, and/or based on multiple sequence alignments that establish protein domains and variable regions between domains such that it is understood that those changes in the amino acid sequence might normally occur and/or be tolerated, in addition to SIFT or other analyses. Protein domain information is used to select interdomain regions. 3D information is also used to select regions of the protein that are exposed externally, and thus more sensitive to proteases. For example, the crystal structure of a number of colicins are known (e.g., colicin E3, Soelaiman et al., 2001, Molecular Cell 8: 1053-1062). Colicins have also been the subject of multiple sequence alignments (e.g., FIG. 18.2 in Sharma et al., Chapter 18 in Kastin (ed), 2006, Handbook of Biologically Active Peptides, Academic Press), and distinct protein domains have been established which correlate with the crystal structure (Sharma et al., 2006, Handbook of Biologically Active Peptides, Chapter 18, Colicins: Bacterial/Antibiotic Peptides, pp 115-123). In colicin E3, there are 3 domains, an N-terminal "T", or translocation domain, an internal "R" or receptor domain, and C-terminal "C" or catalytic domain. Examination of the "hinge" sequence between domains R and C of colE3, amino acids 451 to 456 (NKPRKG SEQ ID NO:147), shows that these amino acids are variable compared to other homologous colicins such as colE7 (KRNKPG SEQ ID NO:148), colE2 (KRNKPG SEQ ID NO:148) and are thus identified as candidates for sequence alteration. For example, a furin cleavage sequence (designated R/–/Kr/R⁺s/–/–/–; also designated RXKR↓SX SEQ ID NO:149 can be added by conservative changes. Thus for example, the sequence NKPRGK SEQ ID NO:150 within colE3 can be conservatively changed to NKPRKs SEQ ID NO:151 which adds weak furin site, and further modified conservatively to NrPRKs SEQ ID NO:152 which results in a strong furin site, which, using the ProP algorithm (e.g., ProP 1.0, Duckert et al., 2004, Prediction of proprotein convertase cleavage sites, Protein Engineering Design and Selection 17: 107-122) is predicted to be cleaved by furin. Biochemical confirmation can be conducted by standard techniques such as 1D and 2D SDS-PAGE gel electrophoresis on the secreted proteins in the media in the presence of furin.

Protease cleavage sites are defined in the Merops database (Rawlings et al., 2010, MEROPS: The Peptidase Database, Nucleic Acids Res. 2010 (Database issue):D227-33. It will be understood to those skilled in the arts that many proteases do not have strict sequence recognition sites, but rather have sequence preferences and/or frequencies. The MEROPS site depicts the preferences with a weighted pictogram and a table which lists frequencies of occurrence within a cleavage sequence. The table a non-limiting list proteases of tumors, the MEROPS sequence specification, and a simplified representative of an amino acid one letter code recognition sequence (where X is any amino acid) and the cleavage signal is given by a downward arrow) is presented in Table 2.

TABLE 2

Examples of protease cleavage sequences usable to guide protease sensitivity modifiction of effector proteins.

| Protease | MEROPS Sequence Designation | Simplified Representative Sequence Designation |
| --- | --- | --- |
| Factor Xa | ia/e/Gfp/R⁺sti/vfs/–/g | (IEGR↓SV) SEQ ID NO:153 |
| Furin | R/–/Kr/R⁺s/–/–/– | (RXKR↓SX) SEQ ID NO:154 |
| Plasminogen activator | –/–/–/R⁺R/iv/N/– | (XXR↓RIN) SEQ ID NO:155 |
| Urokinase | –/sg/Gs/Rk⁺–/r/–/– | (XSGR↓XR) SEQ ID NO:156 |
| MMP1 | –/pa/g⁺li/–/–/– | (GPXG↓LXG) SEQ ID NO:157 |

TABLE 2-continued

| Examples of protease cleavage sequences usable to guide protease sensitivity modifiction of effector proteins. | | |
|---|---|---|
| Protease | MEROPS Sequence Designation | Simplified Representative Sequence Designation |
| MMP8 | g/Pas/-/g$^{+}$1/-/g/- | (GPQG↓LRG) SEQ ID NO:158 |
| MMP 13 | g/P/-/g$^{+}$1/-/ga/- | (GPPG↓LXG) SEQ ID NO:159 |
| Membrane matrix metallo-protease 1 | -/p/-/-$^{+}$1/-/-/- | (LPAG↓LVLX) SEQ ID NO:160 |
| PSA | si/sq/-/yq$^{+}$s/s/-/- | (SSQY↓SSN) SEQ ID NO:161 |
| Kallikrein 2 | g/-/-/R$^{+}$-/-/-/gs | (GGLR↓SGGG) SEQ ID NO:162 |
| Granzyme A | t/-/-/RK$^{+}$sa/-/-/- | (TXXPR↓SX) SEQ ID NO:163 |
| Granzyme B | v/-/-/D$^{+}$-/-/-/- | (VEXD↓SX) SEQ ID NO:164 |
| Granzyme M | Ka/vaye/Pa/LM$^{+}$-/-/-/- | (KVPL↓X) SEQ ID NO:165 |
| Cathepsin B | -/-/l/r$^{+}$-/-/g/- | (XLR↓XXGG) SEQ ID NO:166 |
| Cathepsin S | -/-/flv/r$^{+}$-/-/-/- | (SGFR↓SXG) SEQ ID NO:167 |
| Thrombin | -/-/pla/R$^{+}$sag/-/-/- | (AGPR↓SLX) SEQ ID NO:168 |
| Plasmin | -/-/-/KR$^{+}$-/-/-/- | (AXLK↓SX) SEQ ID NO:169 |
| Plasminogen | /-/-/KR$^{+}$-/-/-/- | (AXLK↓SX) SEQ ID NO:170 |

The MEROPS database can be used to identify which proteases to inhibit, by analysis of a particular effector protein and the cleavage sites it contains. Comparison with the target tissue, eg Edwards et al. (eds) 2008, The Cancer Degradome: Proteases and Cancer Biology, Springer, 926 pp is also used to inform the choice. Alternatively, 2-dimensional gel electrophoresis and protein sequencing of radio-labeled peptides incubated with the target tumor can be used to identify which aminoacids are being cleaved in a therapeutic protein, and therefore which protease inhibitors to use.

6.2 Protease inhibitors

Protease inhibitors of the invention are preferably based on known polypeptide inhibitors. The inhibitors include both synthetic peptides and naturally occurring, endogenous peptides. Classes of protease inhibitors include: cysteine protease inhibitors, serine protease inhibitors (serpins), trypsin inhibitors, Kunitz STI protease inhibitor, threonine protease inhibitors, aspartic protease inhibitors, metalloprotease inhibitors. Protease inhibitors can also be classified by mechanism of action as suicide inhibitors, transition state inhibitors, protein protease inhibitor (see serpins) and chelating agents. The protease inhibitors of the invention are protein or polypeptide inhibitors encoded by DNA contained within the bacteria.

To result in the desired activity, the peptides should be surface displayed, released or secreted outside of the bacteria. Accordingly, the peptides are modified by fusing them to secretion signals. The secretion signals may be either N-terminal (LPP:OmpA, M13pIII, M13pVIII, zirS (Finlay et al., 2008, PLoS Pathogens 4 (4), e100003), heat-stable (ST; thermostable) toxins from *Escherichia* and *Vibrio* (U.S. Pat. No. 5,399,490), *E. coli* enterotoxin II (Kwon et al., U.S. Pat. No. 6,605,697), or by colicin fusions together with colicin lysis proteins, or using autotransporter fusions, fusion to the M13 pIX may also be used (WO 2009/086116). or hlyA C-terminal signal sequence last 60 amino acids of the *E. coli* HlyA hemolysin, together with the required HlyBD supplied in trans and endogenous tolC as shown in FIG. 2. The N-terminal signal sequences are well known and characterized by the presence of a protease cleavage site for an endogenous bacterial protease. Thus, N-terminal signal sequences provide free protease inhibitors, free from the signal sequence. The C-terminal signal sequence may be further engineered to have a protease cleavage site in between the protease inhibitory peptide and the signal sequence. The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Proteases upregulated within tumors for which protease cleavage sites may be engineered include: tissue plasminogen activator, activated protein C, factor Xa, granzyme (A, B, M), cathepsin, thrombin, plasmin, urokinase, matrix metaloproteaes, prostate specific antigen (PSA) and kallikrein 2 (e.g., Edwards et al. (eds) 2008, The Cancer Degradome: Proteases and Cancer Biology, Springer, 926 pp), as well as proteases of lysosomes and the gut.

Protease inhibitors have been reviewed by Laskowski and Kato, 1980, (Annual Review of Biochemistry 49: 593-626), expressly incorporated by reference herein. Serine proteases inhibitors, the largest group, include 1) bovine pancreatic trypsin inhibitor (Kunitz) family, 2) pancreatic secretory trypsin inhibitor (Kazal) family, 3) *Streptomyces* subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) *Ascaris* trypsin inhibitor family, and 9) others. Protease inhibitors have also been grouped within the MEROPS peptidase database (Rawlings et al., 2008 Nucleic Acids Res. 36 Database issue, D320-325).

Specific examples of protease inhibitors that may be expressed as complete proteins or peptide fragments corresponding to the active inhibitory site include but are not limited to aprotinin, autodisplay aprotinin (Jose J, Zangen D (2005) Autodisplay of the protease inhibitor aprotinin in *Escherichia coli*. Biochem Biophys Res Commun 333:1218-1226; Jose, 2006, Autodisplay: efficient bacterial surface display of recombinant proteins, Appl Microbiol Biotechnol 69: 607-614). cathepsin inhibitor peptide sc-3130*, Neisseria* protease inhibitor, lymphocyte protease inhibitor, maspin, matrix metalloprotease inhibitors, macroglobulins, antithrombin, equistatin, Bowman-Kirk inhibitor family, ovomucoid, ovoinhibitor-proteinase inhibitors from avian serum, dog submandibular inhibitors, inter-α-trypsin inhibitors from mammalian serum, chelonianin from turtle egg white, soybean trypsin inhibitor (Kunitz), secretory trypsin inhibitors (Kazal) $a_i$-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris* trypsin and pepsin inhibitors, lipocalins, CI inhibitor, plasminogen-activator inhibitor, collegenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports 37: 37-44). Fusion to glutathione-S transferase (GST) and co-expression with disulfide bond isomerase (DsbA) or nusA (Harrison 2000, Expression of soluble heterologous proteins via fusion with NusA protein. *inNovations* 11: 4-7) are also known to improve solubility. Methods to isolate novel protease inhibitors using M13 phage display have been described by Roberts et al., 1992 (Gene 121: 9-15). Examples of the peptide sequences of short peptide inhibitors is shown in Table 3.

TABLE 3

Sequences of short peptide protease inhibitors

| Protease Inhibitor | Protease(s) inhibited | Protein/Peptide Name and/or Peptide Sequence |
|---|---|---|
| Leupeptin | calpain, plasmin, trypsin, papain, and cathepsin B | Leupeptin |
| Aprotinin | Trypsin Plasmin Tissue kallikrei | RPDFC LEPPY TGPCK ARIIR YFYNA KAGLC QTFVY GGCRA KRNNF KSAED CMRTC GGA SEQ ID NO:5 Jose J, Zangen D (2005) Autodisplay of the protease inhibitor aprotinin in Escherichia coli. Biochem Biophys Res Commun 333:1218-1226 |
| Aprotinin homologues | Variable | Brinkmann et al, 1991 Eur J. Biochem 202: 95-99 |
| Protease Inhibitor 15 | Trypsin | Synthetic peptide: CFPGVTSNYLYWFK SEQ ID NO:6, corresponding to amino acids 245-258 of human protease inhibitor. |
| Tissue protease inhibitor | Serine protease inhibitor, Kazal type 1, mature | DSLGREAKCYNELNGCTKIYDPVCGTDGNTYPNECVL CFENRKRQTSILIQKSGPC SEQ ID NO:7 |
| Furin inhibitors | Furin | PAAATVTKKVAKSPKKAKAAKPKKAAKSAAKAVKPK SEQ ID NO:8<br>TKKVAKRPRAKRAA     SEQ ID NO:9<br>TKKVAKRPRAKRDL     SEQ ID NO:10<br>GKRPRAKRA     SEQ ID NO:11<br>CKRPRAKRDL     SEQ ID NO:12<br>CVAKRPRAKRDL     SEQ ID NO:13<br>CKKVAKRPRAKRDL     SEQ ID NO:14<br>RRRRRR L6R (hexa-L-arginine)     SEQ ID NO:15 |
| Kallikrein Inhibitors | Kallikrein 2 | SRFKVWWAAG     SEQ ID NO:16<br>AARRPFPAPS     SEQ ID NO:17<br>PARRPFPVTA     SEQ ID NO:18 |
| Pepsinogen 1-16 | Pepsin | LVKVPLVRKKSLRQNL     SEQ ID NO:19<br>Dunn et al., 1983 Biochem J 209: 355-362 |
| Pepsinogen 1-12 | Pepsin | LVKVPLVRKKSL     SEQ ID NO:20<br>Dunn et al., 1983 Biochem J 209: 355-362 |
| Pepsinogen 1-12 4-7 substitution | Pepsin | LVKGGLVRKKSL (II) [Gly4,5]     SEQ ID NO:21<br>LVKVPGGRKKSL (III) [Gly6,7]     SEQ ID NO:22<br>LVKGGGGRKKSL (IV) [Gly4-7]     SEQ ID NO:23<br>Dunn et al., 1983 Biochem J 209: 355-362 |
| Sunflower trypsin inhibitor SFTI-1 | Trypsin | GRCTKSIPPICFPD     SEQ ID NO:24 |
| Odorrana trypsin inhibitor | Trypsin | AVNIPFKVHFRCKAAFC SEQ ID NO:25 |
| Ascaris chymotrypsin elastase inhibitor | Chymtrypsin Elastase | GQESCGPNEV WTECTGCEMK CGPDENTPCP LMCRRPSCEC SPGRGMRRTN DGKCIPASQCP SEQ ID NO:26 |
| Ascaris trypsin inhibitor | Trypsin | EAEKCBZZPG WTKGGCETCG CAQKIVPCTR ETKPNPQCPR KQCCIASAGF VRDAQGNCIK FEDCPK SEQ ID NO:27 |
| Ascaris trypsin inhibitor | Trypsin | EAEKCTKPNE QWTKCGGCEG TCAQKIVPCT RECKPPRCEC IASAGFVRDA QGNCIKFEDC PK SEQ ID NO:28 |
| Onion trypsin inhibitor | Trypsin | MKAALVIFLL IAMLGVLAAE AYPNLRQVVV TGDEEEGGCC DSCGSCDRRA PDLARCECRD VVTSCGPGCK RCEEADLDLN PPRYVCKDMS FHSCQTRCSI L SEQ ID NO:29 |
| Barley chymotrypsin inhibitor 2 | Chymotrypsin | MSSMEKKPEGVNIGAGDRQNQKTEWPELVGKSVEEA KKVILQDK PAAQIIVLPVGTIVTMEYRIDRVRLFVDRLDNIAQVPRV G SEQ ID NO:30 |

TABLE 3-continued

Sequences of short peptide protease inhibitors

| Protease Inhibitor | Protease(s) inhibited | Protein/Peptide Name and/or Peptide Sequence |
|---|---|---|
| Thrombin inhibitors | Thrombin | IQPR    SEQ ID NO:31<br>GSAVPR    SEQ ID NO:32<br>Feng et al., (WO 2004/076484) PEPTIDE INHIBITORS OF THROMBIN AS POTENT ANTICOAGULANTS) |
| Tumor cell and endothelial cell migration inhibitor | Gelatinase | CTTHWGFTLC    SEQ IN NO:111<br>Li et al., 2006. Molecular addresses of tumors: selection by in vivo phage display. Arch Immunol Ther Exp 54: 177-181 |
| Proteosome inhibitors Chymostatin Clasto-tactastatin | Proteosome subunit 3 'chymotryptic-like' (beta5), 'tryptic-like' (beta2) and 'peptidyl-glutamyl peptide hydrolyzing' (beta1). | |
| Urokinase, thrombin, plasmin and trypsin inhibitors | Urokinase, thrombin, plasmin and trypsin | Markowska et al., 2008, Effect of tripeptides on the amindolytic activities of urokinase, thrombin, plasmin and trypsin. Int. J. Peptide Research and Therapeutics 14: 215-218. |

6.3 Targeting Ligands

Targeting ligands have specificity for the target cell and are used to both confer specificity to chimeric proteins, and to direct attachment and/or internalization into the target cell. The ligands are known ligands or may be novel ligands isolated through standard means such as phage display (Barbass III et al., 2004, Phage Display, A Laboratory Manual, Cold Spring Harbor Press) including the use of commercially available kits (Ph.D-7 Phage Display Library Kit, New England Biolabs, Ipswich, Mass.; Li et al., 2006. Molecular addresses of tumors: selection by in vivo phage display. Arch Immunol Ther Exp 54: 177-181,). The ligands of various aspects of the present invention are peptides that can be expressed as fusions with other bacterially-expressed proteins. The peptides may be further modified, as for gastrin and bombisin, in being amidated by a peptidylglycine-alpha-amidating monoxygenase or C-terminal amidating enzyme, which is co-expressed in the bacteria that use these peptides using standard molecular genetic techniques. Examples of targeting peptides are shown in Table 4.

TABLE 4

Examples of targeting peptides

| Peptide sequence or ligand name | Receptor Target | Reference |
|---|---|---|
| MNSDSECPLSHDGYCLHDGVCMYIEA<br>LDKYACNCVVGYIGERCQYRDLKWW<br>ELR<br>SEQ ID NO:172 | EGFR | |
| ERRP<br>Epidermal growth factor receptor related peptide | | Marciniak et al., 2004, Molecular Cancer Therapeutics 3: 1615-1621<br>Wu et al., 1989, J. Biol. Chem 246: 17469-17475.<br>Marciniak et al., 2003, Gastroenterology 124: 1337-1347. |
| TGF-alpha | EGFR | Schmidt and Wells 2002, Replacement of N-terminal portions of TGF-alpha with corresponding heregulin sequences affects ligand-induced receptor signalling and intoxication of tumor cells by chimeric growth-factor toxins. In. J. Cancer 97: 349-356. |

TABLE 4-continued

Examples of targeting peptides

| Peptide sequence or ligand name | Receptor Target | Reference |
|---|---|---|
| SYAVALSCQCALCRR CG-beta SEQ ID NO:33 | | Rivero-Muller et al., Moleclar and Cellular Endocrinology 2007: 17-25 Morbeck et al., 1993 |
| HAVDI and INPISGQ and dimeric versions | N-cadherin prostate | Williams et al., 2002, Journal of Biological Chemistry 277: 4361-4367. |
| laminin-411 binding peptides | Brain neovasculature | Ding et al., (2010) Proc. Natl. Acad. Sci. U. S. A. 107:18143-18148 |
| Pertussis toxin S3 subunit | cancer cells | |
| Peptides described by Li et al., 2006. Molecular addresses of tumors: selection by in vivo phage display. Arch Immunol Ther Exp 54: 177-181 | Tumor vasculature, VEGF-R (Flt-1), VCAM, EphA2, Aminopeptidase | Li et al., 2006. Molecular addresses of tumors: selection by in vivo phage display. Arch Immunol Ther Exp 54: 177-181 |
| DUP-1 peptide FRPNRAQDYNTN SEQ ID NO:173 | Prostate cancer | Zitzmann et al., Clinical Cancer Research January 2005 11; 139 |
| DARPins SEQ ID NO:34 | HER2 | Stumpp and Amstutz 2007, DARPins: a true alternative to antibodies, Curr Opin Drug Discov Devel. 10:153-159. |
| AVALSCQCALCRR CG-beta (ala truncation) SEQ ID NO:35 | | Jia et al., Journal of Pharmacy and Pharmacology 2008; 60: 1441-1448 |
| Leuteinizing hormone-releasing hormone (LHRH) pyroGlu-His-Trp-Ser-Tyr-Gly-Leu-Arg-Pro-Gly CONH2 SEQ ID NO:36 | LHRH receptor | |
| IL2 | IL2R | Frankel et al. 2000, Clinical Cancer Research 6: 326-334. |
| Tf | TfR | Frankel et al. 2000, Clinical Cancer Research 6: 326-334. |
| IL4 | IL4R | Frankel et al. 2000, Clinical Cancer Research 6: 326-334. |
| IL13 | IL13R | Kawakami et al., 2002, J. Immunol., 169: 7119-7126 |
| GM-CSF | GM-CSFR | Frankel et al. 2000, Clinical Cancer Research 6: 326-334. |
| CAYHRLRRC SEQ ID NO:174 Lymph node homing Cys-Ala-Tyr and cell penetrating Arg-Leu-Arg-Arg, proceeds thorugh macripinocytosis | Lymphnode homing and cell penetrating | Nishimura et al., 2008 JBC 283: 11752-11762 |
| A33 antigen-binding peptide | A33 | U.S. Pat. No. 5,712,369 Specific antibodies and antibody fragments |
| CLTA-4 (CD152) | Melanoma | U.S. Pat. No. 6,207,156 |
| CD19 binding peptides 12-mer peptide (Bpep) | specific for alpha(v) beta(6) integrin (αvβ6) non-Hodgkin lymphoma, chronic lymphocytic leukemia (CLL) and acute lymphocytic leukemia (ALL) | Pamejer et al., 2007, Cancer Gene Therapy 14: 91-97. |
| CD20 binding peptides | CD-20; B-cell malignancies | WO/2004/103404 Watkins et al. "CD-20 binding molecules" |
| CD22 binding peptides | B lymphocytes; hairy cell leukemia | Pearson et al. Int. J. Peptide Research and Therapeutics 14: 237-246. |

TABLE 4-continued

Examples of targeting peptides

| Peptide sequence or ligand name | Receptor Target | Reference |
| --- | --- | --- |
| CD25 binding peptides | Chemotherapy-resistant human leukemia stem cells. | Saito et al., 2010, Science Translational Medicine 2: 17ra9; Jordan Sci Transl Med 12 May 2010 2:31ps21 |
| TRU-015 | CD-20 | Hayden-Ledbetter et al., 2009 Clin Cancer Res 15: 2739-2746; Burge et al.. 2008, Clin Ther. 30:1806-16. |
| CD30 binding peptides | CD-30 Hodgkin lymphoma | |
| CD32 binding peptides | Chemotherapy-resistant human leukemia stem cells. | Saito et al., 2010, Science Translational Medicine 2: 17ra9; Jordan Sci Transl Med 12 May 2010 2:31ps21 |
| CD33 binding peptides | CD-33 AML Myelodysplastic cells (MDS) | |
| CD37 bnding peptides | Leukemia and lymphoma | |
| CD40 binding peptides | CD40 Multiple myeloma, non-Hodgkin lymphoma, chronic lymphocytic leukemia (CLL), Hodgkin lymphocytic and acute lymphoblastic leukemia (ALL), diffuse large B-cell lymphome, refractory non-Hodgkin Lymphoma, including follicular lymphoma | |
| CD52 binding peptides | CLL | |
| CD55 binding peptides | | |
| CD70 binding peptides | Hematological malignancies, Non-Hodgkin's lymphoma Also, killing activated T and B immune cells that would eliminate the bacterial vector | |
| CD123 binding peptides | AML | |
| RGD-containing peptides e.g., GRDGS SEQ ID NO:132, ACDCRGDCFCG (RGD4C) SEQ ID NO:174 | | De Villiers et al., 2008, Nanotechnology in drug delivery, Springer. |
| Nanobodies derived from camels and llamas (camelids), including humanized nanobodies and VHH recognition domains | Cancer | Rothbauer, et al. 2006. Nat. Methods 3: 887-889; Kirchhoferet al. 2010. Nat. Struct. Mol. Biol. 17:133-138 |
| Bombesin | Gastrin releasing peptide receptor | Dyba et al., 2004 Current Pharmaceutical Design 10: 2311-2334 |
| Gastrin releasing peptide | Gastrin releasing peptide receptor | |
| somatostatin octapeptide RC-121 (D-Phe-Cys-Tyr-D-Trp-Lys-Val-Cys-Thr-NH2 SEQ ID NO:37 | | |
| somatostatin | | |
| Vasoactive intestinal peptide (VIP Neurotensin) | | |

TABLE 4-continued

Examples of targeting peptides

| Peptide sequence or ligand name | Receptor Target | Reference |
|---|---|---|
| Parathyroid hormone-related protein PTHrP N-terminal 36 residues also has nuclear targeting | Parathyroid hormone receptor G-protein coupled receptor | |
| KLAKLAKKLALKLA SEQ ID NO:38 | Proapoptotic peptide | |
| EGFR binding peptides | EGFR | |
| Mesothelin binding peptides | Mesothelin | |
| Heat stable enterotoxin (ST) NSSNYCCELCCNPACTGCY Mature peptide SEQ ID NO:39 | Guanylyl cyclase C | |
| VLSFSPFAQD AKPVESSKEK ITLESKKCNI AKKSNKSDPE SMNSSNYCCE LCCNPACTGC SEQ ID NO:40 | Heat stable enterotoxin unprocessed | Sieckman et al., WO/2003/072125 |
| CM-CSF | AML Alfa(V)Beta(3) integrin STEAP-1 (six transmembrane antigen of the prostate) | |
| CDCRGDCFC SEQ ID NO:41 | RGD 4C: active peptide targeting the ᵥβ₃ integrin) | Line et al. 46 (9): 1552. (2005) Journal of Nuclear Medicine |
| LGPQGPPHLVADPSKKQGP WLEEEEAYGWMDF (gastrin-34) or big gastrin SEQ ID NO:42 | bind to the gastrin receptor, also known in the art as the cholecystokinin B (CCKB) receptor | |
| MGWMDF N-terminal truncation of gastrin SEQ ID NO:43 | | |
| VPLPAGGGTVLTKM SEQ ID NO:44 | Gastrin releasing peptide | |
| YPRGNHWAVGHLM SEQ ID NO:45 | | |
| CAYHLRRC SEQ ID NO:46 | AML | Nishimra et al., 2008. J Biol Chem 283: 11752-11762 |
| CAY (cys-ala-tyr) SEQ ID NO:47 | Lymph node homing | Nishimra et al., 2008. J Biol Chem 283: 11752-11762 |
| RLRR (arg-leu-arg-arg) SEQ ID NO:48 | Cell penetrating | Nishimra et al., 2008. J Biol Chem 283: 11752-11762 |
| VRPMPLQ SEQ ID NO:49 | Colonic dysplasia | Hsi u ng et al, Natre Medicin 14: 454-458 |
| HVGGSSV SEQ ID NO:50 | 2622 Radiation-Induced Expression of Tax-Interacting Protein 1 (TIP-1) in Tumor Vasculature Binds irradiated tumors i.e., ones responding to therapy | International Journal of Radiation OncologyBiologyPhysics, Volume 66, Issue 3, Pages S555-S556 H. Wang, A. Fu, Z. Han, D. Hallahan |
| CGFECVRQCPERC SEQ ID NO:171 | Lung vasculature - MOSE Binds membrane dipeptidase (MDP) | Mori 2004, Current Pharmaceutical Design 10: 2335-2343 |
| SMSIARL SEQ ID NO:51 | MURINE PROSTATE VASCULATURE | Mori 2004, Current Pharmaceutical Design 10: 2335-2343 |
| VSFLEYR SEQ ID NO:52 | MURINE PROSTATE VASCULATURE | Mori 2004 Current Pharmaceutical Design 10: 2335-2343 |
| Fragment 3 of the high mobility group (HMG)N2 CKDEPQRRSARLSAKPAPP KPEPKPKKAPAKK SEQ ID NO:53 | | |

TABLE 4-continued

Examples of targeting peptides

| Peptide sequence or ligand name | Receptor Target | Reference |
|---|---|---|
| H-VEPNCDIHVMW EWECFERL-NH2 SEQ ID NO:54 | VEGF BINDING PEPTIDE | (WO/2006/116545) SPATIAL CONTROL OF SIGNAL TRANSDUCTION |
| RLLDTNRPLLPY SEQ ID NO:55 | L-PEPTIDE Nasopharyngeal Phage derived - causes internalization of phage | Let al., 2004. Cancer Research 64: 8002-8008. |
| RGDLATL truncated RGDLATLRQLAQEDGVVGVR SEQ ID NO:56 | Alfa(v) beta (6) integrin | Shunzi et al. (Kathyll C Brown |
| HAIYPRH SEQ ID NO:57 and THRPPMWSPVWP SEQ ID NO:58 | Transferrin | U.S. Pat. No. 6,743,893 |
| Peptide 1 CKASQSVTNDVAC (CDR1) SEQ ID NO:59 Peptide 2 CYASNRYTC (CDR2) SEQ ID NO:60 Peptide 3 CQQDYRSPLTFC (CDR3) SEQ ID NO:61 Peptide 4 CSDYGVNWVC (CDR1) SEQ ID NO:62 Peptide 5 CLGIIWGDGRTDYNSALKSRC (CDR2) SEQ ID NO:63 | CD-22 | Pearson et al., 2008, Int J Pept Res Ther (2008) 14:237-246 |
| Cancer stem cell targeting peptides | Cancer stem cells | Cripe et al., 2009, Molecular Therapy (2009) 17 10,1677-1682 Short and Curiel 2009, Molecular Cancer Therapeutics 8: 2096-2102 |
| Chronic Lymphocytic leukemia binding peptides | CLL | Takahashi et al., Cancer Research 63: 5213-5217 |
| LTVXPWY SEQ ID NO:64 | Breast cancer | Shadidi and Sioudm 2003, The FASEB Journal 17: 256-258 |
| Leukemia binding peptides | Leukemia | Fairlie et al., 2003, Biochemistry 42: 13193-13202 Jaalouk et al., WO/2006/010070 "Compositions and methods related to peptides that selectively bind leukemia cells" Adebahr et al., |
| CPLDIDFYC SEQ ID NO:65 | AML | Jager et al., Leukemia 21: 411-420 |
| Lymphoma binding peptides | Lymphoma | Lam and Zhao, 1997 Targeted Therapy for Lymphoma with Peptides, Hematology/Onocology Clinincs of North America 11: 1007-1019, |
| Lymphoma stem cell targeting peptides CD 20 and CD19 binding peptides; see above | Hodgkins lymphoma; Hodgkin Reed-Sternberg (HRS) cells | Newcom et al., 1988, Inj. J. Cell Cloning 6: 417-431; Jones et at. 2009, Blood, 113: 5920-5926. |
| Leukemia stem cell targeting peptides ADGACLRSGRGCGAAK SEQ ID NO:66 | Hematological malignancies | Berntzen et al., 2006, Protein Engineering , Design and Selection, doi: 10.1093/protein/gzj011 |
| Somatostatin receptor-binding peptide | Renal cell metastasis | Shih et al., 2004, J. Nucl. Med. Technol 32: 19-21 |
| GFLGEDPGFFNVE SEQ ID NO:67 | Lymphoma | Tang et al., 2000, Bioconjugate Chem 11: 363-371 |

TABLE 4-continued

Examples of targeting peptides

| Peptide sequence or ligand name | Receptor Target | Reference |
|---|---|---|
| The cysteine modified F3-peptide sequence is 5'-CKDEPQRRSARLSAKPAPPKPEPKPKKAPAKK-3'. SEQ ID NO:68 | Tumor neovasculature | Henke et al., 2008, Nature Biotechnology 26: 91-100. |
| Transferrin | Transferrin receptor | |
| Binding peptides for tumor-specific receptors PTHrP, LHRH, alpha V Beta 3 integrin, STEAP, Mesothelin, Endoglin (CD105), KCNK9, EGF receptors (Her1, Her2, Her3, Her4), human mucin (CD19, CD22, CD25, CD33, IL2R, CD2, CD3, CD5, CD7, CD30, GM-CSFR, IL4R IL6R, urokinase receptor, IL13R, transferring receptor), guanylyl cyclase C | for tumor-specific receptors PTHrP, LHRH, alpha V Beta 3 integrin, STEAP, Mesothelin, Endoglin (CD105), KCNK9, EGF receptors (Her1, Her2, Her3, Her4), human mucin (CD19, CD22, CD25, CD33, IL2R, CD2, CD3, CD5, CD7, CD30, GM-CSFR, IL4R IL6R, urokinase receptor, IL13R, transferrin receptor), guanylyl cyclase C | Dyba et al, 2004, Current Pharmaceutical Design 10: 2311-2334; Tarasova et al., WO/2003;072754 |
| Transferrin | Transferrin receptor | |
| P15 peptide GTPGPQGIAGQRGVV SEQ ID NO:69 ANVAENA peptide SEQ ID NO:70 CQTIDGKKYYFN SEQ ID NO:71 Peptide from Clostridium | Type II receptor | Bhatnagar et al., U.S. Pat. No. 6,638,912

Kushnaryov et al., U.S. Pat. No. 5,466,672 |
| Clostridium difficile toxin A | Gal alpha 1-3Gal beta 1-4G1cNAc. | Clark et al., 1987, Toxin A from Clostridium difficile binds to rabbit erythrocyte glycolipids with terminal Gal alpha 1-3Gal beta 1-4G1cNAc sequences Arch Biochem Biophys 15: 257: 217-229 |
| KNGPWYAYTGRO SEQ ID NO:72 NWAVWXKR, SEQ ID NO:73 YXXEDLRRR SEQ ID NO:74 XXPVDHGL SEQ ID NO:75 | Surface idiotype of SUP-88 human B-cell lymphoma | Reviewed by Aina et al. Therapeutic Cancer Targeting Peptides, Biopolymers 66: 184-199 |
| LVRSTGQFV, LVSPSGSWT ALRPSGEWL, AIMASGQWL QILASGRWL, RRPSHAMAR DNNRPANSM, LQDRLRFAT PLSGDKSST SEQ ID NO:76 | Surface idiotype of human chronic lymphocytic lymphoma (CLL) | Reviewed by Aina et al. 2002, Therapeutic Cancer Targeting Peptides, Biopolymers 66: 184-199 |
| FDDARL SEQ ID NO:77, FSDARL SEQ ID NO:78, FSDMRL SEQ ID NO:79, FVDVRL SEQ ID NO:80, FTDIRL SEQ ID NO:81, FNDYRL SEQ ID NO:82 FSDTRL SEQ ID NO:83, PIHYIF SEQ ID NO:84, YIHYIF SEQ ID NO:85, RIHYIF SEQ ID NO:86 | Human multiple myeloma M protein | Reviewed by Aina et al. 2002 |
| IELLQAR SEQ ID NO:87 | HL 60 human lymphoma & B-16 mouse melanoma | Reviewed by Aina et al. 2002 |
| CVFXXXYXXC SEQ ID NO:88, CXFXXXYXYLMC SEQ ID NO:89 | Prostate-specific antigen (PSA) | Reviewed by Aina et al. 2002 |

TABLE 4-continued

Examples of targeting peptides

| Peptide sequence or ligand name | Receptor Target | Reference |
|---|---|---|
| CVXYCXXXXCYVC SEQ ID NO:90 CVXYCXXXXCWXC SEQ ID NO:91 | | |
| DPRATPGS SEQ ID NO:92 | LNCaP prostate cancer | Reviewed by Aina et al. 2002 |
| HLQLQPWYPQIS SEQ ID NO:93 | WAC-2 human neuroblastoma | Reviewed by Aina et al. 2002 |
| VPWMEPAYQRFL SEQ ID NO:94 | MDA-MB435 breast cancer | Reviewed by Aina et al. 2002 |
| TSPLNIHNGQKL SEQ ID NO:95 | Head and neck cancer lines | Reviewed by Aina et al. 2002 |
| SPL W/F,R/K,N/H,S, V/H, L | ECV304 endothelial cell line | Reviewed by Aina et al. 2002 |
| RLTGGKGVG SEQ ID NO:96 | HEp-2 human laryngeal carcinoma | Reviewed by Aina et al. 2002 |
| CDCRGDCFC (RGD-4C) SEQ ID NO:97 | Tumor vasculature | Reviewed by Aina et al. 2002 |
| ACDCRGDCFCG SEQ ID NO:98 | Tumor vasculature | Reviewed by Aina et al. 2002 |
| CNGRCVSGCAGRC SEQ ID NO:99 | Aminopeptidase N | Reviewed by Aina et al. 2002 |
| CVCNGRMEC SEQ ID NO:100, NGRAHA SEQ ID NO:101, TAASGVRSMH SEQ ID NO:102, LTLRWVGLMS SEQ ID NO:103 | Vasculature of various tumors | Reviewed by Aina et al. 2002 |
| LRIKRKRRKRKKTRK SEQ ID NO:104, NRSTHI SEQ ID NO:105 | IC-12 rat trachea | Reviewed by Aina et al. 2002 |
| SMSIARL SEQ ID NO:106, VSFLEYR SEQ ID NO:107 | Mouse prostate | Reviewed by Aina et al. 2002 |
| CPGPEGAGC SEQ ID NO:108 | Aminopeptidase P | Reviewed by Aina et al. 2002 |
| ATWLPPR SEQ ID NO:109, RRKRRR SEQ ID NO:110 | VEGF | Reviewed by Aina et al. 2002 |
| CTTHWGFTLC SEQ ID NO:111 | Gelatinase | Reviewed by Aina et al. 2002 |
| -WYD- SEQ ID NO:112, -WYDD- SEQ ID NO:113, -WYT- SEQ ID NO:114, -WYV- SEQ ID NO:115 | idiotype of WEHI-231 murine lymphoma cell line | Reviewed by Aina et al. 2002 |
| RWID SEQ ID NO:116, RWFD SEQ ID NO:117 | idiotype of WEHI-279 murine lymphoma cell line | Reviewed by Aina et al. 2002 |
| LNNIVSVNGRHX SEQ ID NO:118, DNRIRLQAKXX SEQ ID NO:119 | Alpha-6-beta 1 integrin of DU145 prostate cancer cell line | Reviewed by Aina et al. 2002 |
| Leukemia stem cell binding peptides Leukemia and lymphoma stem cell binding peptides isolated by phage display | Stem cells | Barbass III et al., 2004, Phage Display, A Laboratory Manual, Cold Spring Harbor Press; Ph.D-7 Phage Display Library Kit, New England Biolabs, Ipswich, MA). |
| Macrophage cell binding peptides Macrophage cell binding peptides isolated by phage display | | Barbass III et al., 2004, Phage Display, A Laboratory Manual, Cold Spring Harbor Press; Ph.D-7 Phage Display Library Kit, New England Biolabs, Ipswich, MA). |
| T-cell binding peptides T-cell binding peptides isolated by phage display | | Barbass III et al., 2004, Phage Display, A Laboratory Manual, Cold Spring Harbor Press; Ph.D-7 Phage Display Library Kit, New England Biolabs, Ipswich, MA). |
| Neutrophil binding peptides Neutrophil binding peptides isolated by phage display | | Barbass III et al., 2004, Phage Display, A Laboratory Manual, Cold |

TABLE 4-continued

Examples of targeting peptides

| Peptide sequence or ligand name | Receptor Target | Reference |
|---|---|---|
| | | Spring Harbor Press; Ph.D-7 Phage Display Library Kit, New England Biolabs, Ipswich, MA). |
| Tumor stromal matrix cell binding peptides | | |
| Tumor stromal matrix cell binding peptides isolated by phage display | | Barbass III et al., 2004, Phage Display, A Laboratory Manual, Cold Spring Harbor Press; Ph.D-7 Phage Display Library Kit, New England Biolabs, Ipswich, MA). |

6.4 Lytic Peptides

The desirability of combining protease inhibitors with lytic peptides has not previously been recognized as a means of improving both activity and specificity of proteins delivered by targeted bacteria. Small lytic peptides (less than 50 amino acids) are used to construct chimeric proteins for more than one purpose. The chimeric proteins containing lytic peptides may be directly cytotoxic for neoplasias. In order to be cytotoxic they must be released, surface displayed and/or secreted (FIG. 3) and may be provided with cell specificity by the addition of a targeting ligand. Small lytic peptides have been proposed for use in the experimental treatment of neoplastic diseases. However, it is evident that most, if not all, of the commonly used small lytic peptides have strong antibacterial activity, and thus are not compatible with delivery by a bacterium (see Table 1 of Leschner and Hansel, 2004 Current Pharmaceutical Design 10: 2299-2310, expressly incorporated herein by reference). Small lytic peptides useful in the invention are those derived from *Staphylococcus aureus, S. epidermidis* and related species, including the phenol-soluble modulin (PSM) peptides and delta-lysin (Wang et al., 2007 Nature Medicine 13: 1510-1514, expressly incorporated herein by reference). The selection of the lytic peptide depends upon the primary purpose of the construct, which may be used in combination with other constructs providing other anticancer features. That is, the therapies provided in accordance with aspects of the present invention need not be provided in isolation, and the bacteria may be engineered to provide additional therapies or advantageous attributes. Constructs designed to be directly cytotoxic to cells employ the more cytotoxic peptides, particularly PSM-alpha-3. Constructs which are designed to use the lytic peptide to affect escape from the endosome use the peptides with the lower level of cytotoxicity, such as PSM-alpha-1, PSM-alpha-2 or delta-lysin. Larger lytic peptides that may be used includes the actinoporins and equinatoxins from sea anemones or other coelenterates such as FraC, Sticholysins StsI and StsII (Anderluh and Macek 2002, Toxicon 40: 111-124), are generally more potent than the bacterially-derived peptides, and are selected for use in being directly cytotoxic to parasites. Assay of lytic peptides is known to those skilled in the arts. Examples of lytic peptides useful in the invention are shown in Table 5.

TABLE 5

Membrane lytic peptides useful in the invention

| Peptide and source | Peptide Sequence or name |
|---|---|
| Processed <<short>> active delta lysin *S aureus* | MAQDIISTISDLVKWIIDTVNKFTKK SEQ ID NO:120 |
| Delta lysin processed *S epidermidis* | MMAADIISTI GDLVKWIIDTVNKFKK SEQ ID NO:121 |
| Delta lysin from CA-MRSA | MAQDIISTISDLVKWIIDTVNKFTKK SEQ ID NO:122 |
| PSM-alpha-1 | MGIIAGIIKVIKSLIEQFTGK SEQ ID NO:123 |
| PSM-alpha-2 | MGIIAGIIKFIKGLIEKFTGK SEQ ID NO:124 |
| PSM-alpha-3 | MEFVAKLFKFFKDLLGKFLGNN SEQ ID NO:125 |
| PSM-alpha-4 | MAI VGTIIKIIKAIIDIFAK SEQ ID NO:126 |
| PSM-beta-1 | MEGLFNAIKDTVTAAINNDGAKLG-TSIVSIVENGVGLLGKLFGF SEQ ID NO:127 |
| PSM-beta-2 | MTGLAEAIANTVQAAQQHDSVKLG-TSIVDIVANGVGLLGKLFGF SEQ ID NO:128 |
| Actinoporins Equinatoxins | Lytic peptides from sea anemones and other coelenterates (e.g., SrcI, FraC, Sticholysins StsI and StsII) |

6.5 Antibody and Complement Deactivating Proteins.

Antibody deactivating proteins are useful for limiting the effective immune response against the bacteria vector such that the vector is not eliminated prior to its effective treatment of the neoplastic disease, or during (i.e., following administration but prior to arrival at the target site) and after multiple injections of the same vector at later points in time when an adaptive immune response may have occurred. Antibody deactivating proteins have been suggested to be potentially useful therapeutics for treatment of antibody-based diseases, such as autoimmunity (Nandakumar and Holmadh. 2008, Trends in Immunology 29: 173-178). However, it has not been recognized that expression of these proteins would be desirable in a tumor-targeting bacterial vector as an alternative to serotype variation (as described above), which does not require the generation of multiple strains, each of which require separate testing alone as well as in combination (i.e., succession). The IgG-degrading enzyme of *S. pyogenes* IdeS is a cysteine endopeptidase, secreted by group A streptococcal strains during infection. It cleaves the heavy chains of IgG with a unique specificity by binding and cleaving in the hinge region, thus generating an Fc and a F(ab')2 fragment that can be detected by protein G capture and mass spectrometry. By removing the Fc section from the antigen recognizing Fab, immune responses such as complement deposition and Fc-mediated phagocytosis are blocked. This IgG proteolytic degradation disables opsonophagocytosis and interferes with the killing of group A *Streptococcus*. IdeS bestows a local protective effect for the bacteria. Another IgG degrading enzyme of *Streptococcus pyogenes* is endo-b-N-acetylglucosaminidase (EndoS) which cleavage sites on the IgG molecule. Protein G, the aforementioned protein used in biochemical purification, has IgG antibody deactivation properties Bjork and Kronvall 1984 J Immunol 133: 969-974). Other antibody deactivating proteins include Shistosome IgE proteases and the antibody binding protein A peptides from *Staphalococcus* (e.g., spa gene). The IgA protease of *Neisseria* sp. is an autotrasporter protein. *Streptococcus* PspA inhibits complement activation (Anh-Hue, T et al., 1999. Infect. Immun 67: 4720-4724). Each of these proteins may be expressed individually or in combination in tumor-targeting strains of bacteria.

6.6 Chimeric Bacterial Toxins

Chimeric toxins are toxins that may contain combinations of additional elements including targeting peptides, lytic peptides, nuclear localization signals, blocking peptides, protease cleavage (deactivation) sites, N- or C-terminal secretion signals, autotransporter constructs, used to adapt the proteins to provide therapeutic molecules that are effective in treating neoplastic cells, stromal cells, neoplastic stem cells as well as immune infiltrating cells. Targeting to a particular cell type uses the appropriate ligand from the Table 2 above or from other known sources. Toxin activity is determined using standard methods known to those skilled in the arts such as Aktories (ed) 1997 (Bacterial Toxins, Tools In Cell Biology and Pharmacology, Laboratory Companion, Chapman & Hall).

Figure 3:
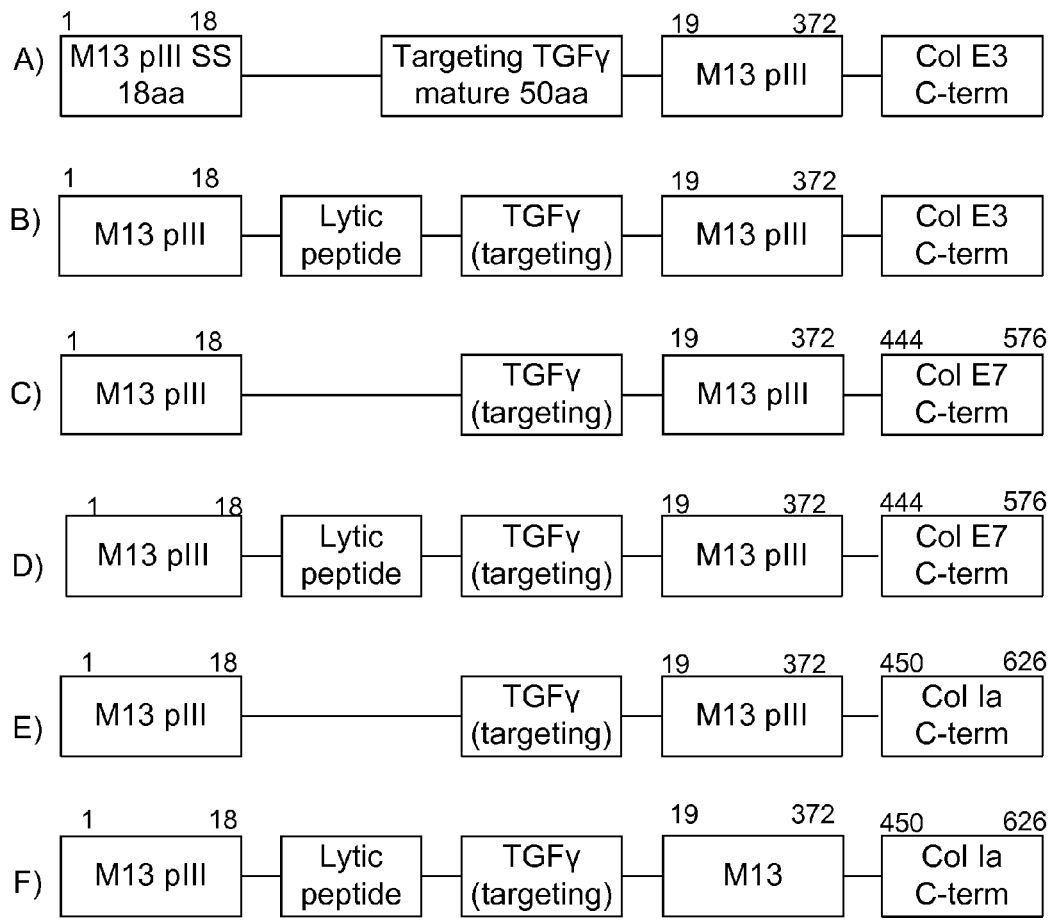
FIG. 3 shows chimeric colicins.

6.6.1 Chimeric colicins with phage proteins. Colicins lack tumor cell targeting. In the present invention, the colicin targeting and translocation domains are replaced with an M13pIII-derived signal sequence and truncated membrane anchor together with a targeting ligand. A lytic peptide may also be added. Examples of the unique organization for chimeric colE3, colE7 and col-Ia are shown in FIG. 3.

Figure 4:
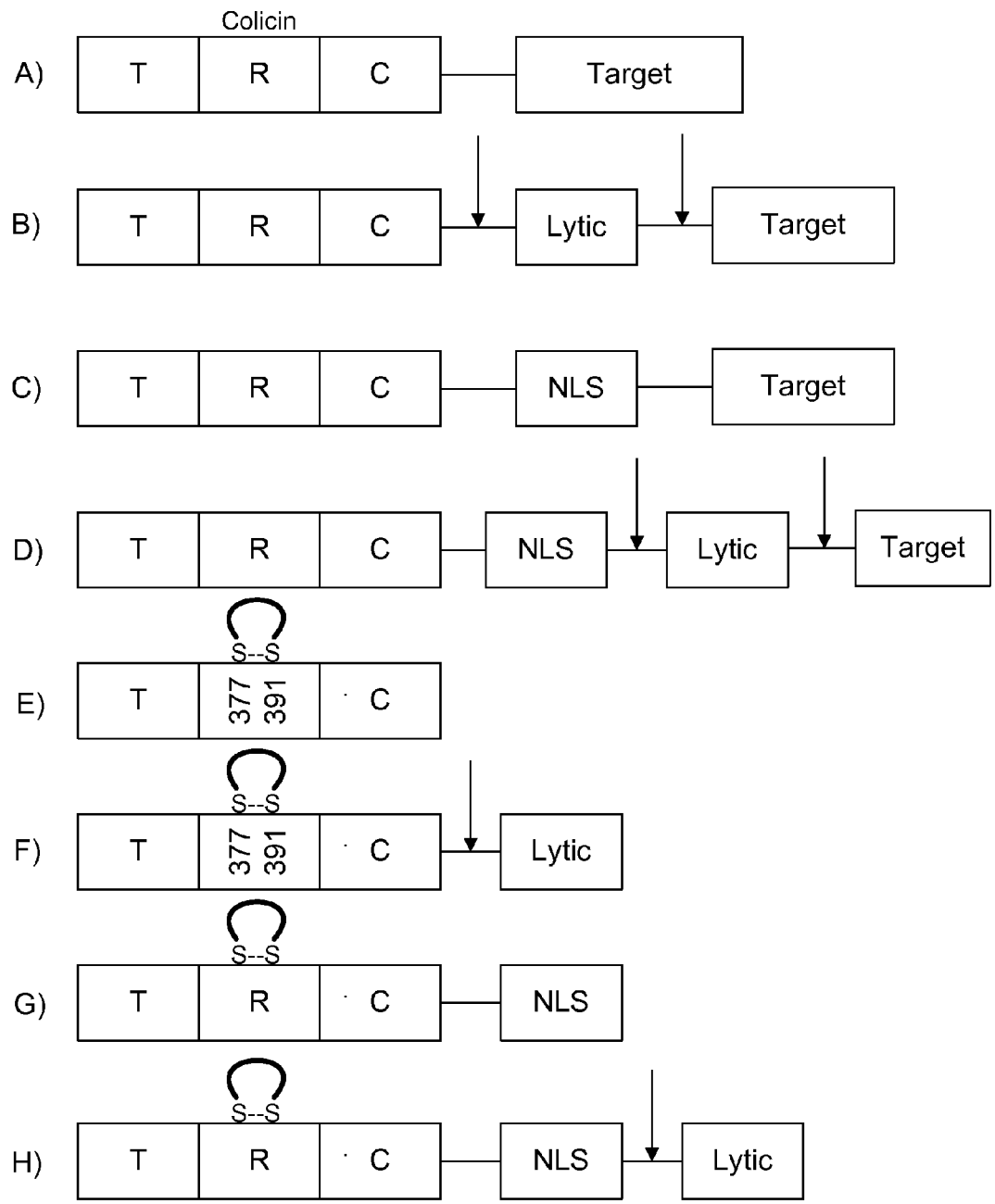
FIG. 4 shows colicin TRC chimeras.

6.6.2 In another version of chimeric colicins, the colicin targeting domain is replaced with a tumor-specific targeting domain (FIG. 4).

6.6.3 In another version of chimeric colicins, the targeting domain is attached to the C-terminus. Further C-terminal modification can include the addition of a NLS, preferably from apoptin, and/or a lytic peptide (FIGS. 3 and 4). The tumor-selective nuclear export signal of apoptin may also be used alone or in combination with the NLS.

Figure 8:
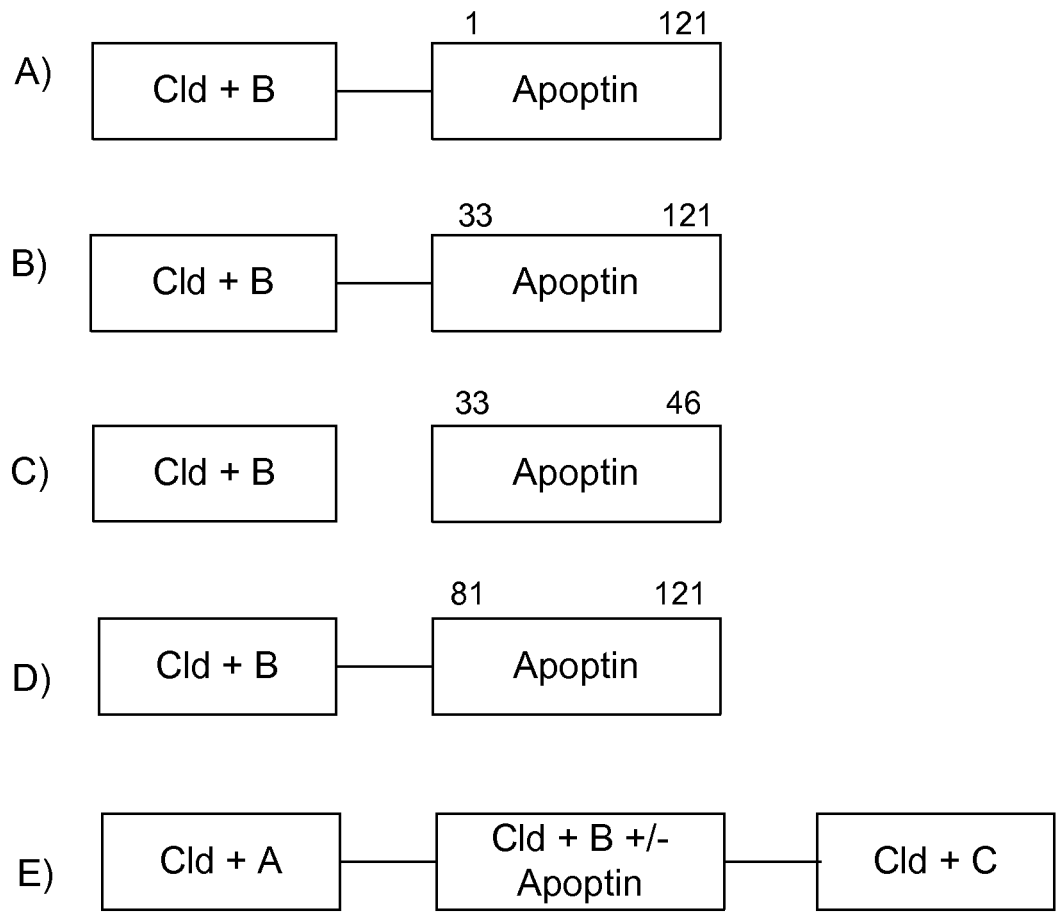
FIG. 8 shows cytolethal distending toxin subunit B (cldtB) chimeras.

6.6.4 Chimeric cytolethal distending toxin. Cytolethal distending toxin (cldt) is a three component toxin of *E. coli, Citrobacter, Helicobacter* and other genera. Cldt is an endonuclease toxin and has a nuclear localization signal on the B subunit. Chimeric toxins are provided that utilize fusion to apoptin, a canary virus protein that has a tumor-specific nuclear localization signal, a normal cell nuclear export signal (FIG. 8). The cytolethal distending toxin B and chimeric cltdB may be expressed as a polycistronic construct consisting of cldtABC. The cytolethal distending toxin B and chimeric cltdB may be expressed as a polycistronic construct consisting containing the typhoid pertussis-like toxin (plt) AB genes.

Figure 9:
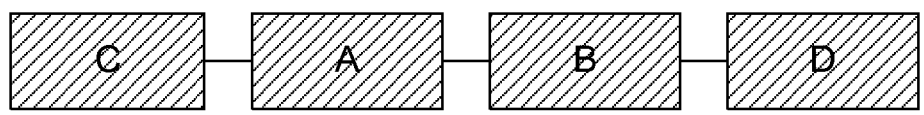
FIG. 9 shows repeat in toxin (RTX) family members and hybrid operons.
Figure 9:
Figure 9:
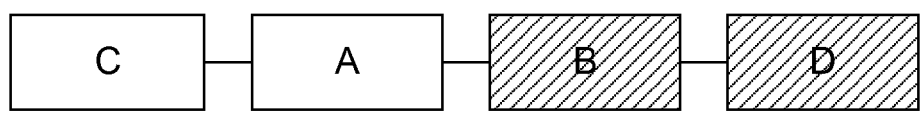
Figure 9:
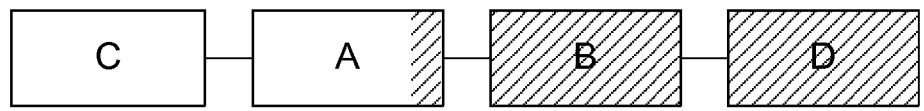

6.6.5 RTX toxins and hybrid operons. *E coli* HlyA(s) operon hlyCABD (+TolC), *Actinobacillus actinomycetemcomitans* leukotoxin ltxCABD, and a hybrid CABD operon are shown in FIG. 9. In addition to direct antitumor activity, they may activate/release liposomal agents when used in combination. The ltxA may be generated as a chimera wherein it contains the C-terminal 60 amino acids of the *E. coli* HlyA. The ltx genes and chimeras may be expressed together with prtF and/or cyaE. Hybrid RTX toxins may be further constructed from known RTX toxins to confer species specificity to multiple species, such as both mouse and human, such that the safety and efficacy testing can occur in multiple species. Multiple sequence alignments of RTX toxins with various species specificities (Ludwig and Goebel, Chapter 29, Structure and mode of action of RTX toxins, Alouf and Popoff (eds), 2006, Comprehensive Sourcebook of Bacterial Protein Toxins, Third Edition, Academic Press; Frey Chapter 30, Genetics and phylogeny of RTX cytolysins, in Kastin (ed), 2006, Alouf and Popoff (eds), 2006, Comprehensive Sourcebook of Bacterial Protein Toxins, Third Edition, Academic Press) are used in the analysis using computer based algorithms such as ClustalW, Muscle 3DCoffee and others (Larkin et al., 2007, ClustalW and ClustalX version 2. Bioinformatics 2007 23(21): 2947-2948 MUSCLE: a multiple sequence alignment method with reduced time and space complexity. BMC Bioinformatics 5: 113; MUSCLE: multiple sequence alignment with high accuracy and high throughput Nucleic Acids Research 32(5): 1792-1797; 3DCoffee: Combining Protein Sequences and Structures within Multiple Sequence Alignments, Journal of Molecular Biology 340: 385-395; Notredame e al., 2000, T-Coffee: A novel method for multiple sequence alignments, Journal of Molecular Biology 302: 205-217; Zdobnov E. M. and Apweiler R. (2001), InterProScan—an integration platform for the signature-recognition methods in InterPro. Bioinformatics 17(9): 847-848; Lassmann T. and Sonnhammer E. L. L. (2006), Kalign, Kalignvu and Mumsa: web servers for multiple sequence alignment, Nucleic Acids Research 34: W596-W59).

Figure 10:
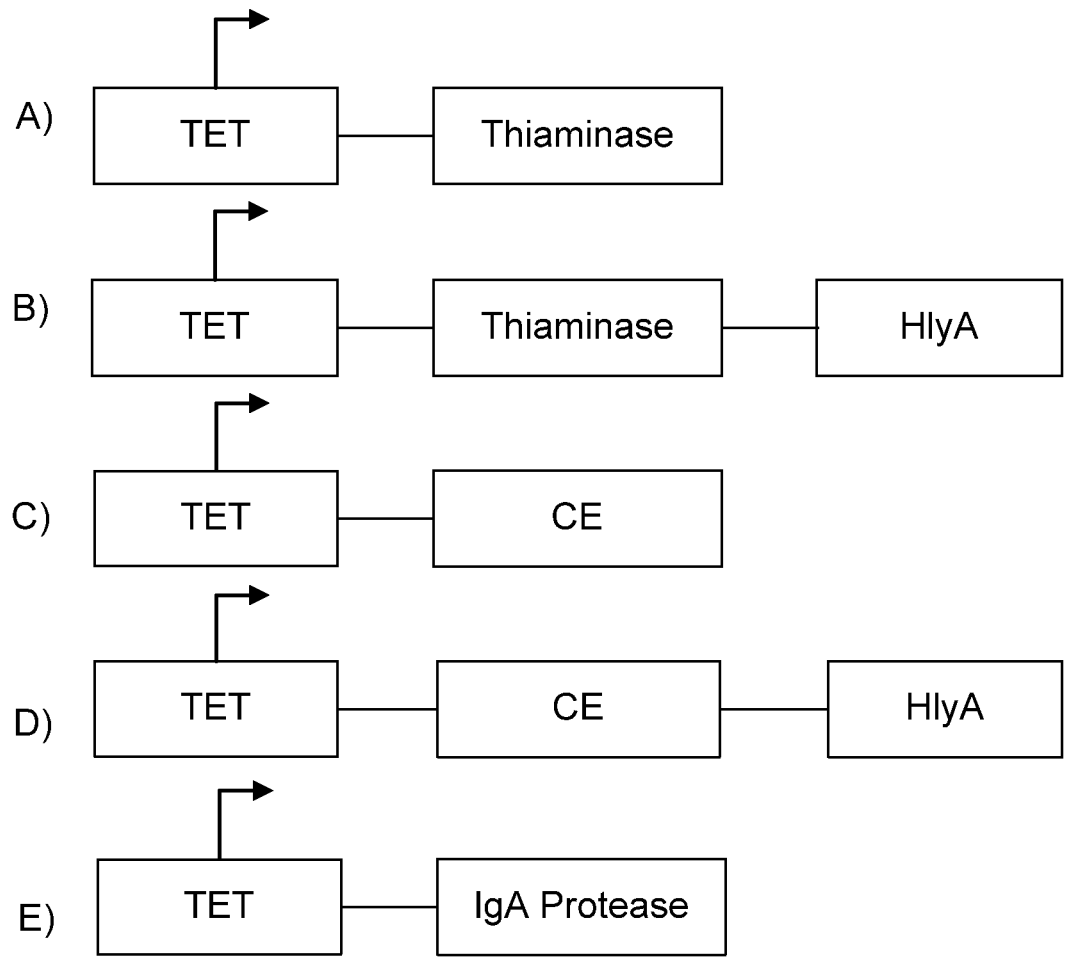
FIG. 10 shows cytoplasmic expressed proteins, hlyA fusions thereof, and non-chimeric surface (autotransporter) expressed proteins.

6.6.6 Saporin and ricin chimeras. Saporin and ricin can be replaced for the active portion of the colicin chimeras. It can also be generated as a targeting peptide, saporin, HlyA C-terminus (FIG. 10).

6.6.7 Cytotoxic necrotic factor (cnf) and *Bordetella* dermonecrotic factor (dnf) chimeras. Cnf and dnf can be expressed as chimeras, where the N-terminal binding domain (amino acids 53 to 190 of cnf) is replaced with a tumor cell binding ligand, such as TGF-alpha.

6.6.8 Shiga toxin (ST) and shiga-like toxin (SLT) chimeras. ST and SLT chimeras are generated wherein the GB3-binding domain is replaced with a tumor cell binding ligand, such as TGF-alpha.

6.6.9 Subtilase toxin chimeras. Subtilase chimeras are generated by replacing the binding domain with a tumor cell binding ligand, such as TGF-alpha.

6.6.10 Nhe (non-hemolytic toxins from *Bacillus*) chimeras are generated by replacing the targeting domain with a tumor cell binding ligand and may be made protease sensitive by addition of a protease cleavage site.

6.6.11 *Clostridium* Tox A binding domain replacements (Rupnik and Just, Chapter 21 in: Alouf and Popoff (eds), 2006, Comprehensive Sourcebook of Bacterial Protein Toxins, Third Edition, Academic Press).

6.6.12 Collagenase chimeras. Collagenase is fused with a targeting peptide that directs its activity towards tumor cells, and may be made protease sensitive by the addition of a protease cleavage site.

Figure 5:
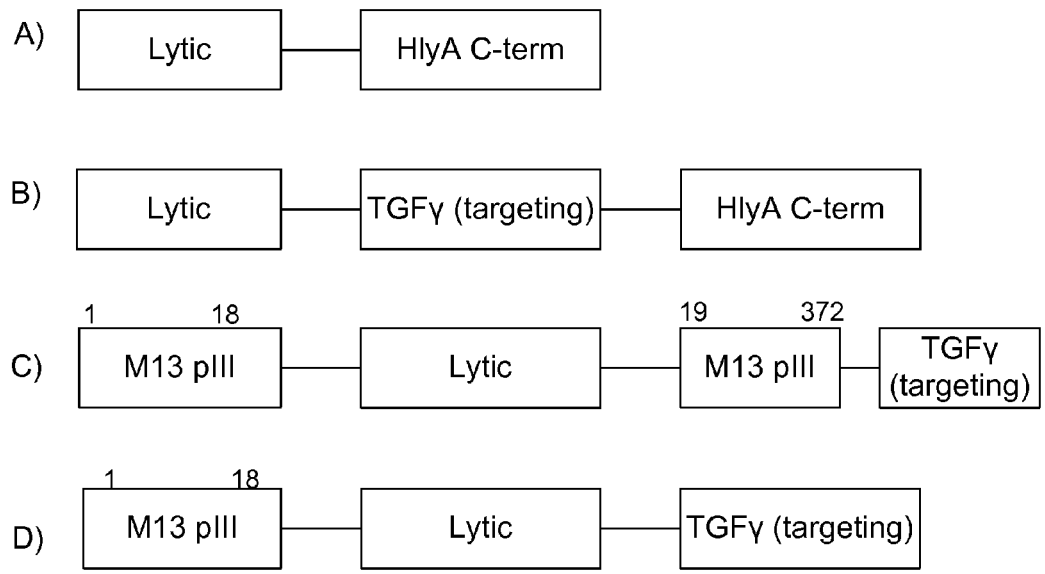
FIG. 5 shows lytic peptide chimeras.
Figure 6:
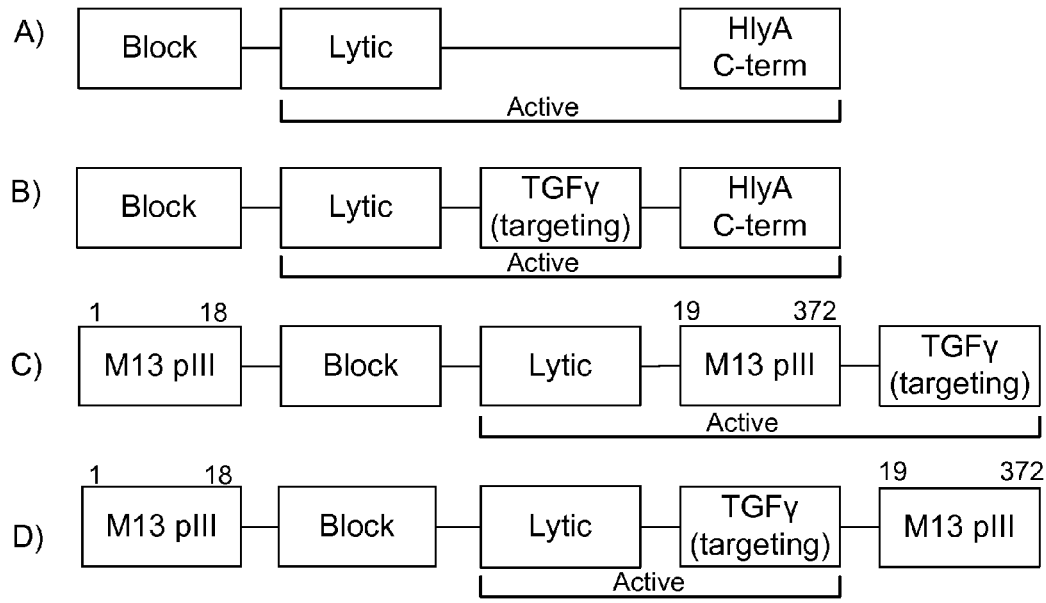
FIG. 6 shows protease activated lytic peptide chimera prodrugs.

6.6.13. Lytic chimeras. Lytic chimeras are shown in FIGS. 5 and 6.

6.7 Expression of Proteins without Generating Chimeras.

Certain proteins of the invention augment the effector gene and protease inhibitor combination without requiring chimeric modification. These proteins include the Geobacter carboxyesterase, the *bacillus* thiaminase and the *Neisseria* IgA protease. The carboxyesterase and thiaminase may also be expressed as hlyA fusion proteins. These proteins may be expressed using constitutive or inducible promoters (FIG. 10).

6.8 Limiting Bacterial Conjugation.

Figure 11:
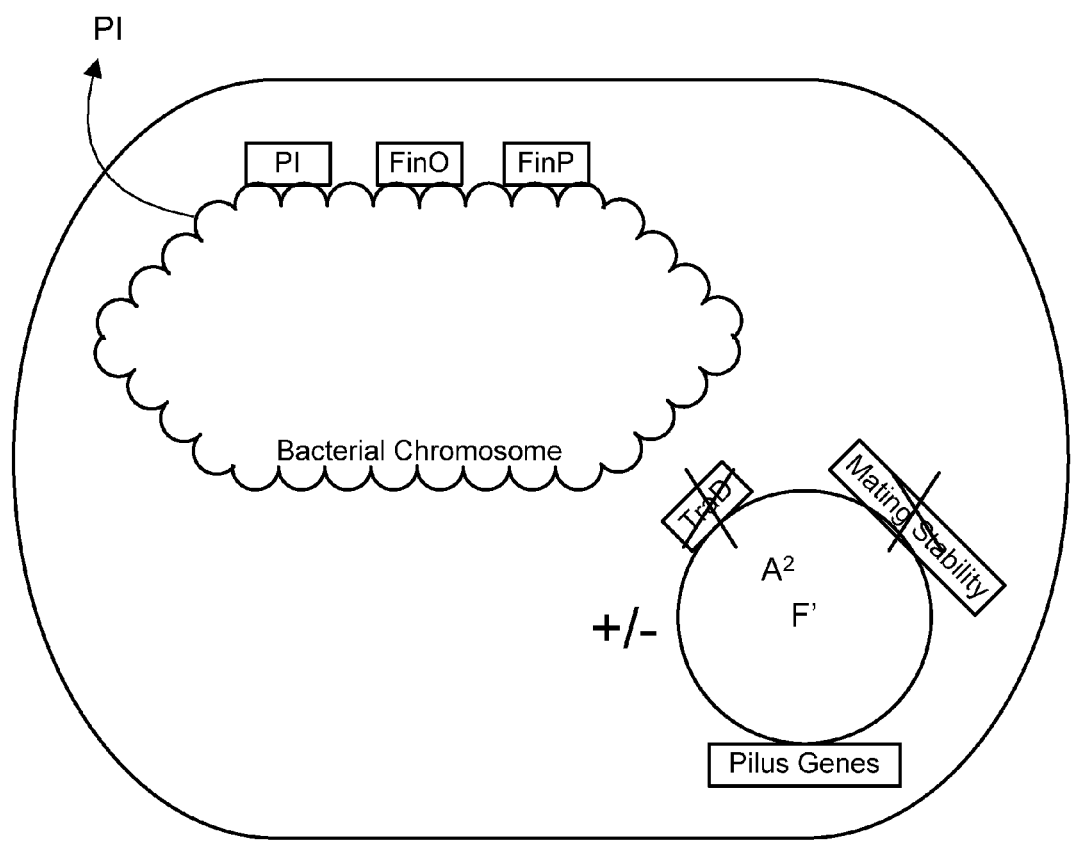
FIG. 11 shows a non-conjugative bacterium with and without the F' factor.

The fertility inhibition complex (finO and finP), are cloned onto the chromosome using standard genetic techniques such that strains either with or without the pilus resistant to mating with F' bacteria (FIG. 11). Other known inhibitory factors may also be used.

The F' pilus factors in a *Salmonella* strain needed for phage to be able to infect the cell are provided by the F' plasmid using standard mating techniques from an F' *E coli*. The F' factor provides other functions such as traD and the mating stabilization which are deleted using standard techniques.

6.9 Expression of DNAase Colicins as Active Extracellular Enzymes.

Colicins have innate potential to harm the host that produces them. In order to protect the host, colicins are naturally co-produced with an "immunity" protein which protects it from the action of the colicin. The immunity proteins are generally specific for each individual colicin, and each has a high affinity for the colicin. When colicins are expressed by the bacteria, the immunity protein immediately binds to the colicin preventing it from harming the host. When colicins are released, the immunity protein may remain bound. Thus, a DNAase colicin may not be expected to have extracellular activity. When colicins are internalized into the target cell the immunity protein remains extracellular, and the colicin thus becomes activated inside the target cell.

In order to generate colicins with extracellular DNAase activity capable of deactivating DNA from neutrophils capable of trapping bacteria (neutrophil nets), the present invention presents a novel combination of DNAase colicin, such as colE9, co-expressed with a non-matching DNAase colicin immunity protein, such as that from colE2, colE7, or colE8, which have higher dissociation constants for colE9 (James et al., 1996, Microbiology 142: 1569-1580). In order to compensate for the reduced amount of protection expected to occur, multiple copies of the non-cognate immunity protein are expressed. Thus, when the colicin E9 is released, the immunity proteins partially dissociate, resulting in extracellular DNAase activity.

In another method of producing an immunity protein that dissociates extracellularly, thus activating the colicin such as a DNAase colicin, the immunity protein, such as colE9 immunity, is subjected to error-prone PCR (e.g., Cirino et al., 2003, Generating mutant libraries using error-prone PCR, Methods in Molecular Biology 231: 3-9; Arnold and Georgiou (eds) 2003, Directed Evolution Library Creation, Humana Press). The library is then cloned into a DNAase colicin-containing plasmid, such as the colE9 colicin, and transformed into a suitable *E. coli* or *Salmonella*. The bacteria are plated to appropriate nutrient agar plates containing DNA. After an incubation period the plates are stained for DNA, e.g., ethidium bromide, and viewed under fluorescent light for "halos"; clear or lighter regions around colonies where the DNA has been digested. Such colonies will contain the colE9 colicin, and an immunity protein that is sufficiently stable intracellularly such that it protects the bacterial cell, allowing it to grow, and is capable of dissociating under extracellular conditions, allowing the DNAase colicin to degrade extracellular DNA. The assay may be further modified to alter the agar plate conditions to match conditions of the target site, such as lower pH that is known to occur in solid tumors. The, the process would then select for functional immunity proteins that dissociate under acidic pH, such as occurs in solid tumors, allowing the degradation of extracellular DNA, such as may occur from infiltrating neutrophils.

6.10 Co-Expression of Protease Inhibitors with Bacterial Toxins, Chemotherapeutic Agents, Clodronate, Carbogen, and Determinations of Combination Effects, Antagonism, Additivity and/or Synergy.

Each of the bacterial toxins and therapeutic peptides and proteins listed herein may be improved in its therapeutic activity by co-expression with a protease inhibitor. Inhibitors are expressed as secreted proteins as described above. The effect of the protease inhibitor on in vitro cytotoxicity is determined using standard cell culture techniques and cytotoxicity assays such as MTT (3-(4,5-Dimethylthiazol-2-yl)-2,5-diphenyltetrazolium bromide, a tetrazol; Mosmann 1983; J. Immunol Methods 65:55-63) known to those skilled in the arts. The contribution of the protein cytotoxin and protease inhibitors is determined individually and in combination. Purified protease of types known to occur in the target tissue, such as a solid tumor, lymphoma, myeloma, or the lumen of a leukemic bone, may be added to the assay. Combination effects, including antagonism, additivity or synergy may be determined using the median effect analysis (Chou and Talaly 1981 Eur. J. Biochem. 115: 207-216) or other standard methods (White et al., 1996, Antimicrobial Agents and Chemotherapy 40: 1914-1918; Brenner, 2002, Annals of Oncology 13: 1697-1698; Berenbaum M C. 1989. What is synergy? *Pharmacol Rev.* 41(2): 93-141; Greco W R, Bravo G, Parsons J C. 1995. The search for synergy: a critical review from a response surface perspective. *Pharmacol Rev.* 47(2): 331-85); Zhao et al., 2004, Evaluation of Combination Chemotherpy, Clin Cancer Res 10: 7994-8004; Loewe and Muischnek, 1926. Effect of combinations: mathematical basis of the problem, Arch. Exp. Pathol. Pharmakol. 114: 313-326). The assay may also be used to determine synergy, additivity or antagonism of two or more bacterial cytotoxins. The assay may also be used to determine synergy, additivity or antagonism a bacterial cytotoxin together with a conventional small molecule cytotoxin (e.g., cisplatin, doxorubicin, irinotecan, paclitaxel or vincristine), targeted therapeutic (e.g., imatinib, irissa, cetuximab), proteosome inhibitors (e.g., bortezomib), mTOR inhibitors or PARP inhibitors. Treatment with drugs such as imatinib prior to injection of *Salmonella* may also enhance bacterial tumor targeting (Vlahovic et Br J Cancer 2007, 97 735-740). In vivo studies may also be performed with antiangiogenic inhibitors such as Avastin, combrettastatin, thalidomide. In vivo studies with reticuloendothelial system (RES) blocker such as chlodronate which have the potential to improve the circulation time of the bacteria, vacular permeability inducing agents such as bradykinin, hyperthermia or carbogen which have the potential to improve the permeability of the tumor enhancing entry of the bacteria or aldose reductase inhibitors. Preferred genetic backgrounds for msbB mutant *Salmonella* in combination with carbogen (carbon dioxide oxygen mixture) includes zwf, which confers resistance to $CO_2$ (Karsten et al., 2009, BMC Microbiol. BMC Microbiol. 2009 Aug. 18; 9:170).

6.11 Segregation of Required Colicin Toxin Cofactors.

Figure 12:
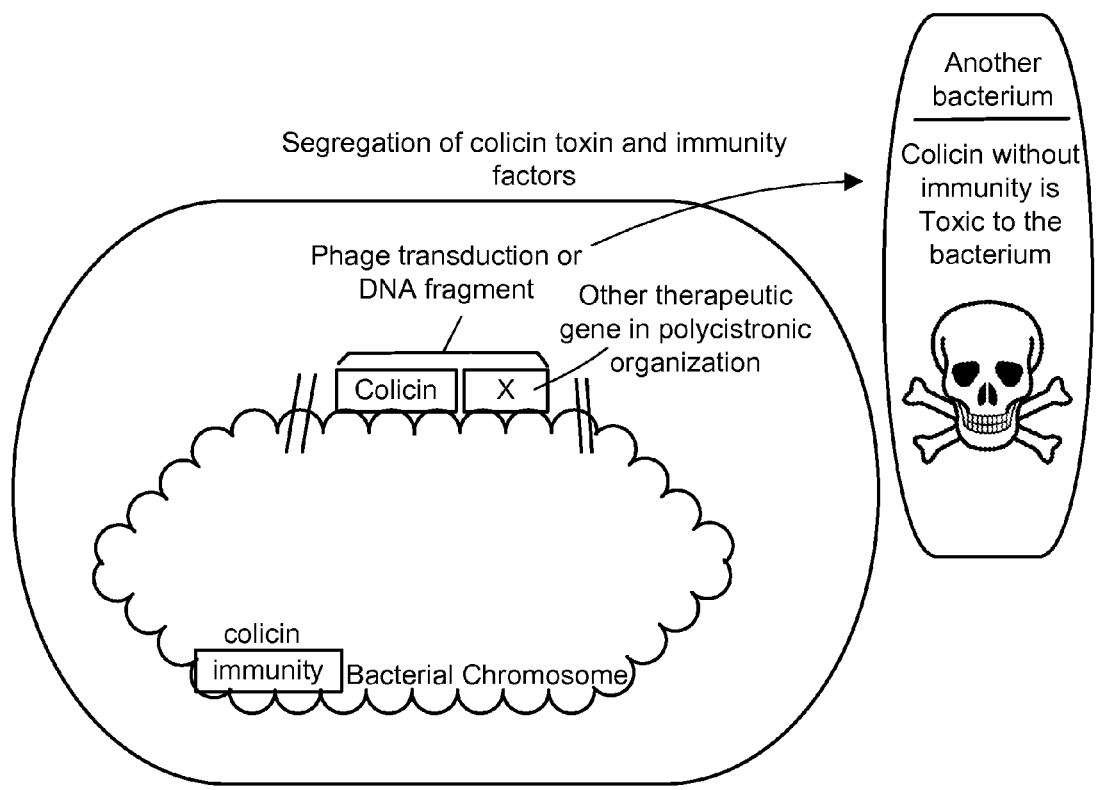
FIG. 12 shows segregation of required colicin toxin and immunity factors.

The chimeric colicin toxins have active colicin components that require their respective immunity proteins, which are usually genetically linked. By unlinking the two genes and separating them on the chromosome, a single fragment or phage transduction is highly unlikely to contain both elements. In order to separate the elements from co-transmission by a transducing phage such as P22, separation by 50 kB or greater is preferred. Without both elements, the toxin portion cannot be carried and will kill most bacteria. Any additional genes such as other chimeric therapeutic molecules genetically linked to the colicin will also be inhibited from being transferred to other bacteria (FIG. 12)

6.12 Characteristics of Therapeutic Bacteria Co-Expressing Protease Inhibitors with Chimeric Antigens, Lytic and Therapeutic Proteins The primary characteristic of the bacteria of the invention is the enhanced effect of the effector molecule such as a toxin, lytic peptide etc. relative to the parental strain of bacteria without expressing one or more protease inhibitors. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more protease inhibitors under the same conditions.

A second characteristic of the bacteria of the invention is that they carry novel chimeric proteins that prevent their elimination by antibodies compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

A third characteristic of the bacteria of the invention is that they carry novel chimeric proteins that improve their function compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

A fourth characteristic of the bacteria of the invention is that they carry heterologous proteins that suppress features of the immune system that include antibody binding and/or deactivating proteins, targeted peptides against activated T and B cells, extracellular DNases that prevent destruction by neutrophil nets, and antitumor toxins with cross-over anti-neutrophil activity (dual antitumor and anti-neutrophil activity). The *Yersinia pestis* secreted protein LcrV that triggers the release of interleukin 10 (IL-10) by host immune cells and suppresses proinflammatory cytokines such as tumor necrosis factor alpha and gamma interferon as well as innate defense mechanisms required to combat the pathogenesis of plague.

The immunosuppressive features together with the antibody and complement deactivation proteins allow repeated injections of the bacteria without elimination form the immune system, where improvement is defined as the percentage of bacteria present at the target site after between 1 to 21 days compared to the parental strain in a murine model. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

Overall improvement is defined as an increase in effect, such as the ability to kill a neoplastic cells in vitro by the bacteria, or inhibit or reduce the volume or cell number of a solid tumor, carcinoma, lymphoma or leukemia in vivo following administration with the bacteria expressing a therapeutic molecule, with and without the protease inhibitor, and/or with and without an antibody inhibiting peptide. The effect of the protease inhibitor on protein therapeutic activity is determined using standard techniques and assays known to those skilled in the arts. Inhibitors are expressed as secreted, surface displayed and/or released proteins as described above. Likewise, the effect of the antibody inhibitory protein on therapeutic activity is determined using standard techniques and assays known to those skilled in the arts. Antibody inhibitors are expressed as native proteins (e.g., IgA protease in gram negative bacteria for vectors such as those using *Salmonella*, or spa, IdeS and EndoS in gram positive bacteria for vectors such as those using *Streptococcus*) or as secreted protein chimeras as described above such as a fusion with hlyA. The contribution of the therapeutic protein, protease inhibitors and/or antibody inhibitory proteins is determined individually and in combination. Additivity, synergy or antagonism may determined using the median effect analysis (Chou and Talaly 1981 Eur. J. Biochem. 115: 207-216) or other standard methods.

7. FIGURE LEGENDS

Figure 1B:
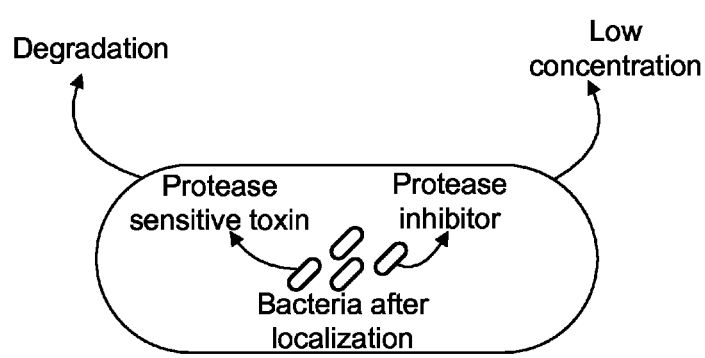

FIG. 1. Comparison of tumor-protease activated toxin with tumor protease inhibitor and protease sensitive toxin expression. A) Intravenously injected tumor protease activated toxin remains active if it diffuses out of the tumor. B) Intratumoral bacteria co-expressing a protease inhibitor and a protease sensitive toxin achieve high intratumoral activity and degradation following diffusion out of the tumor. The co-expression system results in high intratumoral activity, achieving a therapeutic benefit with low toxicity.

Figure 2:
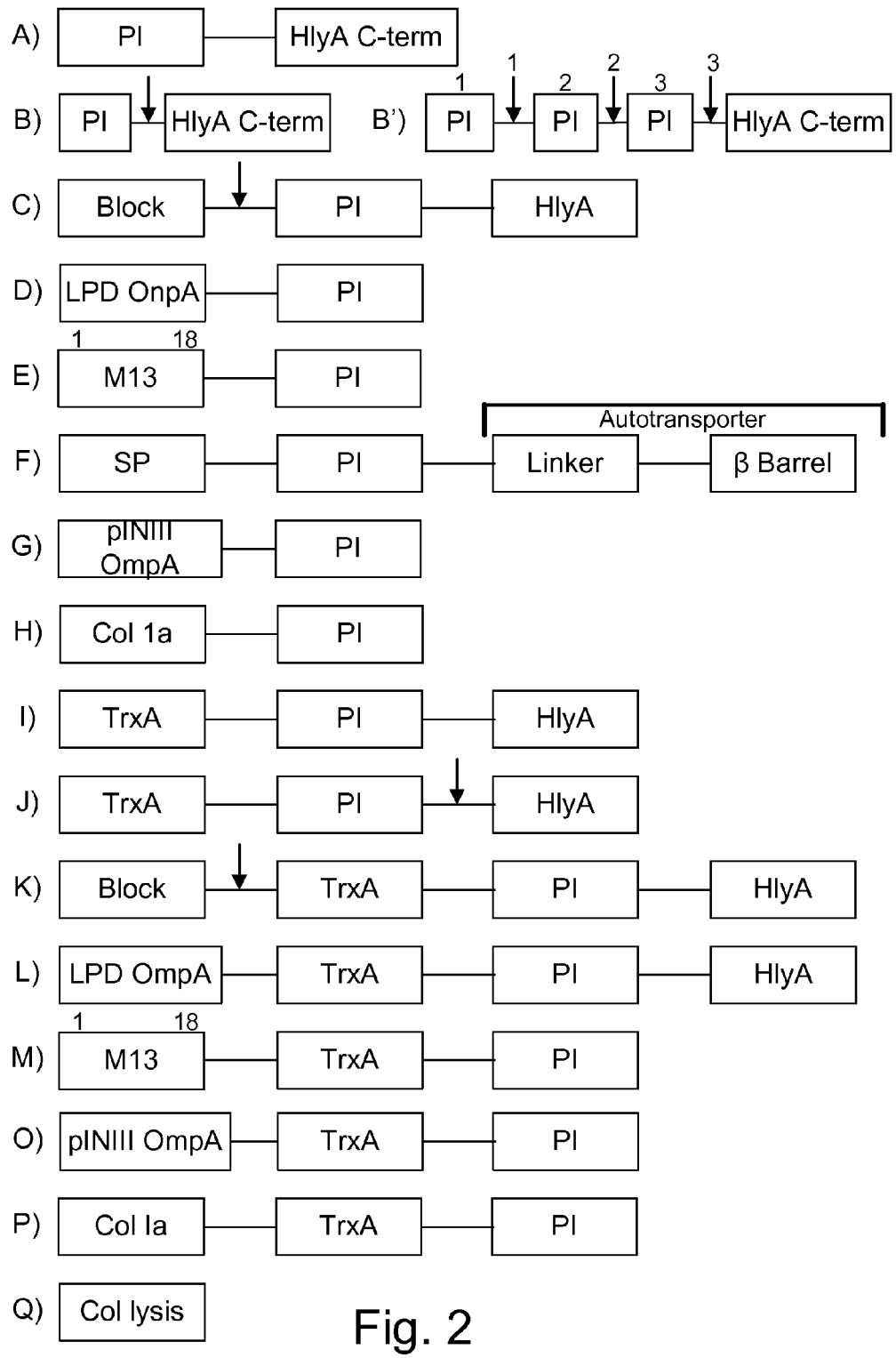
FIG. 2 shows secreted protease inhibitors.

FIG. 2. Secreted protease inhibitors (PIs). A) A PI followed by the hlyA C-terminal signal sequence. B) A PI followed by an intervening protease cleavage site (downward arrow) and the hlyA C-terminal signal sequence. B'). Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have multiple inhibitors for the same or different proteases, respectively), and/or homo- or hetero-protease cleavage polymers (i.e., have multiple of the same or different protease cleavage sites). Thus, protease inhibitors 1, 2 and 3 can be the same protease inhibitor or different protease inhibitors, and the protease cleavage sites (downward arrows) can be the same protease cleavage side or different protease cleavage sites. C) A blocking peptide followed by an intervening protease cleavage site (downward arrow) and then the hlyA C-terminal signal sequence. D) The LPP:OmpA signal sequence followed by a protease inhibitor. E) The M13 pIII signal sequence (amino acids 1-18) followed by a protease inhibitor. F) An autotransporter cassette consisting of an autotransporter signal peptide, a protease inhibitor (passenger) followed by the autotransporter linker and β-barrel. G) A pINIIIompA leader with a protease inhibitor (Longstaff et al., Biochemistry 1990 29: 7339-7347). H) A colicin N-terminal domain with a protease inhibitor. I) A thioredoxin (TrxA) fusion with a PI followed by the hlyA C-terminal signal sequence. J) A thioredoxin (TrxA) fusion with a PI followed by an intervening protease cleavage site (downward arrow) and the hlyA C-terminal signal sequence. K) A blocking peptide followed by a thioredoxin (TrxA) fusion with an intervening protease cleavage site (downward arrow) and then the hlyA C-terminal signal sequence. L) The LPP:OmpA signal sequence followed by a thioredoxin (TrxA) fusion with a protease inhibitor. M) The M13 pIII signal sequence followed by a thioredoxin (TrxA) fusion with a protease inhibitor. N) An autotransporter cassette consisting of an autotransporter signal peptide, a thioredoxin (TrxA) fusion and a protease inhibitor (passengers) followed by the autotransporter linker and β-barrel. O) A pINIIIompA leader with a thioredoxin (TrxA) fusion with a protease inhibitor. P) A colicin N-terminal domain with a thioredoxin (TrxA) fusion with a protease inhibitor. Q) F) A colicin lysis protein that may be co-expressed in trans with any of the above.

FIG. 3. Chimeric phage pIII protein colicins. A) An M13 pIII signal sequence with amino acids 1 to 18 followed by a targeting peptide (TGF-alpha), a membrane anchor truncated M13 pIII amino acids 19 to 372 and the C-terminus of ColE3 (ribonuclease). The colicin is secreted, the signal sequence cleaved and the targeting peptide targets the EGFR-expressing cancer cell. B) A lytic peptide is added between the signal sequence and the targeting peptide. Following cleavage of the signal sequence, the targeting peptide localizes to the EFGF-expressing cancer cell and the lytic peptide assists in its release from the endosome. C) A ColE7 (DNAase) chimera. Optionally, a NLS, preferably from apoptin, may be added at the C-terminus. D) A ColE7 chimera with a lytic peptide. Optionally, a NLS, preferably from apoptin, may be added at the C-terminus. E) A Col-Ia (membrane channel forming peptide) chimera. F) A Col-Ia chimera with a lytic peptide.

FIG. 4. Colicin TRC fusions. Colicin TRC fusions utilize the entire colicin with its three domains, T (translocation), R (receptor), and C (catalytic), and fuse active moieties to the C-terminal catalytic domain. A) TRC of a colicin, such as colE3, and a targeting domain, such as TGF-alpha. B) TRC of a colicin, such as colE3, a lytic peptide such as PSM-alpha-1, and a targeting domain, such as TGF-alpha. The lytic peptide may be engineered to have protease cleavage sites, such as those from cathepsin, that effect its release and aid in escape from an endosome. C) TRC of a DNAase colicin, such as colE9 where it is desirable to direct the DNAase activity to the tumor, a nuclear localization domain (NLS), preferably that of Apoptin, and a targeting domain such as a CD22 binding peptide. The CD22 peptide is disulfide bonded (S—S) loop. Alternatively, a peptide library such as are used in phage display, including those using disulfide bonding may be used. Such libraries are may be first selected using phage, or may alternatively first be selected by screening of colicins for target cell specificity and then transferred to the colicin receptor region. In addition, a library of the "tol box" penta peptide (DGSGW SEQ ID NO:133) variations and/or extended tolB box (DGS-GWSSENNPWGGGSGSIHW SEQ ID NO:134; Hands et al., 2005, Interactions of TolB with the translocation domain of colicin E9 require and extended tolB box, J Bacteriol. 187: 6733-6741) variations may be screened alone or in combination with individual receptor peptides such as the CD22 binding peptide, or a library of receptor peptides and a library of tol box or extended tol box peptides may be screened in combination. D) TRC of a DNAase colicin, such as colE9 where it is desirable to direct the DNAase activity to the tumor, a nuclear localization domain (NLS), preferably that of Apoptin, a lytic peptide such as PSM-alpha-1, and a targeting domain, such as a CD22 binding peptide. The lytic peptide may be engineered to have protease cleavage sites, such as those from cathepsin, that affects its release and aids in escape of the colicin chimera from an endosome. E) TRC of colicin E3, a ribonuclease colicin active in the cytoplasm, where a targeting peptide, such as CD22 binding peptide, is inserted into the targeting domain, between amino acids 374 and 391. F) TRC of colicin E3, a ribonuclease colicin active in the cytoplasm, where a targeting peptide, such as CD22 binding peptide, is inserted into the targeting domain between amino acids 374 and 391 and a lytic peptide is engineered in-frame. The lytic peptide may be engineered to have a protease cleavage site, such as those from a cathepsin, that affects its release and aids in escape of the colicin chimera from an endosome. G) TRC of colicin E9, a DNAase colicin active in the nucleus, where a targeting peptide, such as CD22 binding peptide, is inserted into the targeting domain. H) TRC of colicin E9, a DNAase colicin active in the nucleus, where a targeting peptide, such as CD22 binding peptide, is inserted into the targeting domain. and a lytic peptide is engineered in-frame. The lytic peptide may be engineered to have a protease cleavage site, such as those from a cathepsin, that affects its release and aids in escape of the colicin chimera from an endosome.

FIG. 5. Lytic effector peptide chimeras. A) A lytic peptide followed by the hlyA signal sequence. B) A lytic peptide, targeting peptide (TGF-alpha), hlyA signal peptide chimera. C) The M13 pIII signal sequence followed by a lytic peptide, the membrane anchor truncated M13 pIII amino acids 19 to 372 and a targeting peptide (TGF-alpha). D) The M13 pIII signal sequence followed by a lytic peptide and a targeting peptide (TGF-alpha).

FIG. 6. Protease activated lytic peptide chimera prodrugs (for which the active portion is not sensitive and for which a protease inhibitor is not being co-expressed). A) A blocking peptide followed by a tumor protease cleavage site, a lytic peptide followed by the hlyA signal sequence. The bracket underneath shows the active portion of the chimera following proteolytic cleavage. B) A blocking peptide followed by a tumor protease cleavage site, a lytic peptide, targeting peptide (TGF-alpha) followed by a second tumor protease cleavage site and the hlyA signal peptide. C) The M13 pIII signal sequence followed by a blocking peptide with a tumor protease cleavage site, a lytic peptide, the membrane anchor truncated M13 pIII amino acids 19 to 372 and a targeting peptide (TGF-alpha). D) The M13 pIII signal sequence followed by a blocking peptide with a tumor protease cleavage site, a lytic peptide, a targeting peptide (TGF-alpha) with a tumor protease cleavage site and the membrane anchor truncated M13 pIII amino acids 19 to 372.

Figure 7:
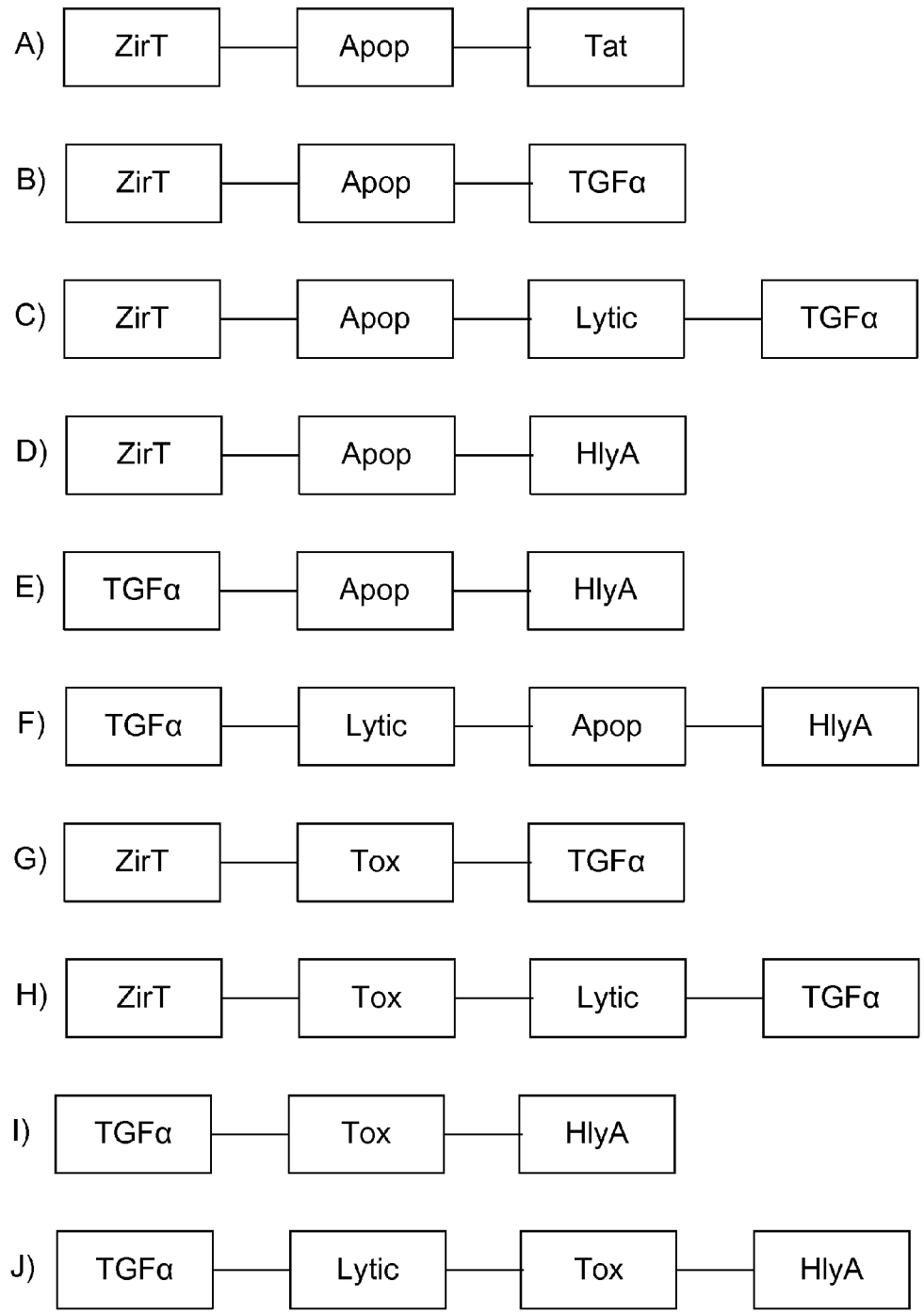
FIG. 7 shows apoptotic peptide and toxic peptide chimeras.

FIG. 7. Proapoptotic and cytotoxic peptide fusions. A) Proapoptotic ("apop") peptides, such as BH3 peptide, BAX, BIM, BAD, p53 peptide, or apoptin are engineered with signal sequence such as that from ZirT and a ferry peptide, such as the HIV TAT peptide. The chimeras may be expressed together with a release factor such as a colicin lysis protein. B) Proapoptitic (apop) peptides, such as BH3 peptide, BAX, BIM, BAD, p53 peptide, or apoptin) are engineered with an N-terminal signal sequence (e.g., ZirT)

and a C-terminal targeting peptide such as TGF-alpha. May be expressed together with a release factor such as a colicin lysis protein. C) Proapoptitic (apop) peptides, such as BH3 peptide, BAX, BIM, BAD, p53 peptide, or apoptin) are engineered with an N-terminal signal sequence, a lytic peptide and a targeting peptide such as TGF-alpha. The lytic peptide may be engineered to have protease cleavage sites, such as those from a cathepsin, that affects its release and aids in escape of the apoptotic peptide chimera from an endosome. May be expressed together with a release factor such as a colicin lysis protein. D) An N-terminal ferry peptide such as HIV TAT peptide is engineered in-frame with an apoptotic peptide with a C-terminal signal sequence from an RTX toxin such as HlyA. E) A targeting peptide such as TGF-alpha engineered in-frame with an apoptotic peptide and a C-terminal signal sequence from an RTX toxin such as HlyA. F) A targeting peptide such as TGF-alpha engineered in-frame with a lytic peptide and an apoptotic peptide with a C-terminal signal sequence from an RTX toxin such as HlyA. The lytic peptide may be engineered to have protease cleavage sites, such as those from a cathepsin, that affects its release and aids in escape of the colicin chimera from an endosome. G) An N-terminal signal sequence, such as that from ZirT, a toxic peptide (e.g., ricin, soporin), and a targeting peptide such as TGF-alpha. H) An N-terminal signal sequence, such as that from ZirT, a toxic peptide (e.g., ricin, soporin), a lytic peptide and a targeting peptide such as TGF-alpha. The lytic peptide may be engineered to have protease cleavage sites, such as those from a cathepsin, that affects its release and aids in escape of the colicin chimera from an endosome. I) A targeting peptide such as TGF-alpha, a toxic peptide, and the hlyA C-terminal signal sequence. J) A targeting peptide such as TGF-alpha, a lytic peptide, a toxic peptide, and the hlyA C-terminal signal sequence. The lytic peptide may be engineered to have protease cleavage sites, such as those from a cathepsin, that affects its release and aids in escape of the colicin chimera from an endosome.

FIG. 8. Cytolethal distending toxin subunit B (cldtB) chimeras. It is understood that full functionality requires cltdA and cltdC. A) CldtB followed by apoptin 1 to 121. B) CldtB followed by apoptin 33 to 121. C) CldtB followed by apoptin 33-46. D) CldtB followed by apoptin 81-121.

FIG. 9. Repeat in toxin (RTX) family members and hybrid operons. A) HlyCABD from *E. coli*. B) LtxCABD from *Actinobacillus*. C) A hybrid CABD of *E coli* (HlyBD) and *Actinobacillus* (HlyCA). D) A hybid ltxCA with *E. coli* BD where the ltxA contains the C-terminal 60 amino acids of HlyA.

FIG. 10. Non-chimeric effector proteins which may be optionally expressed as secretion fusions in combination with protease inhibitors. A) An inducible promoter (e.g., TET) which drives the expression of a metabolic degrading enzyme such as thiaminase, methionase (methioninase L-methionine γ-lyase) or asparaginase. B) An inducible promoter (e.g., TET) which drives the expression of a metabolic enzyme such as thiaminase (or methionase or asparaginase) expressed as a HlyA fusion. C) An inducible promoter (e.g., TET) which drives the expression of a prodrug converting enzyme (e.g., carboxyesterase; CE). D) An inducible promoter (e.g., TET) which drives the expression of a prodrug converting enzyme (e.g., carboxyesterase; CE) expressed as a HlyA fusion. E) An inducible promoter (e.g., TET) which drives the expression of an antibody degrading autotransporter (IgA protease from *Neisseria*).

FIG. 11. A non-conjugative bacterium with and without the F' factor. The bacterial chromosome contains a secreted protease inhibitor construct (PI) that results in a secreted protease inhibitor. The chromosome also contains the FinO and FinP genes in order to inhibit conjugation. When present, the F' factor containing the pilus genes with deletions relating to conjugation in traD and the mating stabilization (MS) results in a pilus expressed by the bacterium.

FIG. 12. Segregation of colicin toxin and required immunity factor(s). The bacterial chromosome has a colicin immunity protein integrated into a neutral sight (e.g., attenuating mutation or IS200 element). The colicin, or colicin hybrid is not linked to the immunity protein, but is distal to it. Other therapeutic molecules may be in the same proximity, such as in a polycistronic organization. Based on this organization, a random DNA fragment, or a portion of the genome packaged by a transducing phage, could not contain the immunity protein. If such a fragment were transferred to another bacterium, expression of the colicin without the immunity protein would kill the cell. A second colicin set, with another distal colicin immunity protein and a corresponding colicin on the other flanking side of the effector system may also be used.

8. EXAMPLES

In order to more fully illustrate the invention, the following examples are provided.

8.1. Example: Methods for Obtaining Bacterial Strains with Suitable Genetic Backgrounds A first step in selection of an appropriate strain based upon the known species specificity (e.g, *S. typhi* is human specific and *S. typhimurium* has broad species specificity including humans, birds, pigs and many other vertebrates). Thus, if the target species for treatment were limited to humans, *S. typhi* would be appropriate. If more species are desired to be treated including humans, cats, dogs, horses and many other vertebrates, then other serotypes may be used. For example, *S. typhimurium* and *S. montevideo* which have non-overlapping O-antigen presentation (e.g., *S. typhimurium* is O-1, 4, 5, 12 and *S. typhi* is Vi, *S. montevideo* is O-6, 7) are representative examples. Methods to genetically alter the serotype within a single strain are known to those skilled in the arts, including Favre et al., 1997 WO 97/14782 Methods for delivering heterologous 0-antigens; and Roland, 2000, WO/2000/004919). Thus, *S. typhimurium* is a suitable serotype for a prime/boost strategy where *S. typhimurium* is either the primary vaccine, or the booster vaccine where the primary vaccine is another serotype such as *S. typhi* or *S. montevideo*. Furthermore, both *S. typhimurium* and *S. montevideo* are suitable for humans, cats, dogs, or horses. A second step follows serotype selection where the first genetic mutation is introduced which may involve the use of antibiotic resistance markers and where any antibiotic resistance makers are then eliminated, followed by a third step where a second genetic mutation is introduced which may involve the use of antibiotic resistance markers and where any antibiotic resistance makers are then also eliminated. Reiteration of genetic deletion and antibiotic marker elimination can be used to supply additional mutations. Methods for reiterative chromosomal deletion and elimination of antibiotic resistance markers are known to those skilled in the arts, including Tn10 transposon deletion followed by "Bochner" selection (Bochner et al., 1980, J Bacteriol. 143: 926-933) for elimination of the tetracycline antibiotic resistance marker, lamda red recombinase deletion followed by flip recombinase elimination of the antibiotic resistance marker (Lesic and Rahme, 2008, BMC Molecular Biology 9:20), and suicide vectors such as those containing sucrase gene (e.g., pCVD442, Donnenberg and Kaper, 1991 Infect Immun 59: 4310-4317). Spontaneous mutations may also be rapidly and accurately selected for, such as the "Suwwan", a large IS200-mediated deletion (Murray et al., 2004, Journal of Bacteriology, 186: 8516-8523). Thus, the starting strain can be a wild type *Salmonella* such as ATCC 14028, and the Suwwan, IS200 deletion selected for using chlorate (Murray et al., 2004, Journal of Bacteriology, 186: 8516-8523). A second mutation in msbB can be introduced using pCVD442 as described by Low et al., 2004, Methods Mol Med. 2004; 90:47-60). A third mutation can be generated in zwf as described by Karsten et al., 2009, BMC Microbiol. BMC Microbiol. 2009 Aug. 18; 9:170. Thus, the strain generated has deletions in the Suwwan region, msbB and zwf. In *S. montevideo*, where the Suwwan mutation is not known to occur, a pCVD442 vector is used to generate the equivalent mutation, together with the same procedures above (altered as necessary for DNA sequence variations in the DNA portions used for homologous recombination), resulting in a pair of strains having the same mutational background together with different bacterial antigens. These strains, alone or used for alternating doses, form a basic platform into which the effector genes and protease inhibitor gene constructs are inserted.

8.2 Example: A Targeted Colicin E3 (colE3) Chimera

Chimeric cytotoxins are generated using standard molecular genetic techniques, including synthetic biology (e.g., chemically synthesized oligonucleotides annealed into larger constructs forming entire genes based on the nucleic acid and/or amino acid sequence selected, including codon optimization) and expressed in bacteria using methods known to those skilled in the arts, operably linking a promoter, ribosomal binding site and initiating methionine if not provided by the first portion of the construct. The upstream and downstream regions may contain a transcriptional termination signal (terminator). The construct may be inserted into an exogenous plasmid or a chromosomal or virulence (VIR; pSLT) plasmid integration vector, for which many different integration sites exist, including but not limited to any of the attenuation mutations or any defective (incomplete) phage elements, intergenic regions or the IS200 elements. The constructs may also be polycistronic, having multiple genes and/or gene products separated by ribosomal binding sites.

The colicin colE3 immunity protein is first synthesized as an expression cassette and cloned into a chromosomal localization vector for an integration site distal to the that of the intended site for the chimeric effector gene vector (FIG. 12) as described below, e.g., an IS200 deletion vector at location. The amino acid sequence of the immunity protein is given as:

```
                                         SEQ ID NO: 129
MGLKLDLTWFDKSTEDFKGEEYSKDFGDDGSVMESLGVPFKDNVNNGCFD

VIAEWVPLLQPYFNHQIDISDNEYFVSFDYRDGDW
```

The sequence is reverse translated using codons optimal for *Salmonella*. The entire chimeric effector protein and expression cassette components are synthesized using standard DNA synthesis techniques at a contract DNA synthesis facility and integrated into the chromosome (Donnenberg and Kaper, 1991 Infect Immun 59: 4310-4317, Low et al., 2004, Methods in Molecular Medicine 90: 47-60, each of which is expressly incorporated herein by reference). The recipient stain can be any tumor-targeted bacterium.

This example of a chimeric colicin follows the pattern shown in FIG. 3A. This chimera is targeted to cancer cells over-expressing EGFR via a TGF-alpha ligand. The chimera consists of the M13 filimenous phage pIII protein 18 amino acid signal sequence, followed by the natural alanine and a 3 glycine spacer. The spacer is followed by the mature 50 amino acid peptide for TGF-alpha, the remaining pIII protein truncated after amino acid 372 of pIII, followed by the enzymatically active (ribonuclease) C-terminus of colicin E3, followed by a stop signal. The complete amino acid sequence is:

```
                                         SEQ ID NO: 130
MKKLLFAIPLVVPFYSHSAGGGVVSHFNDCPDSHTQFCFHGTCRFLVQED

KPACVCHSGYVGARCEHADLLAAETVESCLAKSHTENSFTNVWKDDKTLD

RYANYEGCLWNATGVVVCTGDETQCYGTWVPIGLAIPENEGGGSEGGGSE

GGGSEGGGTKPPEYGDTPIPGYTYINPLDGTYPPGTEQNPANPNPSLEES

QPLNTFMFQNNRFRNRQGALTVYTGTVTQGTDPVKTYYQYTPVSSKAMYD

AYWNGKFRDCAFHSGFNEDLFVCEYQGQSSDLPQPPVNAGGGSGGGSGGG

SEGGGSEGGGSEGGGSEGGGSGGGSGSGDFDYEKMANANKGAMTENADEN

ALQSDAKGKLDSVATDYGAAIDGFIGDVSGLANGNGATGDFAGSNSQMAQ

VGDGDNSPLMNNFRQYLPSLPQSVECRFAHDPMAGGHRMWQMAGLKAQRA

QTDVNNKQAAFDAAAKEKSDADAALSSAMESRKKKEDKKRSAENNLNDEK

NKPRKGFKDYGHDYHPAPKTENIKGLGDLKPGIPKTPKQNGGGKRKRWTG

DKGRKIYEWDSQHGELEGYRASDGQHLGSFDPKTGNQLKGPDPKRNIKKY

L*
```

The entire chimeric effector protein and expression cassette components are synthesized using standard DNA synthesis techniques, for example, at a contract DNA synthesis facility, and cloned into a chromosomal localization vector, e.g., an IS200 deletion vector, and integrated into the chromosome (Donnenberg and Kaper, 1991, Low et al., 2003, each of which is expressly incorporated herein by reference).

8.3 Example: A Targeted Colicin Chimera Containing a Lytic Peptide Resulting in Endosomal Release and/or Increased Anti-Cancer Cell Cytotoxicity The lytic peptide PSM-alpha-3 is inserted between the pIII signal sequence and the TGF-alpha (FIG. 3B). The complete sequence of the construct is as follows:

```
                                         SEQ ID NO: 131
MKKLLFAIPLVVPFYSHSAMEFVAKLFKFFKDLLGKFLGNNVVSHFNDCP

DSHTQFCFHGTCRFLVQEDKPACVCHSGYVGARCEHADLLAAETVESCLA

KSHTENSFTNVWKDDKTLDRYANYEGCLWNATGVVVCTGDETQCYGTWVP

IGLAIPENEGGGSEGGGSEGGGSEGGGTKPPEYGDTPIPGYTYINPLDGT

YPPGTEQNPANPNPSLEESQPLNTFMFQNNRFRNRQGALTVYTGTVTQGT

DPVKTYYQYTPVSSKAMYDAYWNGKFRDCAFHSGFNEDLFVCEYQGQSSD
```

-continued

LPQPPVNAGGGSGGGSGGGSEGGGSEGGGSEGGGSEGGGSGGGSGSGDFD

YEKMANANKGAMTENADENALQSDAKGKLDSVATDYGAAIDGFIGDVSGL

ANGNGATGDFAGSNSQMAQVGDGDNSPLMNNFRQYLPSLPQSVECRFAHD

PMAGGHRMWQMAGLKAQRAQTDVNNKQAAFDAAAKEKSDADAALSSAMES

RKKKEDKKRSAENNLNDEKNKPRKGFKDYGHDYHPAPKTENIKGLGDLKP

GIPKTPKQNGGGKRKRWTGDKGRKIYEWDSQHGELEGYRASDGQHLGSFD

PKTGNQLKGPDPKRNIKKYL

8.4 Example: A Chimeric Colicin E7

As for the other colicin E3 constructs, the colicin colE7 immunity protein is synthesized as an expression cassette and cloned into a chromosomal localization vector for an integration site distal to the that of the chimeric effector gene vector described below, e.g., an IS200 deletion vector at location.

The genetic construct of the first colicin E7 chimera follows the same pattern as shown in FIG. 3A, except that the ColE3 C-terminus is replaced with the colE7 (a DNAase) C-terminus comprising amino acids 444 to 576 (FIG. 3 C). Nuclear localization signals (NLSs) may also be added, including but not limited to that from herpes simplex virus thymidine kinase, the SV40 large T antigen (PPKK-KRKV SEQ ID NO:1) monopartite NLS, or the nucleoplamin bipartite NLS (KR[PAATKKAGQA]KKKK SEQ ID NO:2, or more preferably, the NLS from apoptin, a tumor associated (tumor-selective) NLS. The tumor-selective nuclear export signal from apoptin may be used alone or together with NLS from apoptin.

The genetic construct of the second colicin E7 chimera follows the same pattern as shown in FIG. 3C, except that the lysis peptide is inserted between the M13pIII signal sequence and the targeting peptide (TGF-alpha) (FIG. 3D). Nuclear localization signals (NLSs) may also be added, including but not limited to that from herpes simplex virus thymidine kinase, the SV40 large T antigen (PPKKKRKV SEQ ID NO:1) monopartite NLS, or the nucleoplamin bipartite NLS (KR[PAATKKAGQA]KKKK SEQ ID NO:2, or more preferably, the NLS from apoptin, a tumor associated (tumor-selective) NLS. The tumor-selective nuclear export signal from apoptin may be used alone or together with NLS from apoptin.

8.5 Example: A Chimeric Colicin Ia

As for the other colicin E3 constructs, the colicin Ia immunity protein is synthesized as an expression cassette and cloned into a chromosomal localization vector for an integration site distal to the that of the chimeric effector gene vector described below, e.g., an IS200 deletion vector at location.

The genetic construct of the first colicin Ia chimera follows the same pattern as shown in FIG. 3A, except that the ColE3 C-terminus is replaced with the Ia (pore forming) C-terminus comprising amino acids 450 to 626 (FIG. 3 E).

The genetic construct of the second colicin Ia chimera follows the same pattern as shown in FIG. 3B, except that the lysis peptide is inserted between the M13pIII signal sequence and the targeting peptide (TGF-alpha) (FIG. 3F).

8.6 Example: Colicin TRC Fusions

Colicin TRC fusions utilize the entire colicin with its three domains, T (translocation), R (receptor), and C (catalytic), and fuse active moieties to the C-terminal catalytic domain (FIG. 4). A) TRC of a colicin, such as colE3, and a targeting domain, such as TGF-alpha. B) TRC of a colicin, such as colE3, a lytic peptide such as PSM-alpha-1, and a targeting domain, such as TGF-alpha. The lytic peptide may be engineered to have protease cleavage sites, such as those from cathepsin, that effect its release and aid in escape from an endosome. C) TRC of a DNAase colicin, such as colE9 where it is desirable to direct the DNAase activity to the tumor, a nuclear localization domain (NLS), preferably that of Apoptin, and a targeting domain such as a CD22 binding peptide. The CD22 peptide is disulfide bonded (S—S) loop. Alternatively, a peptide library such as are used in phage display, including those using disulfide bonding may be used. Such libraries are may be first selected using phage, or may alternatively first be selected by screening of colicins for target cell specificity and then transferred to the colicin receptor region. In addition, a library of the "tol box" penta peptide (DGSGW SEQ ID NO:133) variations and/or extended tolB box (DGSGWSSENNPWGGGSGSIHW SEQ ID NO:134; Hands et al., 2005, Interactions of TolB with the translocation domain of colicin E9 require and extended tolB box, J Bacteriol. 187: 6733-6741) variations may be screened alone or in combination with individual receptor peptides such as the CD22 binding peptide, or a library of receptor peptides and a library of tol box or extended tol box peptides may be screened in combination. D) TRC of a DNAase colicin, such as colE9 where it is desirable to direct the DNAase activity to the tumor, a nuclear localization domain (NLS), preferably that of Apoptin, a lytic peptide such as PSM-alpha-1, and a targeting domain, such as a CD22 binding peptide. The lytic peptide may be engineered to have protease cleavage sites, such as those from cathepsin, that affects its release and aids in escape of the colicin chimera from an endosome. E) TRC of colicin E3, a ribonuclease colicin active in the cytoplasm, where a targeting peptide, such as CD22 binding peptide, is inserted into the targeting domain, between amino acids 374 and 391. F) TRC of colicin E3, a ribonuclease colicin active in the cytoplasm, where a targeting peptide, such as CD22 binding peptide, is inserted into the targeting domain between amino acids 374 and 391 and a lytic peptide is engineered in-frame. The lytic peptide may be engineered to have a protease cleavage site, such as those from a cathepsin, that affects its release and aids in escape of the colicin chimera from an endosome. G) TRC of colicin E9, a DNAase colicin active in the nucleus, where a targeting peptide, such as CD22 binding peptide, is inserted into the targeting domain. H) TRC of colicin E9, a DNAase colicin active in the nucleus, where a targeting peptide, such as CD22 binding peptide, is inserted into the targeting domain. and a lytic peptide is engineered in-frame. The lytic peptide may be engineered to have a protease cleavage site, such as those from a cathepsin, that affects its release and aids in escape of the colicin chimera from an endosome.

8.7. Example: Selecting Protease Inhibitors

Protease inhibitors are generated using knowledge of the predicted proteolytic cleavage of the effector molecule (e.g., ProP 1.0, Duckert et al., 2004, Prediction of proprotein convertase cleavage sites, Protein Engineering Design and Selection 17: 107-122; ExPASy PeptideCutter tool, Gasteiger et al. Protein Identification and Analysis Tools on the ExPASy Server, In: John M. Walker (ed): The Proteomics Protocols Handbook, Humana Press, 2005), and may be used to test the predicted proteolytic sensitivity of the effector molecule. Using the colicin lytic peptide TGF fusion described above, the Duckert et al., method predicts a furin cleavage at amino acid 509. Thus, since cleavage of the effector molecule has the potential to occur, furin represent a protease target for which inhibition could improve the effectiveness or activity of a co-expressed molecule by inhibiting its destruction by proteolytic degradation, whereas Factor Xa is identified by ProP as a cleavage site that is not present, does not need to be inhibited, and who's cleavage recognition site could be added between protein domains where removal of a domain by proteolysis is desirable.

8.8. Example: Secreted Protease Inhibitors

Secreted protease inhibitors are generated using standard molecular genetic techniques and expressed in bacteria using methods known to those skilled in the arts, operably linking a promoter, ribosomal binding site and initiating methionine if not provided by the first portion of the construct. The construct may either be a plasmid or a chromosomal virulence (VIR) plasmid integration vector, for which many different integration sites exist, including but not limited to any of the attenuation mutations, intergenic regions or any of the IS200 elements. The constructs may also be polycistronic, having multiple genes and/or gene products separated by ribosomal binding sites. The different forms of the protease inhibitor constructs are shown in FIG. 2. The constructs used have multiple forms, for example:

1) An N-terminal signal sequence, such as that from M13pIII MKKLLFAIPLVVPFYSHS SEQ ID NO:135, followed by a protease inhibitor such as the furin inhibitor GKRPRAKRA SEQ ID NO:11;
2) a protease inhibitor such as the furin inhibitor GKRPRAKRA SEQ ID NO:11 followed by the C-terminal signal sequence of hlyA STYGSQDYLNPLINEISKI-ISAAGNLDVKEERSAASLLQLSGNASDFSYGRNSITL-TASA SEQ ID NO:136, or
3) a protease inhibitor such as the furin inhibitor GKRPRAKRA SEQ ID NO:11, followed by a furin cleavage signal RXKR↓SX SEQ ID NO:137 followed by the C-terminal signal sequence of hlyA STYGSQDYLN-PLINEISKIISAAGNLDVKEERSAASLLQLSGNASDF-SYGRNSITLTASA SEQ ID NO:138

8.9 Example 6: Expression of a C-Terminal Amidating Enzyme Required to Post-Translationally Modify Gastrin and Bombesin Targeting Peptides A C-terminal amidating enzyme composition known form serum or plasma which comprises a C-terminal amidating enzyme capable of amidating a C-terminal glycine which amidates the carboxy terminus of the C-terminal glycine of a peptide terminating in Gly-Gly. The enzyme participating in such amidation is called peptidylglycine-α-amidating monoxygenase (C-terminal amidating enzyme) (EC.1.14.17.3) (Bradbury et al, Nature, 298, 686, 1982: Glembotski et al, J. Biol, Chem., 259, 6385, 1984; and U.S. Pat. No. 5,354,675, expressly incorporated herein by reference), is considered to catalyze the following reaction:

—CHCONHCH$_2$COOH—CHCONH$_2$+glyoxylic acid is produced by the recombinant.

8.10 Example: Expression of Antitumor Lytic Peptides

Examples of antitumor lytic peptides are shown in FIG. 5. It is understood that those peptides utilizing the hlyA signal sequence requires hlyBD in trans together with a functional tolC. The lytic peptide constructs consist of A) lytic peptide joined to the HlyA signal sequence, B) lytic peptide, targeting peptide, signals sequence, C) M13 pIII signal sequence, lytic peptide, M13 pIII amino acids 19 to 372, targeting peptide, D) M13 signal sequence, lytic peptide, targeting peptide, M13 pIII amino acids 19 to 372.

8.11 Example: Expression of Antitumor Lytic Peptide Prodrugs

Examples of antitumor lytic peptide prodrugs are shown in FIG. 6. It is understood that those peptides utilizing the hlyA signal sequence requires hlyBD in trans together with a functional tolC. The lytic peptide prodrug constructs consist of A) a neutral (e.g., beta sheet) blocking peptide of 50 amino acids, a protease cleavage site shown by downward arrow (for a protease not being blocked by a protease inhibitor), a lytic peptide, and the hlyA signal sequence, which may contain the same protease cleavage site shown by a downward arrow, B) a neutral (e.g., beta sheet) blocking peptide of 50 amino acids, a lytic peptide, a targeting peptide (e.g., TGF-alpha), a protease cleavage site shown by downward arrow (for a protease not being blocked by a protease inhibitor), and the hlyA signal sequence, which may contain the same protease cleavage site shown by a downward arrow, C) the M13 pIII signal sequence, a blocking peptide, a protease cleavage sequence, a lytic peptide, M13 pIII amino acids 19 to 372, and a targeting peptide (e.g., TGF-alpha), and D) the M13 pIII signal sequence, a blocking peptide, a protease cleavage sequence, a lytic peptide, a targeting peptide (e.g., TGF-alpha), and M13 pIII amino acids 19 to 372.

8.12 Example: Cytolethal Distending Toxin cltdB Fusion with Apoptin (FIG. 6)

A cytolethal distending toxin subunit B with tumor-specific nuclear localization and normal cell nuclear export is generated by a fusion with apoptin containing a five glycine linker in between (FIG. 6A). The complete sequence of the construct is as follows:

SEQ ID NO: 139
MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGMNALQEDTPPGPSTVFRPPTSSRPLE

TPHCREIRIGIAGITITLSLCGCANARAPTLRSATADNSESTGFKNVPDL

RTDQPKPPSKKRSCDPSEYRVSELKESLITTTPSRPRTAKRRIRL

8.13 Example: Cytolethal Distending Toxin cltdB Fusion with a Truncated Apoptin A cytolethal distending toxin subunit B with tumor-specific nuclear localization and normal cell nuclear export is generated by a fusion with a truncated apoptin amino acids 33 to 121 containing a five glycine linker in between (FIG. 6B). The complete sequence of the construct is as follows:

SEQ ID NO: 140
MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGITPHCREIRIGIAGITITLSLCGCAN

ARAPTLRSATADNSESTGFKNVPDLRTDQPKPPSKKRSCDPSEYRVSELK

ESLITTTPSRPRTAKRRIRL

8.14 Example: Cytolethal Distending Toxin cltdB Fusion with a Truncated Apoptin A cytolethal distending toxin subunit B with tumor-specific nuclear retention signal is generated by a fusion with a truncated apoptin amino acids 33 to 46 containing a five glycine linker in between (FIG. 6C). The complete sequence of the construct is as follows:

SEQ ID NO: 141
MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGIRIGIAGITITLSL

8.15 Example: Cytolethal Distending Toxin cltdB Fusion with a Truncated Apoptin A cytolethal distending toxin subunit B with a normal cell nuclear export signal is generated by a fusion with a truncated apoptin amino acids 81 to 121 containing a five glycine linker in between (FIG. 6D). The complete sequence of the construct is as follows:

SEQ ID NO: 142
MKKYIISLIVFLSFYAQADLTDFRVATWNLQGASATTESKWNINVRQLIS

GENAVDILAVQEAGSPPSTAVDTGTLIPSPGIPVRELIWNLSTNSRPQQV

YIYFSAVDALGGRVNLALVSNRRADEVFVLSPVRQGGRPLLGIRIGNDAF

FTAHAIAMRNNDAPALVEEVYNFFRDSRDPVHQALNWMILGDFNREPADL

EMNLTVPVRRASEIISPAAATQTSQRTLDYAVAGNSVAFRPSPLQAGIVY

GARRTQISSDHFPVGVSRRGGGGGTDQPKPPSKKRSCDPSEYRVSELKES

LITTTPSRPRTAKRRIRL

8.16 Example: Exchange of the Variable Loop in cldtB to Enhance Activity

The amino acid sequence FRDSRDPVHQAL SEQ ID NO:143 which is associated with dimerization and inactivation can be exchanged for the loop NSSSSPPERRVY SEQ ID NO:144 from *Haemophilus* which is associated with stabile retention of cytotoxicty.

8.17 Example: Expression of Repeat in Toxin (RTX) Family Members

RTX family members, including *E. coli* hemolysin operon hlyCABD and *Actinobacillus actinomycetemcomitans* leucotoxin ltxCABD are expressed in coordination with protease inhibitors as shown in FIG. 7. *E coli* hemolysin operon hlyCABD is expressed as a non-chimera (FIG. 7A). *Actinobacillus actinomycetemcomitans* leucotoxin ltxCABD operon is expressed as either a non-hybrid (FIG. 7B) or as a hybrid (FIG. 7C). It is understood that a functional tolC gene is required in the gram-negative bacterial strain for functional expression of each of these operons, or that homologs such as prtF and/or cyaE may be used.

8.18 Example: A Group B *Streptococcus* Expressing a Vascular-Targeted Lytic Peptide A low pathogenicity clyE⁻ group B *Streptococcus* expressing a gram positive secretion signal from alkaline phosphatase (Lee et al., 1999 J. Bacteriol, 181: 5790-5799) in frame with the vascular targeting peptide F3 CKDEPQRRSARLSAKPAPPKPEPKPKKAPAKK SEQ ID NO:145 in frame with the lytic peptide PSM-α-3.

8.19 Example: A Group B *Streptococcus* Expressing a Vascular-Targeted Toxin A low pathogenicity clyE⁻ group B *Streptococcus* expressing a gram positive secretion signal from alkaline phosphatase (Lee et al., 1999 J. Bacteriol, 181: 5790-5799) in frame with saporin and the vascular targeting peptide F3 CKDEPQRRSARLSAKPAPPKPEPKPKKAPAKK SEQ ID NO: 146 (FIG. 7).

It will be understood that the foregoing is only illustrative of the principles of the invention, and that various modifications can be made by those skilled in the art without departing from the scope and spirit of the invention.

---

What is claimed is:

1. A method of treating a human or animal for a neoplasia, in need of treatment, comprising:
    administering a genetically engineered *Salmonella* bacterium to a human or animal, that co-expresses a heterologous protease sensitive therapeutic molecule for the neoplasia, which is distinct from a protease inhibitor, and a heterologous protease inhibitor; and
    permitting the genetically engineered bacterium to grow within a common target tissue of the human or animal, wherein the heterologous protease sensitive therapeutic molecule is effective to treat the human or animal for the neoplasia of the common target tissue, and
    the protease inhibitor is effective to delay degradation of the heterologous protease sensitive therapeutic molecule in the common target tissue.

2. The method according to claim 1, wherein the common target tissue is a solid tumor.

3. The method according to claim 1, wherein the common target tissue is bone marrow.

4. The method according to claim 3, wherein the common target tissue is selected from the group consisting of at least one of leukemia cells, lymphoma cells, and multiple myeloma cells.

5. The method according to claim 1 where the heterologous protease sensitive therapeutic molecule is selected from the group consisting of a chimeric toxin, a cytokine, an antibody, a bispecific antibody, a single chain antibody, a chemokine, and a prodrug converting enzyme.

6. The method according to claim 1, wherein the heterologous protease sensitive therapeutic molecule comprises a toxin selected from the group consisting of cytolethal distending toxin (cldt), cytotoxic nectrotic factor (cnf), dermonecrotic factor (dmf), shiga toxin, shiga-like toxin, colicins, membrane lytic peptides from *Staphalococcus*, leucotoxin, a leuckotoxin:HlyA hybrid, heat stable enterotoxin from enterobacteriaceae, an autotransporter toxin, chlostridium enterotoxin, aerolysin, typhoid toxin, subtilase, *Bordetella* adenylate cyclase toxin, pertussus toxin, and porB.

7. The method according to claim 1, wherein the heterologous protease sensitive therapeutic molecule comprises at least one of a cytolethal distending toxin (cldt) and a typhoid toxin fused to a peptide containing a nuclear localization signal from apoptin.

8. The method according to claim 1, wherein the protease inhibitor is secreted from the genetically engineered *Salmonella* bacterium, effective for achieving a targeting of the heterologous protease sensitive therapeutic or molecule to the common target tissue having the neoplasia, with respect to non-target tissues of the human or animal.

9. The method according to claim 1, wherein the heterologous protease sensitive therapeutic molecule comprises a colicin fused to a targeting peptide.

10. The method according to claim 1, wherein the heterologous protease sensitive therapeutic molecule comprises a targeting peptide effective for targeting cells within the common target tissue having the neoplasia.

11. The method according to the claim 1, wherein the heterologous protease inhibitor is a furin inhibitor selected from one or more of the group consisting of:

PAAATVTKKVAKSPKKAKAAKPKKAAK-
SAAKAVKPK SEQ ID NO:8
TKKVAKRPRAKRAA SEQ ID NO:9
TKKVAKRPRAKRDL SEQ ID NO:10
GKRPRAKRA SEQ ID NO:11
CKRPRAKRDL SEQ ID NO:12
CVAKRPRAKRDL SEQ ID NO:13
CKKVAKRPRAKRDL SEQ ID NO:14
RRRRRR SEQ ID NO:15.

12. A method of treating a disease selected from one or more of the group consisting of a neoplasia and a cancer, in a human or mammal, comprising administering a pharmaceutically acceptable formulation to the human or mammal, comprising a *Salmonella* genetically engineered live bacterium that co-expresses:

(a) a heterologous protease sensitive therapeutic molecule which is distinct from a protease inhibitor, and (b) a heterologous protease inhibitor, within a target tissue after administration to the human or mammal, and permitting the *Salmonella* genetically engineered live bacterium to replicate within the target tissue of the human or mammal associated with the disease selected from one or more of the group consisting of the neoplasia and the cancer which produces a protease effective for degrading the heterologous protease sensitive therapeutic molecule in an absence of an effective amount of a protease inhibitor, to produce in situ the heterologous protease sensitive therapeutic molecule in the effective amount and the heterologous protease inhibitor.

13. The method according to claim 12, wherein the heterologous protease sensitive therapeutic molecule has antineoplastic effects, and the target tissue comprises a tumor.

14. The method according to claim 12, wherein the heterologous protease sensitive therapeutic molecule is selected from the group consisting of a chimeric toxin, cytokine, antibody, bispecific antibody, single chain antibody, chemokine, and prodrug converting enzyme.

15. The method according to claim 12, wherein the heterologous protease sensitive therapeutic molecule is a chimeric toxin formed of at least a toxin moiety and a secretion peptide.

16. The method engineered bacterium according to claim 12, wherein the heterologous protease sensitive therapeutic molecule is colicin col-Ia or colE7 in which targeting and translocation sequences are replaced with an M13 pIII signal sequence fused to a targeting peptide, followed by M13, and a membrane anchor-truncated M13 pIII, fused to the C-terminal catalytic portion of col-Ia or colE7, respectively, the targeting peptide is the mature form of TGF-alpha, and a *Staphalococcus* lytic peptide is inserted between the M13 pIII signal sequence and the targeting peptide.

17. A method of treating a human having a pathological tissue comprising a neoplastic tissue, comprising:

administering a *Salmonella* genetically engineered live bacteria to the human; and permitting the *Salmonella* genetically engineered live bacteria to selectively replicate within the pathological tissue, and to produce within the pathological tissue both a heterologous protease-sensitive cytotoxic molecule distinct from a protease inhibitor, and a heterologous protease inhibitor, wherein endogenous proteases within the pathological tissue are delayed from degrading the heterologous protease sensitive cytotoxic molecule within the pathological tissue by a presence of a sufficient amount of the heterologous protease inhibitor produced by the *Salmonella* genetically engineered live bacteria, and the heterologous protease sensitive cytotoxic molecule exerts a cytotoxic effect against the pathological tissue, and wherein endogenous proteases within a tissue surrounding the pathological tissue are exposed to a sufficiently low concentration of the heterologous protease inhibitor produced by the *Salmonella* genetically engineered live bacteria, to permit degradation of the heterologous protease sensitive cytotoxic molecule produced by the *Salmonella* genetically engineered live bacteria, to thereby decrease cytotoxicity and increase a selectivity of action of the heterologous protease-sensitive cytotoxic molecule against the pathological tissue with respect to the tissue surrounding the pathological tissue.

18. The method according to claim 17, wherein the heterologous protease sensitive cytotoxic molecule comprises a fusion protein.

19. The method according to claim 17, wherein the *Salmonella* genetically engineered live bacteria comprises a genetically engineered gene which encodes and causes the *Salmonella* genetically engineered live bacterium to produce a chimeric peptide comprising:

the heterologous protease sensitive cytotoxic molecule, the heterologous protease inhibitor, at least one of a secretion peptide and a targeting peptide, and at least one intervening protease cleavage site distinct from the heterologous protease sensitive cytotoxic molecule, the heterologous protease inhibitor, and the at least one of a secretion peptide and a targeting peptide.

* * * * *

SEQUENCE LISTING

<160> NUMBER OF SEQ ID NOS: 171

<210> SEQ ID NO 1
<211> LENGTH: 8
<212> TYPE: PRT
<213> ORGANISM: Simian virus 40

<400> SEQUENCE: 1

```
Pro Pro Lys Lys Lys Arg Lys Val
1               5

<210> SEQ ID NO 2
<211> LENGTH: 16
<212> TYPE: PRT
<213> ORGANISM: Simian virus 40

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: furin cleavage site
<220> FEATURE:
<221> NAME/KEY: X
<222> LOCATION: (2)..(6)
<223> OTHER INFORMATION: X can be any naturally occurring amino acid
<220> FEATURE:
<221> NAME/KEY: Variant
<222> LOCATION: (2)..(6)
<223> OTHER INFORMATION: X can be any naturally occurring amino acid

<400> SEQUENCE: 3

Arg Xaa Lys Arg Ser Xaa
1               5

<210> SEQ ID NO 4
<211> LENGTH: 10
<212> TYPE: PRT
<213> ORGANISM: Streptococcus agalactiae
<220> FEATURE:
<221> NAME/KEY: X
<222> LOCATION: (1)..(9)
<223> OTHER INFORMATION: X can be leucine or isoleucine
<220> FEATURE:
<221> NAME/KEY: X
<222> LOCATION: (1)..(1)
<223> OTHER INFORMATION: X can be leucine or isoleucine
<220> FEATURE:
<221> NAME/KEY: X
<222> LOCATION: (9)..(9)
<223> OTHER INFORMATION: X can be leucine or isoleucine
<220> FEATURE:
<221> NAME/KEY: Variant
<222> LOCATION: (9)..(9)
<223> OTHER INFORMATION: X can be leucine or isoleucine

<400> SEQUENCE: 4

Xaa Asp Gly Glx Ala Glu Phe Leu Xaa Lys
1               5                   10

<210> SEQ ID NO 5
<211> LENGTH: 58
<212> TYPE: PRT
<213> ORGANISM: Artificial Sequence
<220> FEATURE:
<223> OTHER INFORMATION: Aprotinin

<400> SEQUENCE: 5

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
                20                  25                  30
```

-continued

Phe Val Tyr Gly Gly Cys Arg Ala Lys Arg Asn Asn Phe Lys Ser Ala
            35                  40                  45

Glu Asp Cys Met Arg Thr Cys Gly Gly Ala
    50                  55

<210> SEQ ID NO 6
<211> LENGTH: 14
<212> TYPE: PRT
<213> ORGANISM: Artificial Sequence
<220> FEATURE:
<223> OTHER INFORMATION: Proteaqse Inhibitor 15, corresponding to amino
      acids 245-258 of human protease inhibitor (trypsin)

<400> SEQUENCE: 6

Cys Phe Pro Gly Val Thr Ser Asn Tyr Leu Tyr Trp Phe Lys
1               5                   10

<210> SEQ ID NO 7
<211> LENGTH: 56
<212> TYPE: PRT
<213> ORGANISM: Artificial Sequence
<220> FEATURE:
<223> OTHER INFORMATION: Serine protease inhibitor, Kazal type 1, mature

<400> SEQUENCE: 7

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 8
<211> LENGTH: 36
<212> TYPE: PRT
<213> ORGANISM: Artificial Sequence
<220> FEATURE:
<223> OTHER INFORMATION: Furin inhibitor

<400> SEQUENCE: 8

Pro Ala Ala Ala Thr Val Thr Lys Lys Val Ala Lys Ser Pro Lys Lys
1               5                   10                  15

Ala Lys Ala Ala Lys Pro Lys Lys Ala Ala Lys Ser Ala Ala Lys Ala
            20                  25                  30

Val Lys Pro Lys
            35

<210> SEQ ID NO 9
<211> LENGTH: 14
<212> TYPE: PRT
<213> ORGANISM: Artificial Sequence
<220> FEATURE:
<223> OTHER INFORMATION: Furin inhibitor

<400> SEQUENCE: 9

Thr Lys Lys Val Ala Lys Arg Pro Arg Ala Lys Arg Ala Ala
1               5                   10

<210> SEQ ID NO 10
<211> LENGTH: 14
<212> TYPE: PRT
<213> ORGANISM: Artificial Sequence

```
<220> FEATURE:
<223> OTHER INFORMATION: Furin inhibitor

<400> SEQUENCE: 10

Thr Lys Lys Val Ala Lys Arg Pro Arg Ala Lys Arg Asp Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Furin inhibitor

<400> SEQUENCE: 11

Gly Lys Arg Pro Arg Ala Lys Arg Ala
1               5

<210> SEQ ID NO 12
<211> LENGTH: 10
<212> TYPE: PRT
<213> ORGANISM: Artificial Sequence
<220> FEATURE:
<223> OTHER INFORMATION: Furin inhibitor

<400> SEQUENCE: 12

Cys Lys Arg Pro Arg Ala Lys Arg Asp Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Furin inhibitor

<400> SEQUENCE: 13

Cys Val Ala Lys Arg Pro Arg Ala Lys Arg Asp Leu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Furin inhibitor

<400> SEQUENCE: 14

Cys Lys Lys Val Ala Lys Arg Pro Arg Ala Lys Arg Asp Leu
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Hexa-L-arginine furin inhibitor

<400> SEQUENCE: 15

Arg Arg Arg Arg Arg Arg
1               5

<210> SEQ ID NO 16
<211> LENGTH: 10
<212> TYPE: PRT
<213> ORGANISM: Artificial Sequence
<220> FEATURE:
```

<223> OTHER INFORMATION: Kallikrein 2 Inhibitor

<400> SEQUENCE: 16

Ser Arg Phe Lys Val Trp Trp Ala Ala Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Kallikrein 2 Inhibitor

<400> SEQUENCE: 17

Ala Ala Arg Arg Pro Phe Pro Ala Pro Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Kallikrein 2 Inhibitor

<400> SEQUENCE: 18

Pro Ala Arg Arg Pro Phe Pro Val Thr Ala
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Pepsinogen 1-16 pepsin inhibitor

<400> SEQUENCE: 19

Leu Val Lys Val Pro Leu Val Arg Lys Lys Ser Leu Arg Gln Asn Leu
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Pepsinogen 1-12 pepsin inhibitor

<400> SEQUENCE: 20

Leu Val Lys Val Pro Leu Val Arg Lys Lys Ser Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Pepsinogen 1-12 4-7 substitution [Gly4,5]

<400> SEQUENCE: 21

Leu Val Lys Gly Gly Leu Val Arg Lys Lys Ser Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Pepsinogen 1-12 4-7 substitution [Gly 6,7]

<400> SEQUENCE: 22

Leu Val Lys Val Pro Gly Gly Arg Lys Lys Ser Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Pepsinogen 1-12 4-7 substitution [Gly 4-7]

<400> SEQUENCE: 23

Leu Val Lys Gly Gly Gly Gly Arg Lys Lys Ser Leu
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Sunflower trypsin inhibitor SFTI-1

<400> SEQUENCE: 24

Gly Arg Cys Thr Lys Ser Ile Pro Pro Ile Cys Phe Pro Asp
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Odorrana trypsin inhibitor

<400> SEQUENCE: 25

Ala Val Asn Ile Pro Phe Lys Val His Phe Arg Cys Lys Ala Ala Phe
1               5                   10                  15

Cys

<210> SEQ ID NO 26
<211> LENGTH: 61
<212> TYPE: PRT
<213> ORGANISM: Artificial Sequence
<220> FEATURE:
<223> OTHER INFORMATION: Ascaris chymotrypsin elastase inhibitor

<400> SEQUENCE: 26

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
                20                  25                  30

Cys Arg Arg Pro Ser Cys Glu Cys Ser Pro Gly Arg Gly Met Arg Arg
            35                  40                  45

Thr Asn Asp Gly Lys Cys Ile Pro Ala Ser Gln Cys Pro
        50                  55                  60

<210> SEQ ID NO 27
<211> LENGTH: 66
<212> TYPE: PRT
<213> ORGANISM: Artificial Sequence
<220> FEATURE:
<223> OTHER INFORMATION: Ascaris trypsin inhibitor

<400> SEQUENCE: 27

Glu Ala Glu Lys Cys Asx Glx Glx Pro Gly Trp Thr Lys Gly Gly Cys
1               5                   10                  15

Glu Thr Cys Gly Cys Ala Gln Lys Ile Val Pro Cys Thr Arg Glu Thr
            20                  25                  30

Lys Pro Asn Pro Gln Cys Pro Arg Lys Gln Cys Cys Ile Ala Ser Ala
            35                  40                  45

Gly Phe Val Arg Asp Ala Gln Gly Asn Cys Ile Lys Phe Glu Asp Cys
    50                  55                  60

Pro Lys
65

<210> SEQ ID NO 28
<211> LENGTH: 62
<212> TYPE: PRT
<213> ORGANISM: Artificial Sequence
<220> FEATURE:
<223> OTHER INFORMATION: Ascaris trypsin inhibitor

<400> SEQUENCE: 28

Glu Ala Glu Lys Cys Thr Lys Pro Asn Glu Gln Trp Thr Lys Cys Gly
1               5                   10                  15

Gly Cys Glu Gly Thr Cys Ala Gln Lys Ile Val Pro Cys Thr Arg Glu
            20                  25                  30

Cys Lys Pro Pro Arg Cys Glu Cys Ile Ala Ser Ala Gly Phe Val Arg
            35                  40                  45

Asp Ala Gln Gly Asn Cys Ile Lys Phe Glu Asp Cys Pro Lys
    50                  55                  60

<210> SEQ ID NO 29
<211> LENGTH: 101
<212> TYPE: PRT
<213> ORGANISM: Artificial Sequence
<220> FEATURE:
<223> OTHER INFORMATION: Onion trypsin inhibitor

<400> SEQUENCE: 29

Met Lys Ala Ala Leu Val Ile Phe Leu Leu Ile Ala Met Leu Gly Val
1               5                   10                  15

Leu Ala Ala Glu Ala Tyr Pro Asn Leu Arg Gln Val Val Thr Gly
            20                  25                  30

Asp Glu Glu Gly Gly Cys Cys Asp Ser Cys Gly Ser Cys Asp Arg
            35                  40                  45

Arg Ala Pro Asp Leu Ala Arg Cys Glu Cys Arg Asp Val Val Thr Ser
    50                  55                  60

Cys Gly Pro Gly Cys Lys Arg Cys Glu Glu Ala Asp Leu Asp Leu Asn
65                  70                  75                  80

Pro Pro Arg Tyr Val Cys Lys Asp Met Ser Phe His Ser Cys Gln Thr
            85                  90                  95

Arg Cys Ser Ile Leu
            100

<210> SEQ ID NO 30
<211> LENGTH: 84
<212> TYPE: PRT
<213> ORGANISM: Artificial Sequence
<220> FEATURE:
<223> OTHER INFORMATION: Barley chymotrypsin inhibitor 2

<400> SEQUENCE: 30

Met Ser Ser Met Glu Lys Lys Pro Glu Gly Val Asn Ile Gly Ala Gly

```
                1               5                  10                  15
Asp Arg Gln Asn Gln Lys Thr Glu Trp Pro Glu Leu Val Gly Lys Ser
               20                  25                  30
Val Glu Glu Ala Lys Lys Val Ile Leu Gln Asp Lys Pro Ala Ala Gln
            35                  40                  45
Ile Ile Val Leu Pro Val Gly Thr Ile Val Thr Met Glu Tyr Arg Ile
         50                  55                  60
Asp Arg Val Arg Leu Phe Val Asp Arg Leu Asp Asn Ile Ala Gln Val
65                  70                  75                  80
Pro Arg Val Gly

<210> SEQ ID NO 31
<211> LENGTH: 4
<212> TYPE: PRT
<213> ORGANISM: Artificial Sequence
<220> FEATURE:
<223> OTHER INFORMATION: Thrombin inhibitor

<400> SEQUENCE: 31

Ile Gln Pro Arg
1

<210> SEQ ID NO 32
<211> LENGTH: 6
<212> TYPE: PRT
<213> ORGANISM: Artificial Sequence
<220> FEATURE:
<223> OTHER INFORMATION: Thrombin inhibitor

<400> SEQUENCE: 32

Gly Ser Ala Val Pro Arg
1               5

<210> SEQ ID NO 33
<211> LENGTH: 15
<212> TYPE: PRT
<213> ORGANISM: Artificial Sequence
<220> FEATURE:
<223> OTHER INFORMATION: CG-Beta

<400> SEQUENCE: 33

Ser Tyr Ala Val Ala Leu Ser Cys Gln Cys Ala Leu Cys Arg Arg
1               5                   10                  15

<210> SEQ ID NO 34
<211> LENGTH: 4
<212> TYPE: PRT
<213> ORGANISM: Artificial Sequence
<220> FEATURE:
<223> OTHER INFORMATION: HER2 targeting

<400> SEQUENCE: 34

Asp Ala Arg Pro
1

<210> SEQ ID NO 35
<211> LENGTH: 13
<212> TYPE: PRT
<213> ORGANISM: Artificial Sequence
<220> FEATURE:
<223> OTHER INFORMATION: CG-beta (ala truncation)

<400> SEQUENCE: 35

Ala Val Ala Leu Ser Cys Gln Cys Ala Leu Cys Arg Arg
```

```
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: LHRH

<400> SEQUENCE: 36

```
Glu His Trp Ser Tyr Gly Leu Arg Pro Gly
1               5                   10
```

<210> SEQ ID NO 37
<211> LENGTH: 8
<212> TYPE: PRT
<213> ORGANISM: Artificial Sequence
<220> FEATURE:
<223> OTHER INFORMATION: somatostatin octapeptide RC-121

<400> SEQUENCE: 37

```
Phe Cys Tyr Trp Lys Val Cys Thr
1               5
```

<210> SEQ ID NO 38
<211> LENGTH: 14
<212> TYPE: PRT
<213> ORGANISM: Artificial Sequence
<220> FEATURE:
<223> OTHER INFORMATION: Proapoptotic peptide

<400> SEQUENCE: 38

```
Lys Leu Ala Lys Leu Ala Lys Lys Leu Ala Leu Lys Leu Ala
1               5                   10
```

<210> SEQ ID NO 39
<211> LENGTH: 19
<212> TYPE: PRT
<213> ORGANISM: Artificial Sequence
<220> FEATURE:
<223> OTHER INFORMATION: Heat stable enterotoxin (ST) Mature peptide

<400> SEQUENCE: 39

```
Asn Ser Ser Asn Tyr Cys Cys Glu Leu Cys Cys Asn Pro Ala Cys Thr
1               5                   10                  15

Gly Cys Tyr
```

<210> SEQ ID NO 40
<211> LENGTH: 60
<212> TYPE: PRT
<213> ORGANISM: Artificial Sequence
<220> FEATURE:
<223> OTHER INFORMATION: Heat stable enterotoxin unprocessed targeting

<400> SEQUENCE: 40

```
Val Leu Ser Phe Ser Pro Phe Ala Gln Asp Ala Lys Pro Val Glu Ser
1               5                   10                  15

Ser Lys Glu Lys Ile Thr Leu Glu Ser Lys Lys Cys Asn Ile Ala Lys
            20                  25                  30

Lys Ser Asn Lys Ser Asp Pro Glu Ser Met Asn Ser Ser Asn Tyr Cys
            35                  40                  45

Cys Glu Leu Cys Cys Asn Pro Ala Cys Thr Gly Cys
        50                  55                  60
```

```
<210> SEQ ID NO 41
<211> LENGTH: 9
<212> TYPE: PRT
<213> ORGANISM: Artificial Sequence
<220> FEATURE:
<223> OTHER INFORMATION: RGD 4C: active peptide targeting the V-beta-3
      integrin

<400> SEQUENCE: 41

Cys Asp Cys Arg Gly Asp Cys Phe Cys
1               5

<210> SEQ ID NO 42
<211> LENGTH: 33
<212> TYPE: PRT
<213> ORGANISM: Artificial Sequence
<220> FEATURE:
<223> OTHER INFORMATION: gastrin-34 or big gastrin

<400> SEQUENCE: 42

Leu Gly Pro Gln Gly Pro Pro His Leu Val Ala Asp Pro Ser Lys Lys
1               5                   10                  15

Gln Gly Pro Trp Leu Glu Glu Glu Glu Ala Tyr Gly Trp Met Asp
            20                  25                  30

Phe

<210> SEQ ID NO 43
<211> LENGTH: 6
<212> TYPE: PRT
<213> ORGANISM: Artificial Sequence
<220> FEATURE:
<223> OTHER INFORMATION: N-terminal truncation of gastrin

<400> SEQUENCE: 43

Met Gly Trp Met Asp Phe
1               5

<210> SEQ ID NO 44
<211> LENGTH: 14
<212> TYPE: PRT
<213> ORGANISM: Artificial Sequence
<220> FEATURE:
<223> OTHER INFORMATION: Targets gastrin releasing peptide

<400> SEQUENCE: 44

Val Pro Leu Pro Ala Gly Gly Gly Thr Val Leu Thr Lys Met
1               5                   10

<210> SEQ ID NO 45
<211> LENGTH: 13
<212> TYPE: PRT
<213> ORGANISM: Artificial Sequence
<220> FEATURE:
<223> OTHER INFORMATION: targets gastrin releasing peptide

<400> SEQUENCE: 45

Tyr Pro Arg Gly Asn His Trp Ala Val Gly His Leu Met
1               5                   10

<210> SEQ ID NO 46
<211> LENGTH: 8
<212> TYPE: PRT
<213> ORGANISM: Artificial Sequence
<220> FEATURE:
<223> OTHER INFORMATION: targets AML

<400> SEQUENCE: 46
```

Cys Ala Tyr His Leu Arg Arg Cys
1               5

<210> SEQ ID NO 47
<211> LENGTH: 4
<212> TYPE: PRT
<213> ORGANISM: Artificial Sequence
<220> FEATURE:
<223> OTHER INFORMATION: Cell penetrating

<400> SEQUENCE: 47

Arg Leu Arg Arg
1

<210> SEQ ID NO 48
<211> LENGTH: 7
<212> TYPE: PRT
<213> ORGANISM: Artificial Sequence
<220> FEATURE:
<223> OTHER INFORMATION: Colonic dysplasia

<400> SEQUENCE: 48

Val Arg Pro Met Pro Leu Gln
1               5

<210> SEQ ID NO 49
<211> LENGTH: 7
<212> TYPE: PRT
<213> ORGANISM: Artificial Sequence
<220> FEATURE:
<223> OTHER INFORMATION: Radiation-Induced Expression of Tax-Interacting
      Protein 1 (TIP-1) in Tumor Vasculature, Binds irradiated tumors
      i.e., ones responding to therapy

<400> SEQUENCE: 49

His Val Gly Gly Ser Ser Val
1               5

<210> SEQ ID NO 50
<211> LENGTH: 7
<212> TYPE: PRT
<213> ORGANISM: Artificial Sequence
<220> FEATURE:
<223> OTHER INFORMATION: Binds murine prostate vasculature

<400> SEQUENCE: 50

Ser Met Ser Ile Ala Arg Leu
1               5

<210> SEQ ID NO 51
<211> LENGTH: 7
<212> TYPE: PRT
<213> ORGANISM: Artificial Sequence
<220> FEATURE:
<223> OTHER INFORMATION: Binds murine prostate vasculature

<400> SEQUENCE: 51

Val Ser Phe Leu Glu Tyr Arg
1               5

<210> SEQ ID NO 52
<211> LENGTH: 32
<212> TYPE: PRT
<213> ORGANISM: Artificial Sequence
<220> FEATURE:
<223> OTHER INFORMATION: Fragment 3 of the high mobility group (HMG)N2

-continued

<400> SEQUENCE: 52

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Lys Ala Pro Ala Lys Lys
            20                  25                  30

<210> SEQ ID NO 53
<211> LENGTH: 19
<212> TYPE: PRT
<213> ORGANISM: Artificial Sequence
<220> FEATURE:
<223> OTHER INFORMATION: VEGF binding peptide

<400> SEQUENCE: 53

Val Glu Pro Asn Cys Asp Ile His Val Met Trp Glu Trp Glu Cys Phe
1               5                   10                  15

Glu Arg Leu

<210> SEQ ID NO 54
<211> LENGTH: 12
<212> TYPE: PRT
<213> ORGANISM: Artificial Sequence
<220> FEATURE:
<223> OTHER INFORMATION: L-PEPTIDE Nasopharyngeal Phage derived - causes
      internalization of phage

<400> SEQUENCE: 54

Arg Leu Leu Asp Thr Asn Arg Pro Leu Leu Pro Tyr
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Alpha(v) beta (6) integrin

<400> SEQUENCE: 55

Arg Gly Asp Leu Ala Thr Leu Arg Gln Leu Ala Gln Glu Asp Gly Val
1               5                   10                  15

Val Gly Val Arg
            20

<210> SEQ ID NO 56
<211> LENGTH: 7
<212> TYPE: PRT
<213> ORGANISM: Artificial Sequence
<220> FEATURE:
<223> OTHER INFORMATION: Transferrin

<400> SEQUENCE: 56

His Ala Ile Tyr Pro Arg His
1               5

<210> SEQ ID NO 57
<211> LENGTH: 12
<212> TYPE: PRT
<213> ORGANISM: Artificial Sequence
<220> FEATURE:
<223> OTHER INFORMATION: Transferrin

<400> SEQUENCE: 57

Thr His Arg Pro Pro Met Trp Ser Pro Val Trp Pro
1               5                   10

<210> SEQ ID NO 58
<211> LENGTH: 13
<212> TYPE: PRT
<213> ORGANISM: Artificial Sequence
<220> FEATURE:
<223> OTHER INFORMATION: CDR1, CD-22 binding

<400> SEQUENCE: 58

Cys Lys Ala Ser Gln Ser Val Thr Asn Asp Val Ala Cys
1               5                   10

<210> SEQ ID NO 59
<211> LENGTH: 9
<212> TYPE: PRT
<213> ORGANISM: Artificial Sequence
<220> FEATURE:
<223> OTHER INFORMATION: CDR2, CD-22 binding

<400> SEQUENCE: 59

Cys Tyr Ala Ser Asn Arg Tyr Thr Cys
1               5

<210> SEQ ID NO 60
<211> LENGTH: 12
<212> TYPE: PRT
<213> ORGANISM: Artificial Sequence
<220> FEATURE:
<223> OTHER INFORMATION: CDR3, CD-22 binding

<400> SEQUENCE: 60

Cys Gln Gln Asp Tyr Arg Ser Pro Leu Thr Phe Cys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: CDR1, CD-22 binding

<400> SEQUENCE: 61

Cys Ser Asp Tyr Gly Val Asn Trp Val Cys
1               5                   10

<210> SEQ ID NO 62
<211> LENGTH: 21
<212> TYPE: PRT
<213> ORGANISM: Artificial Sequence
<220> FEATURE:
<223> OTHER INFORMATION: CDR2, CD-22 binding

<400> SEQUENCE: 62

Cys Leu Gly Ile Ile Trp Gly Asp Gly Arg Thr Asp Tyr Asn Ser Ala
1               5                   10                  15

Leu Lys Ser Arg Cys
            20

<210> SEQ ID NO 63
<211> LENGTH: 7
<212> TYPE: PRT
<213> ORGANISM: Artificial Sequence
<220> FEATURE:
<223> OTHER INFORMATION: Breast cancer targeting
<220> FEATURE:
<221> NAME/KEY: misc_feature
<222> LOCATION: (4)..(4)
<223> OTHER INFORMATION: Xaa can be any naturally occurring amino acid

<400> SEQUENCE: 63

Leu Thr Val Xaa Pro Trp Tyr
1               5

<210> SEQ ID NO 64
<211> LENGTH: 9
<212> TYPE: PRT
<213> ORGANISM: Artificial Sequence
<220> FEATURE:
<223> OTHER INFORMATION: AML targeting

<400> SEQUENCE: 64

Cys Pro Leu Asp Ile Asp Phe Tyr Cys
1               5

<210> SEQ ID NO 65
<211> LENGTH: 16
<212> TYPE: PRT
<213> ORGANISM: Artificial Sequence
<220> FEATURE:
<223> OTHER INFORMATION: Hematological malignancy targeting

<400> SEQUENCE: 65

Ala Asp Gly Ala Cys Leu Arg Ser Gly Arg Gly Cys Gly Ala Ala Lys
1               5                   10                  15

<210> SEQ ID NO 66
<211> LENGTH: 13
<212> TYPE: PRT
<213> ORGANISM: Artificial Sequence
<220> FEATURE:
<223> OTHER INFORMATION: Lymphoma targeting

<400> SEQUENCE: 66

Gly Phe Leu Gly Glu Asp Pro Gly Phe Phe Asn Val Glu
1               5                   10

<210> SEQ ID NO 67
<211> LENGTH: 32
<212> TYPE: PRT
<213> ORGANISM: Artificial Sequence
<220> FEATURE:
<223> OTHER INFORMATION: Cysteine modified F3-peptide sequence, targets
      tumor neovasculature

<400> SEQUENCE: 67

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Lys Ala Pro Ala Lys Lys
                20                  25                  30

<210> SEQ ID NO 68
<211> LENGTH: 15
<212> TYPE: PRT
<213> ORGANISM: Artificial Sequence
<220> FEATURE:
<223> OTHER INFORMATION: P15 peptide, Type II receptor targeting

<400> SEQUENCE: 68

Gly Thr Pro Gly Pro Gln Gly Ile Ala Gly Gln Arg Gly Val Val
1               5                   10                  15

<210> SEQ ID NO 69
<211> LENGTH: 7
<212> TYPE: PRT

<213> ORGANISM: Artificial Sequence
<220> FEATURE:
<223> OTHER INFORMATION: Septa-peptide with TGF-like activity
      (Cytomodulin)

<400> SEQUENCE: 69

Ala Asn Val Ala Glu Asn Ala
1               5

<210> SEQ ID NO 70
<211> LENGTH: 12
<212> TYPE: PRT
<213> ORGANISM: Artificial Sequence
<220> FEATURE:
<223> OTHER INFORMATION: Peptide from Clostridium

<400> SEQUENCE: 70

Cys Gln Thr Ile Asp Gly Lys Lys Tyr Tyr Phe Asn
1               5                   10

<210> SEQ ID NO 71
<211> LENGTH: 12
<212> TYPE: PRT
<213> ORGANISM: Artificial Sequence
<220> FEATURE:
<223> OTHER INFORMATION: targets surface idiotype of SUP-88 human B-cell
      lymphoma
<220> FEATURE:
<221> NAME/KEY: MISC_FEATURE
<222> LOCATION: (12)..(12)
<223> OTHER INFORMATION: X is pyrrolysine

<400> SEQUENCE: 71

Lys Asn Gly Pro Trp Tyr Ala Tyr Thr Gly Arg Xaa
1               5                   10

<210> SEQ ID NO 72
<211> LENGTH: 8
<212> TYPE: PRT
<213> ORGANISM: Artificial Sequence
<220> FEATURE:
<223> OTHER INFORMATION: targets surface idiotype of SUP-88 human B-cell
      lymphoma
<220> FEATURE:
<221> NAME/KEY: misc_feature
<222> LOCATION: (6)..(6)
<223> OTHER INFORMATION: Xaa can be any naturally occurring amino acid

<400> SEQUENCE: 72

Asn Trp Ala Val Trp Xaa Lys Arg
1               5

<210> SEQ ID NO 73
<211> LENGTH: 9
<212> TYPE: PRT
<213> ORGANISM: Artificial Sequence
<220> FEATURE:
<223> OTHER INFORMATION: Targets surface idiotype of SUP-88 human B-cell
      lymphoma
<220> FEATURE:
<221> NAME/KEY: misc_feature
<222> LOCATION: (2)..(3)
<223> OTHER INFORMATION: Xaa can be any naturally occurring amino acid

<400> SEQUENCE: 73

Tyr Xaa Xaa Glu Asp Leu Arg Arg Arg
1               5

<210> SEQ ID NO 74

```
<211> LENGTH: 8
<212> TYPE: PRT
<213> ORGANISM: Artificial Sequence
<220> FEATURE:
<223> OTHER INFORMATION: Targets surface idiotype of SUP-88 human B-cell
      lymphoma
<220> FEATURE:
<221> NAME/KEY: misc_feature
<222> LOCATION: (1)..(2)
<223> OTHER INFORMATION: Xaa can be any naturally occurring amino acid

<400> SEQUENCE: 74

Xaa Xaa Pro Val Asp His Gly Leu
1               5

<210> SEQ ID NO 75
<211> LENGTH: 81
<212> TYPE: PRT
<213> ORGANISM: Artificial Sequence
<220> FEATURE:
<223> OTHER INFORMATION: Targets surface idiotype of human chronic
      lymphocytic lymphoma (CLL)

<400> SEQUENCE: 75

Leu Val Arg Ser Thr Gly Gln Phe Val Leu Val Ser Pro Ser Gly Ser
1               5                   10                  15

Trp Thr Ala Leu Arg Pro Ser Gly Glu Trp Leu Ala Ile Met Ala Ser
            20                  25                  30

Gly Gln Trp Leu Gln Ile Leu Ala Ser Gly Arg Trp Leu Arg Arg Pro
        35                  40                  45

Ser His Ala Met Ala Arg Asp Asn Asn Arg Pro Ala Asn Ser Met Leu
    50                  55                  60

Gln Asp Arg Leu Arg Phe Ala Thr Pro Leu Ser Gly Asp Lys Ser Ser
65                  70                  75                  80

Thr

<210> SEQ ID NO 76
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 76

Phe Asp Asp Ala Arg Leu
1               5

<210> SEQ ID NO 77
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 77

Phe Ser Asp Ala Arg Leu
1               5

<210> SEQ ID NO 78
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 78
```

```
Phe Ser Asp Met Arg Leu
1               5

<210> SEQ ID NO 79
<211> LENGTH: 6
<212> TYPE: PRT
<213> ORGANISM: Artificial Sequence
<220> FEATURE:
<223> OTHER INFORMATION: targets human multiple myeloma M protein

<400> SEQUENCE: 79

Phe Val Asp Val Arg Leu
1               5

<210> SEQ ID NO 80
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 80

Phe Thr Asp Ile Arg Leu
1               5

<210> SEQ ID NO 81
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 81

Phe Asn Asp Tyr Arg Leu
1               5

<210> SEQ ID NO 82
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 82

Phe Ser Asp Thr Arg Leu
1               5

<210> SEQ ID NO 83
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 83

Pro Ile His Tyr Ile Phe
1               5

<210> SEQ ID NO 84
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 84
```

Tyr Ile His Tyr Ile Phe
1               5

<210> SEQ ID NO 85
<211> LENGTH: 6
<212> TYPE: PRT
<213> ORGANISM: Artificial Sequence
<220> FEATURE:
<223> OTHER INFORMATION: Targets human multiple myeloma M protein

<400> SEQUENCE: 85

Arg Ile His Tyr Ile Phe
1               5

<210> SEQ ID NO 86
<211> LENGTH: 7
<212> TYPE: PRT
<213> ORGANISM: Artificial Sequence
<220> FEATURE:
<223> OTHER INFORMATION: Targets HL 60 human lymphoma & B-16 mouse
      melanoma

<400> SEQUENCE: 86

Ile Glu Leu Leu Gln Ala Arg
1               5

<210> SEQ ID NO 87
<211> LENGTH: 10
<212> TYPE: PRT
<213> ORGANISM: Artificial Sequence
<220> FEATURE:
<223> OTHER INFORMATION: Prostate-specific antigen (PSA) targeting
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 87

Cys Val Phe Xaa Xaa Xaa Tyr Xaa Xaa Cys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Prostate-specific antigen (PSA) targeting
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 88

Cys Xaa Phe Xaa Xaa Xaa Tyr Xaa Tyr Leu Met Cys
1               5                   10

<210> SEQ ID NO 89
<211> LENGTH: 13

```
<212> TYPE: PRT
<213> ORGANISM: Artificial Sequence
<220> FEATURE:
<223> OTHER INFORMATION: Prostate-specific antigen (PSA) targeting
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 89

Cys Val Xaa Tyr Cys Xaa Xaa Xaa Xaa Cys Tyr Val Cys
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Prostate-specific antigen (PSA) targeting
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 90

Cys Val Xaa Tyr Cys Xaa Xaa Xaa Xaa Cys Trp Xaa Cys
1               5                   10

<210> SEQ ID NO 91
<211> LENGTH: 8
<212> TYPE: PRT
<213> ORGANISM: Artificial Sequence
<220> FEATURE:
<223> OTHER INFORMATION: LNCaP prostate cancer targeting

<400> SEQUENCE: 91

Asp Pro Arg Ala Thr Pro Gly Ser
1               5

<210> SEQ ID NO 92
<211> LENGTH: 12
<212> TYPE: PRT
<213> ORGANISM: Artificial Sequence
<220> FEATURE:
<223> OTHER INFORMATION: WAC-2 human neuroblastoma targeting

<400> SEQUENCE: 92

His Leu Gln Leu Gln Pro Trp Tyr Pro Gln Ile Ser
1               5                   10

<210> SEQ ID NO 93
<211> LENGTH: 12
<212> TYPE: PRT
<213> ORGANISM: Artificial Sequence
<220> FEATURE:
<223> OTHER INFORMATION: MDA-MB435 breast cancer targeting

<400> SEQUENCE: 93
```

```
Val Pro Trp Met Glu Pro Ala Tyr Gln Arg Phe Leu
1               5                   10
```

<210> SEQ ID NO 94
<211> LENGTH: 12
<212> TYPE: PRT
<213> ORGANISM: Artificial Sequence
<220> FEATURE:
<223> OTHER INFORMATION: Head and neck cancer lines targeting

<400> SEQUENCE: 94

```
Thr Ser Pro Leu Asn Ile His Asn Gly Gln Lys Leu
1               5                   10
```

<210> SEQ ID NO 95
<211> LENGTH: 9
<212> TYPE: PRT
<213> ORGANISM: Artificial Sequence
<220> FEATURE:
<223> OTHER INFORMATION: HEp-2 human larygeal carcinoma targeting

<400> SEQUENCE: 95

```
Arg Leu Thr Gly Gly Lys Gly Val Gly
1               5
```

<210> SEQ ID NO 96
<211> LENGTH: 9
<212> TYPE: PRT
<213> ORGANISM: Artificial Sequence
<220> FEATURE:
<223> OTHER INFORMATION: RGD-4C, Tumor vasculature targeting

<400> SEQUENCE: 96

```
Cys Asp Cys Arg Gly Asp Cys Phe Cys
1               5
```

<210> SEQ ID NO 97
<211> LENGTH: 11
<212> TYPE: PRT
<213> ORGANISM: Artificial Sequence
<220> FEATURE:
<223> OTHER INFORMATION: Tumor vasculature targeting

<400> SEQUENCE: 97

```
Ala Cys Asp Cys Arg Gly Asp Cys Phe Cys Gly
1               5                   10
```

<210> SEQ ID NO 98
<211> LENGTH: 13
<212> TYPE: PRT
<213> ORGANISM: Artificial Sequence
<220> FEATURE:
<223> OTHER INFORMATION: Aminopeptidase N targeting

<400> SEQUENCE: 98

```
Cys Asn Gly Arg Cys Val Ser Gly Cys Ala Gly Arg Cys
1               5                   10
```

<210> SEQ ID NO 99
<211> LENGTH: 9
<212> TYPE: PRT
<213> ORGANISM: Artificial Sequence
<220> FEATURE:
<223> OTHER INFORMATION: Tumor vasculature targeting

<400> SEQUENCE: 99

```
Cys Val Cys Asn Gly Arg Met Glu Cys
```

```
1               5
```

<210> SEQ ID NO 100
<211> LENGTH: 6
<212> TYPE: PRT
<213> ORGANISM: Artificial Sequence
<220> FEATURE:
<223> OTHER INFORMATION: Tumor vasculature targeting

<400> SEQUENCE: 100

```
Asn Gly Arg Ala His Ala
1               5
```

<210> SEQ ID NO 101
<211> LENGTH: 10
<212> TYPE: PRT
<213> ORGANISM: Artificial Sequence
<220> FEATURE:
<223> OTHER INFORMATION: Tumor vasculature targeting

<400> SEQUENCE: 101

```
Thr Ala Ala Ser Gly Val Arg Ser Met His
1               5                   10
```

<210> SEQ ID NO 102
<211> LENGTH: 10
<212> TYPE: PRT
<213> ORGANISM: Artificial Sequence
<220> FEATURE:
<223> OTHER INFORMATION: Tumor vasculature targeting

<400> SEQUENCE: 102

```
Leu Thr Leu Arg Trp Val Gly Leu Met Ser
1               5                   10
```

<210> SEQ ID NO 103
<211> LENGTH: 15
<212> TYPE: PRT
<213> ORGANISM: Artificial Sequence
<220> FEATURE:
<223> OTHER INFORMATION: IC-12 rat trachea targeting

<400> SEQUENCE: 103

```
Leu Arg Ile Lys Arg Lys Arg Lys Arg Lys Lys Thr Arg Lys
1               5                   10                  15
```

<210> SEQ ID NO 104
<211> LENGTH: 6
<212> TYPE: PRT
<213> ORGANISM: Artificial Sequence
<220> FEATURE:
<223> OTHER INFORMATION: IC-12 rat trachea targeting

<400> SEQUENCE: 104

```
Asn Arg Ser Thr His Ile
1               5
```

<210> SEQ ID NO 105
<211> LENGTH: 7
<212> TYPE: PRT
<213> ORGANISM: Artificial Sequence
<220> FEATURE:
<223> OTHER INFORMATION: Mouse prostate targeting

<400> SEQUENCE: 105

```
Ser Met Ser Ile Ala Arg Leu
1               5
```

<210> SEQ ID NO 106
<211> LENGTH: 7
<212> TYPE: PRT
<213> ORGANISM: Artificial Sequence
<220> FEATURE:
<223> OTHER INFORMATION: Mouse prostate targeting

<400> SEQUENCE: 106

Val Ser Phe Leu Glu Tyr Arg
1               5

<210> SEQ ID NO 107
<211> LENGTH: 9
<212> TYPE: PRT
<213> ORGANISM: Artificial Sequence
<220> FEATURE:
<223> OTHER INFORMATION: Aminopeptidase P targeting

<400> SEQUENCE: 107

Cys Pro Gly Pro Glu Gly Ala Gly Cys
1               5

<210> SEQ ID NO 108
<211> LENGTH: 7
<212> TYPE: PRT
<213> ORGANISM: Artificial Sequence
<220> FEATURE:
<223> OTHER INFORMATION: VEGF targeting

<400> SEQUENCE: 108

Ala Thr Trp Leu Pro Pro Arg
1               5

<210> SEQ ID NO 109
<211> LENGTH: 6
<212> TYPE: PRT
<213> ORGANISM: Artificial Sequence
<220> FEATURE:
<223> OTHER INFORMATION: VEGF targeting

<400> SEQUENCE: 109

Arg Arg Lys Arg Arg Arg
1               5

<210> SEQ ID NO 110
<211> LENGTH: 10
<212> TYPE: PRT
<213> ORGANISM: Artificial Sequence
<220> FEATURE:
<223> OTHER INFORMATION: Gelatinase targeting

<400> SEQUENCE: 110

Cys Thr Thr His Trp Gly Phe Thr Leu Cys
1               5                   10

<210> SEQ ID NO 111
<211> LENGTH: 4
<212> TYPE: PRT
<213> ORGANISM: Artificial Sequence
<220> FEATURE:
<223> OTHER INFORMATION: Targets idiotype of WEHI-231 murine lymphoma
      cell line

<400> SEQUENCE: 111

Trp Tyr Asp Asp
1

```
<210> SEQ ID NO 112
<211> LENGTH: 4
<212> TYPE: PRT
<213> ORGANISM: Artificial Sequence
<220> FEATURE:
<223> OTHER INFORMATION: targets idiotype of WEHI-279 murine lymphoma
      cell line

<400> SEQUENCE: 112

Arg Trp Ile Asp
1

<210> SEQ ID NO 113
<211> LENGTH: 4
<212> TYPE: PRT
<213> ORGANISM: Artificial Sequence
<220> FEATURE:
<223> OTHER INFORMATION: targets idiotype of WEHI-279 murine lymphoma
      cell line

<400> SEQUENCE: 113

Arg Trp Phe Asp
1

<210> SEQ ID NO 114
<211> LENGTH: 12
<212> TYPE: PRT
<213> ORGANISM: Artificial Sequence
<220> FEATURE:
<223> OTHER INFORMATION: Targets alpha-6-beta 1 integrin of DU145
      prostate cancer cell line
<220> FEATURE:
<221> NAME/KEY: misc_feature
<222> LOCATION: (12)..(12)
<223> OTHER INFORMATION: Xaa can be any naturally occurring amino acid

<400> SEQUENCE: 114

Leu Asn Asn Ile Val Ser Val Asn Gly Arg His Xaa
1               5                   10

<210> SEQ ID NO 115
<211> LENGTH: 11
<212> TYPE: PRT
<213> ORGANISM: Artificial Sequence
<220> FEATURE:
<223> OTHER INFORMATION: targets alpha-6-beta 1 integrin of DU145
      prostate cancer cell line
<220> FEATURE:
<221> NAME/KEY: misc_feature
<222> LOCATION: (10)..(11)
<223> OTHER INFORMATION: Xaa can be any naturally occurring amino acid

<400> SEQUENCE: 115

Asp Asn Arg Ile Arg Leu Gln Ala Lys Xaa Xaa
1               5                   10

<210> SEQ ID NO 116
<211> LENGTH: 26
<212> TYPE: PRT
<213> ORGANISM: Artificial Sequence
<220> FEATURE:
<223> OTHER INFORMATION: Processed (short) active delta lysin S. aureus

<400> SEQUENCE: 116

Met Ala Gln Asp Ile Ile Ser Thr Ile Ser Asp Leu Val Lys Trp Ile
1               5                   10                  15

Ile Asp Thr Val Asn Lys Phe Thr Lys Lys
```

```
                        20                  25

<210> SEQ ID NO 117
<211> LENGTH: 26
<212> TYPE: PRT
<213> ORGANISM: Artificial Sequence
<220> FEATURE:
<223> OTHER INFORMATION: Delta lysin processed S. epidermitidis

<400> SEQUENCE: 117

Met Met Ala Ala Asp Ile Ile Ser Thr Ile Gly Asp Leu Val Lys Trp
1               5                   10                  15

Ile Ile Asp Thr Val Asn Lys Phe Lys Lys
                20                  25

<210> SEQ ID NO 118
<211> LENGTH: 26
<212> TYPE: PRT
<213> ORGANISM: Artificial Sequence
<220> FEATURE:
<223> OTHER INFORMATION: Delta lysin from CA-MRSA

<400> SEQUENCE: 118

Met Ala Gln Asp Ile Ile Ser Thr Ile Ser Asp Leu Val Lys Trp Ile
1               5                   10                  15

Ile Asp Thr Val Asn Lys Phe Thr Lys Lys
                20                  25

<210> SEQ ID NO 119
<211> LENGTH: 21
<212> TYPE: PRT
<213> ORGANISM: Artificial Sequence
<220> FEATURE:
<223> OTHER INFORMATION: PSM-alpha-1

<400> SEQUENCE: 119

Met Gly Ile Ile Ala Gly Ile Ile Lys Val Ile Lys Ser Leu Ile Glu
1               5                   10                  15

Gln Phe Thr Gly Lys
                20

<210> SEQ ID NO 120
<211> LENGTH: 21
<212> TYPE: PRT
<213> ORGANISM: Artificial Sequence
<220> FEATURE:
<223> OTHER INFORMATION: PSM-alpha-2

<400> SEQUENCE: 120

Met Gly Ile Ile Ala Gly Ile Ile Lys Phe Ile Lys Gly Leu Ile Glu
1               5                   10                  15

Lys Phe Thr Gly Lys
                20

<210> SEQ ID NO 121
<211> LENGTH: 22
<212> TYPE: PRT
<213> ORGANISM: Artificial Sequence
<220> FEATURE:
<223> OTHER INFORMATION: PSM-alpha-3

<400> SEQUENCE: 121

Met Glu Phe Val Ala Lys Leu Phe Lys Phe Phe Lys Asp Leu Leu Gly
1               5                   10                  15
```

Lys Phe Leu Gly Asn Asn
            20

<210> SEQ ID NO 122
<211> LENGTH: 20
<212> TYPE: PRT
<213> ORGANISM: Artificial Sequence
<220> FEATURE:
<223> OTHER INFORMATION: PSM-alpha-4

<400> SEQUENCE: 122

Met Ala Ile Val Gly Thr Ile Ile Lys Ile Ile Lys Ala Ile Ile Asp
1               5                   10                  15

Ile Phe Ala Lys
            20

<210> SEQ ID NO 123
<211> LENGTH: 44
<212> TYPE: PRT
<213> ORGANISM: Artificial Sequence
<220> FEATURE:
<223> OTHER INFORMATION: PSM-beta-1

<400> SEQUENCE: 123

Met Glu Gly Leu Phe Asn Ala Ile Lys Asp Thr Val Thr Ala Ala Ile
1               5                   10                  15

Asn Asn Asp Gly Ala Lys Leu Gly Thr Ser Ile Val Ser Ile Val Glu
            20                  25                  30

Asn Gly Val Gly Leu Leu Gly Lys Leu Phe Gly Phe
        35                  40

<210> SEQ ID NO 124
<211> LENGTH: 44
<212> TYPE: PRT
<213> ORGANISM: Artificial Sequence
<220> FEATURE:
<223> OTHER INFORMATION: PSM-beta-2

<400> SEQUENCE: 124

Met Thr Gly Leu Ala Glu Ala Ile Ala Asn Thr Val Gln Ala Ala Gln
1               5                   10                  15

Gln His Asp Ser Val Lys Leu Gly Thr Ser Ile Val Asp Ile Val Ala
            20                  25                  30

Asn Gly Val Gly Leu Leu Gly Lys Leu Phe Gly Phe
        35                  40

<210> SEQ ID NO 125
<211> LENGTH: 85
<212> TYPE: PRT
<213> ORGANISM: Escherichia coli

<400> SEQUENCE: 125

Met Gly Leu Lys Leu Asp Leu Thr Trp Phe Asp Lys Ser Thr Glu Asp
1               5                   10                  15

Phe Lys Gly Glu Glu Tyr Ser Lys Asp Phe Gly Asp Asp Gly Ser Val
            20                  25                  30

Met Glu Ser Leu Gly Val Pro Phe Lys Asp Asn Val Asn Asn Gly Cys
        35                  40                  45

Phe Asp Val Ile Ala Glu Trp Val Pro Leu Gln Pro Tyr Phe Asn
    50                  55                  60

His Gln Ile Asp Ile Ser Asp Asn Glu Tyr Phe Val Ser Phe Asp Tyr
65                  70                  75                  80

-continued

```
Arg Asp Gly Asp Trp
                85

<210> SEQ ID NO 126
<211> LENGTH: 601
<212> TYPE: PRT
<213> ORGANISM: Artificial Sequence
<220> FEATURE:
<223> OTHER INFORMATION: Chimera targeted to cancer, consisting of M13
      pIII protein 18-AA signal sequence, natural ala and a 3 gly
      spacer, mature 50-AA peptide for TGF-alpha, pIII truncated after
      AA 372, C-term Col E3, stop

<400> SEQUENCE: 126

Met Lys Lys Leu Leu Phe Ala Ile Pro Leu Val Val Pro Phe Tyr Ser
1               5                   10                  15

His Ser Ala Gly Gly Gly Val Val Ser His Phe Asn Asp Cys Pro Asp
            20                  25                  30

Ser His Thr Gln Phe Cys Phe His Gly Thr Cys Arg Phe Leu Val Gln
        35                  40                  45

Glu Asp Lys Pro Ala Cys Val Cys His Ser Gly Tyr Val Gly Ala Arg
50                  55                  60

Cys Glu His Ala Asp Leu Leu Ala Ala Glu Thr Val Glu Ser Cys Leu
65                  70                  75                  80

Ala Lys Ser His Thr Glu Asn Ser Phe Thr Asn Val Trp Lys Asp Asp
                85                  90                  95

Lys Thr Leu Asp Arg Tyr Ala Asn Tyr Glu Gly Cys Leu Trp Asn Ala
            100                 105                 110

Thr Gly Val Val Val Cys Thr Gly Asp Glu Thr Gln Cys Tyr Gly Thr
        115                 120                 125

Trp Val Pro Ile Gly Leu Ala Ile Pro Glu Asn Glu Gly Gly Gly Ser
130                 135                 140

Glu Gly Gly Gly Ser Glu Gly Gly Ser Glu Gly Gly Thr Lys
145                 150                 155                 160

Pro Pro Glu Tyr Gly Asp Thr Pro Ile Pro Gly Tyr Thr Tyr Ile Asn
                165                 170                 175

Pro Leu Asp Gly Thr Tyr Pro Pro Gly Thr Glu Gln Asn Pro Ala Asn
            180                 185                 190

Pro Asn Pro Ser Leu Glu Glu Ser Gln Pro Leu Asn Thr Phe Met Phe
        195                 200                 205

Gln Asn Asn Arg Phe Arg Asn Arg Gln Gly Ala Leu Thr Val Tyr Thr
210                 215                 220

Gly Thr Val Thr Gln Gly Thr Asp Pro Val Lys Thr Tyr Tyr Gln Tyr
225                 230                 235                 240

Thr Pro Val Ser Ser Lys Ala Met Tyr Asp Ala Tyr Trp Asn Gly Lys
                245                 250                 255

Phe Arg Asp Cys Ala Phe His Ser Gly Phe Asn Glu Asp Leu Phe Val
            260                 265                 270

Cys Glu Tyr Gln Gly Gln Ser Ser Asp Leu Pro Gln Pro Pro Val Asn
        275                 280                 285

Ala Gly Gly Gly Ser Gly Gly Ser Gly Gly Ser Glu Gly Gly
290                 295                 300

Gly Ser Glu Gly Gly Ser Glu Gly Gly Ser Glu Gly Gly
305                 310                 315                 320

Ser Gly Gly Ser Gly Ser Gly Asp Phe Asp Tyr Glu Lys Met Ala
                325                 330                 335
```

-continued

```
Asn Ala Asn Lys Gly Ala Met Thr Glu Asn Ala Asp Glu Asn Ala Leu
            340                 345                 350

Gln Ser Asp Ala Lys Gly Lys Leu Asp Ser Val Ala Thr Asp Tyr Gly
        355                 360                 365

Ala Ala Ile Asp Gly Phe Ile Gly Asp Val Ser Gly Leu Ala Asn Gly
370                 375                 380

Asn Gly Ala Thr Gly Asp Phe Ala Gly Ser Asn Ser Gln Met Ala Gln
385                 390                 395                 400

Val Gly Asp Gly Asp Asn Ser Pro Leu Met Asn Asn Phe Arg Gln Tyr
                405                 410                 415

Leu Pro Ser Leu Pro Gln Ser Val Glu Cys Arg Phe Ala His Asp Pro
            420                 425                 430

Met Ala Gly Gly His Arg Met Trp Gln Met Ala Gly Leu Lys Ala Gln
        435                 440                 445

Arg Ala Gln Thr Asp Val Asn Asn Lys Gln Ala Ala Phe Asp Ala Ala
    450                 455                 460

Ala Lys Glu Lys Ser Asp Ala Asp Ala Ala Leu Ser Ser Ala Met Glu
465                 470                 475                 480

Ser Arg Lys Lys Lys Glu Asp Lys Lys Arg Ser Ala Glu Asn Asn Leu
                485                 490                 495

Asn Asp Glu Lys Asn Lys Pro Arg Lys Gly Phe Lys Asp Tyr Gly His
            500                 505                 510

Asp Tyr His Pro Ala Pro Lys Thr Glu Asn Ile Lys Gly Leu Gly Asp
        515                 520                 525

Leu Lys Pro Gly Ile Pro Lys Thr Pro Lys Gln Asn Gly Gly Gly Lys
    530                 535                 540

Arg Lys Arg Trp Thr Gly Asp Lys Gly Arg Lys Ile Tyr Glu Trp Asp
545                 550                 555                 560

Ser Gln His Gly Glu Leu Glu Gly Tyr Arg Ala Ser Asp Gly Gln His
                565                 570                 575

Leu Gly Ser Phe Asp Pro Lys Thr Gly Asn Gln Leu Lys Gly Pro Asp
            580                 585                 590

Pro Lys Arg Asn Ile Lys Lys Tyr Leu
        595                 600

<210> SEQ ID NO 127
<211> LENGTH: 620
<212> TYPE: PRT
<213> ORGANISM: Artificial Sequence
<220> FEATURE:
<223> OTHER INFORMATION: Lytic peptide PSM-alpha-3 is inserted between
      the pIII signal sequence and the TGF-alpha (Figure 3B)

<400> SEQUENCE: 127

Met Lys Lys Leu Leu Phe Ala Ile Pro Leu Val Val Pro Phe Tyr Ser
1               5                   10                  15

His Ser Ala Met Glu Phe Val Ala Lys Leu Phe Lys Phe Phe Lys Asp
            20                  25                  30

Leu Leu Gly Lys Phe Leu Gly Asn Asn Val Val Ser His Phe Asn Asp
        35                  40                  45

Cys Pro Asp Ser His Thr Gln Phe Cys Phe His Gly Thr Cys Arg Phe
    50                  55                  60

Leu Val Gln Glu Asp Lys Pro Ala Cys Val Cys His Ser Gly Tyr Val
65                  70                  75                  80

Gly Ala Arg Cys Glu His Ala Asp Leu Leu Ala Ala Glu Thr Val Glu
```

```
            85                  90                  95
Ser Cys Leu Ala Lys Ser His Thr Glu Asn Ser Phe Thr Asn Val Trp
            100                 105                 110

Lys Asp Lys Thr Leu Asp Arg Tyr Ala Asn Tyr Glu Gly Cys Leu
            115                 120                 125

Trp Asn Ala Thr Gly Val Val Val Cys Thr Gly Asp Glu Thr Gln Cys
130                 135                 140

Tyr Gly Thr Trp Val Pro Ile Gly Leu Ala Ile Pro Glu Asn Glu Gly
145                 150                 155                 160

Gly Gly Ser Glu Gly Gly Ser Gly Gly Ser Glu Gly Gly
            165                 170                 175

Gly Thr Lys Pro Pro Glu Tyr Gly Asp Thr Pro Ile Pro Gly Tyr Thr
            180                 185                 190

Tyr Ile Asn Pro Leu Asp Gly Thr Tyr Pro Pro Gly Thr Glu Gln Asn
            195                 200                 205

Pro Ala Asn Pro Asn Pro Ser Leu Glu Glu Ser Gln Pro Leu Asn Thr
210                 215                 220

Phe Met Phe Gln Asn Asn Arg Phe Arg Asn Arg Gln Gly Ala Leu Thr
225                 230                 235                 240

Val Tyr Thr Gly Thr Val Thr Gln Gly Thr Asp Pro Val Lys Thr Tyr
            245                 250                 255

Tyr Gln Tyr Thr Pro Val Ser Ser Lys Ala Met Tyr Asp Ala Tyr Trp
            260                 265                 270

Asn Gly Lys Phe Arg Asp Cys Ala Phe His Ser Gly Phe Asn Glu Asp
            275                 280                 285

Leu Phe Val Cys Glu Tyr Gln Gly Gln Ser Ser Asp Leu Pro Gln Pro
            290                 295                 300

Pro Val Asn Ala Gly Gly Gly Ser Gly Gly Ser Gly Gly Gly Ser
305                 310                 315                 320

Glu Gly Gly Gly Ser Glu Gly Gly Ser Glu Gly Gly Ser Glu
            325                 330                 335

Gly Gly Gly Ser Gly Gly Ser Gly Ser Gly Asp Phe Asp Tyr Glu
            340                 345                 350

Lys Met Ala Asn Ala Asn Lys Gly Ala Met Thr Glu Asn Ala Asp Glu
            355                 360                 365

Asn Ala Leu Gln Ser Asp Ala Lys Gly Lys Leu Asp Ser Val Ala Thr
            370                 375                 380

Asp Tyr Gly Ala Ala Ile Asp Gly Phe Ile Gly Asp Val Ser Gly Leu
385                 390                 395                 400

Ala Asn Gly Asn Gly Ala Thr Gly Asp Phe Ala Gly Ser Asn Ser Gln
            405                 410                 415

Met Ala Gln Val Gly Asp Gly Asp Asn Ser Pro Leu Met Asn Asn Phe
            420                 425                 430

Arg Gln Tyr Leu Pro Ser Leu Pro Gln Ser Val Glu Cys Arg Phe Ala
            435                 440                 445

His Asp Pro Met Ala Gly Gly His Arg Met Trp Gln Met Ala Gly Leu
            450                 455                 460

Lys Ala Gln Arg Ala Gln Thr Asp Val Asn Asn Lys Gln Ala Ala Phe
465                 470                 475                 480

Asp Ala Ala Ala Lys Glu Lys Ser Asp Ala Asp Ala Ala Leu Ser Ser
            485                 490                 495

Ala Met Glu Ser Arg Lys Lys Lys Glu Asp Lys Lys Arg Ser Ala Glu
            500                 505                 510
```

```
Asn Asn Leu Asn Asp Glu Lys Asn Lys Pro Arg Lys Gly Phe Lys Asp
        515                 520                 525

Tyr Gly His Asp Tyr His Pro Ala Pro Lys Thr Glu Asn Ile Lys Gly
    530                 535                 540

Leu Gly Asp Leu Lys Pro Gly Ile Pro Lys Thr Pro Lys Gln Asn Gly
545                 550                 555                 560

Gly Gly Lys Arg Lys Arg Trp Thr Gly Asp Lys Gly Arg Lys Ile Tyr
                565                 570                 575

Glu Trp Asp Ser Gln His Gly Glu Leu Glu Gly Tyr Arg Ala Ser Asp
                580                 585                 590

Gly Gln His Leu Gly Ser Phe Asp Pro Lys Thr Gly Asn Gln Leu Lys
        595                 600                 605

Gly Pro Asp Pro Lys Arg Asn Ile Lys Lys Tyr Leu
    610                 615                 620

<210> SEQ ID NO 128
<211> LENGTH: 5
<212> TYPE: PRT
<213> ORGANISM: Artificial Sequence
<220> FEATURE:
<223> OTHER INFORMATION: RGD-containing peptides (RGD4C)

<400> SEQUENCE: 128

Gly Arg Asp Gly Ser
1               5

<210> SEQ ID NO 129
<211> LENGTH: 5
<212> TYPE: PRT
<213> ORGANISM: Artificial Sequence
<220> FEATURE:
<223> OTHER INFORMATION: tol box penta peptide

<400> SEQUENCE: 129

Asp Gly Ser Gly Trp
1               5

<210> SEQ ID NO 130
<211> LENGTH: 21
<212> TYPE: PRT
<213> ORGANISM: Artificial Sequence
<220> FEATURE:
<223> OTHER INFORMATION: Extended tolB box

<400> SEQUENCE: 130

Asp Gly Ser Gly Trp Ser Ser Glu Asn Asn Pro Trp Gly Gly Gly Ser
1               5                   10                  15

Gly Ser Ile His Trp
            20

<210> SEQ ID NO 131
<211> LENGTH: 18
<212> TYPE: PRT
<213> ORGANISM: Artificial Sequence
<220> FEATURE:
<223> OTHER INFORMATION: N-terminal signal sequence from M13pIII

<400> SEQUENCE: 131

Met Lys Lys Leu Leu Phe Ala Ile Pro Leu Val Val Pro Phe Tyr Ser
1               5                   10                  15

His Ser
```

-continued

<210> SEQ ID NO 132
<211> LENGTH: 60
<212> TYPE: PRT
<213> ORGANISM: Artificial Sequence
<220> FEATURE:
<223> OTHER INFORMATION: C-terminal signal sequence of hlyA

<400> SEQUENCE: 132

```
Ser Thr Tyr Gly Ser Gln Asp Tyr Leu Asn Pro Leu Ile Asn Glu Ile
1               5                   10                  15

Ser Lys Ile Ile Ser Ala Ala Gly Asn Leu Asp Val Lys Glu Glu Arg
            20                  25                  30

Ser Ala Ala Ser Leu Leu Gln Leu Ser Gly Asn Ala Ser Asp Phe Ser
        35                  40                  45

Tyr Gly Arg Asn Ser Ile Thr Leu Thr Ala Ser Ala
    50                  55                  60
```

<210> SEQ ID NO 133
<211> LENGTH: 6
<212> TYPE: PRT
<213> ORGANISM: Artificial Sequence
<220> FEATURE:
<223> OTHER INFORMATION: Furin cleavage signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 133

```
Arg Xaa Lys Arg Ser Xaa
1               5
```

<210> SEQ ID NO 134
<211> LENGTH: 60
<212> TYPE: PRT
<213> ORGANISM: Artificial Sequence
<220> FEATURE:
<223> OTHER INFORMATION: C-terminal signal sequence of hlyA

<400> SEQUENCE: 134

```
Ser Thr Tyr Gly Ser Gln Asp Tyr Leu Asn Pro Leu Ile Asn Glu Ile
1               5                   10                  15

Ser Lys Ile Ile Ser Ala Ala Gly Asn Leu Asp Val Lys Glu Glu Arg
            20                  25                  30

Ser Ala Ala Ser Leu Leu Gln Leu Ser Gly Asn Ala Ser Asp Phe Ser
        35                  40                  45

Tyr Gly Arg Asn Ser Ile Thr Leu Thr Ala Ser Ala
    50                  55                  60
```

<210> SEQ ID NO 135
<211> LENGTH: 395
<212> TYPE: PRT
<213> ORGANISM: Artificial Sequence
<220> FEATURE:
<223> OTHER INFORMATION: Chimeric construct

<400> SEQUENCE: 135

```
Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
```

```
            20                  25                  30
Ala Ser Ala Thr Thr Glu Ser Lys Trp Asn Ile Asn Val Arg Gln Leu
         35                  40                  45

Ile Ser Gly Glu Asn Ala Val Asp Ile Leu Ala Val Gln Glu Ala Gly
     50                  55                  60

Ser Pro Pro Ser Thr Ala Val Asp Thr Gly Thr Leu Ile Pro Ser Pro
 65                  70                  75                  80

Gly Ile Pro Val Arg Glu Leu Ile Trp Asn Leu Ser Thr Asn Ser Arg
                 85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Met Asn Ala Leu Gln Glu Asp Thr Pro Pro Gly Pro Ser Thr
        275                 280                 285

Val Phe Arg Pro Pro Thr Ser Ser Arg Pro Leu Glu Thr Pro His Cys
    290                 295                 300

Arg Glu Ile Arg Ile Gly Ile Ala Gly Ile Thr Ile Thr Leu Ser Leu
305                 310                 315                 320

Cys Gly Cys Ala Asn Ala Arg Ala Pro Thr Leu Arg Ser Ala Thr Ala
                325                 330                 335

Asp Asn Ser Glu Ser Thr Gly Phe Lys Asn Val Pro Asp Leu Arg Thr
            340                 345                 350

Asp Gln Pro Lys Pro Pro Ser Lys Lys Arg Ser Cys Asp Pro Ser Glu
        355                 360                 365

Tyr Arg Val Ser Glu Leu Lys Glu Ser Leu Ile Thr Thr Thr Pro Ser
    370                 375                 380

Arg Pro Arg Thr Ala Lys Arg Arg Ile Arg Leu
385                 390                 395

<210> SEQ ID NO 136
<211> LENGTH: 370
<212> TYPE: PRT
<213> ORGANISM: Artificial Sequence
<220> FEATURE:
<223> OTHER INFORMATION: Chimeric constuct
```

<400> SEQUENCE: 136

```
Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
    50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Ile Thr Pro His Cys Arg Glu Ile Arg Ile Gly Ile Ala Gly
        275                 280                 285

Ile Thr Ile Thr Leu Ser Leu Cys Gly Cys Ala Asn Ala Arg Ala Pro
    290                 295                 300

Thr Leu Arg Ser Ala Thr Ala Asp Asn Ser Glu Ser Thr Gly Phe Lys
305                 310                 315                 320

Asn Val Pro Asp Leu Arg Thr Asp Gln Pro Lys Pro Pro Ser Lys Lys
                325                 330                 335

Arg Ser Cys Asp Pro Ser Glu Tyr Arg Val Ser Glu Leu Lys Glu Ser
            340                 345                 350

Leu Ile Thr Thr Thr Pro Ser Arg Pro Arg Thr Ala Lys Arg Arg Ile
        355                 360                 365

Arg Leu
    370
```

<210> SEQ ID NO 137
<211> LENGTH: 288
<212> TYPE: PRT
<213> ORGANISM: Artificial Sequence
<220> FEATURE:
<223> OTHER INFORMATION: Chimeric construct

<400> SEQUENCE: 137

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly
50                  55                  60

Ser Pro Pro Ser Thr Ala Val Asp Thr Gly Thr Leu Ile Pro Ser Pro
65                  70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
        195                 200                 205

Arg Arg Ala Ser Glu Ile Ile Ser Pro Ala Ala Thr Gln Thr Ser
210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
            260                 265                 270

Gly Gly Ile Arg Ile Gly Ile Ala Gly Ile Thr Ile Thr Leu Ser Leu
        275                 280                 285

<210> SEQ ID NO 138
<211> LENGTH: 318
<212> TYPE: PRT
<213> ORGANISM: Artificial Sequence
<220> FEATURE:
<223> OTHER INFORMATION: Chimeric construct

<400> SEQUENCE: 138

Met Lys Lys Tyr Ile Ile Ser Leu Ile Val Phe Leu Ser Phe Tyr Ala
1               5                   10                  15

Gln Ala Asp Leu Thr Asp Phe Arg Val Ala Thr Trp Asn Leu Gln Gly
            20                  25                  30

Ala Ser Ala Thr Thr Glu Ser Lys Trp Asn Ile Asn Val Arg Gln Leu
        35                  40                  45

Ile Ser Gly Glu Asn Ala Val Asp Ile Leu Ala Val Gln Glu Ala Gly

```
                50                  55                  60
Ser Pro Pro Ser Thr Ala Val Asp Thr Gly Thr Leu Ile Pro Ser Pro
 65                  70                  75                  80

Gly Ile Pro Val Arg Glu Leu Ile Trp Asn Leu Ser Thr Asn Ser Arg
                     85                  90                  95

Pro Gln Gln Val Tyr Ile Tyr Phe Ser Ala Val Asp Ala Leu Gly Gly
                    100                 105                 110

Arg Val Asn Leu Ala Leu Val Ser Asn Arg Arg Ala Asp Glu Val Phe
                115                 120                 125

Val Leu Ser Pro Val Arg Gln Gly Gly Arg Pro Leu Leu Gly Ile Arg
130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
                180                 185                 190

Phe Asn Arg Glu Pro Ala Asp Leu Glu Met Asn Leu Thr Val Pro Val
                195                 200                 205

Arg Arg Ala Ser Glu Ile Ile Ser Pro Ala Ala Ala Thr Gln Thr Ser
210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg Gly Gly Gly
                260                 265                 270

Gly Gly Thr Asp Gln Pro Lys Pro Pro Ser Lys Lys Arg Ser Cys Asp
                275                 280                 285

Pro Ser Glu Tyr Arg Val Ser Glu Leu Lys Glu Ser Leu Ile Thr Thr
                290                 295                 300

Thr Pro Ser Arg Pro Arg Thr Ala Lys Arg Arg Ile Arg Leu
305                 310                 315

<210> SEQ ID NO 139
<211> LENGTH: 12
<212> TYPE: PRT
<213> ORGANISM: Artificial Sequence
<220> FEATURE:
<223> OTHER INFORMATION: Amino acid sequence which is associated with
      dimerization and inactivation

<400> SEQUENCE: 139

Phe Arg Asp Ser Arg Asp Pro Val His Gln Ala Leu
1               5                  10

<210> SEQ ID NO 140
<211> LENGTH: 12
<212> TYPE: PRT
<213> ORGANISM: Artificial Sequence
<220> FEATURE:
<223> OTHER INFORMATION: Loop from Haemophilus

<400> SEQUENCE: 140

Asn Ser Ser Ser Pro Pro Glu Arg Arg Val Tyr
1               5                  10

<210> SEQ ID NO 141
```

```
<211> LENGTH: 32
<212> TYPE: PRT
<213> ORGANISM: Artificial Sequence
<220> FEATURE:
<223> OTHER INFORMATION: Vascular targeting peptide F3

<400> SEQUENCE: 141

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Ala Pro Ala Lys Lys
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: vascular targeting peptide F3

<400> SEQUENCE: 142

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Ala Pro Ala Lys Lys
            20                  25                  30

<210> SEQ ID NO 143
<211> LENGTH: 6
<212> TYPE: PRT
<213> ORGANISM: Artificial Sequence
<220> FEATURE:
<223> OTHER INFORMATION: colE3, amino acids 451 to 456

<400> SEQUENCE: 143

Asn Lys Pro Arg Lys Gly
1               5

<210> SEQ ID NO 144
<211> LENGTH: 6
<212> TYPE: PRT
<213> ORGANISM: Artificial Sequence
<220> FEATURE:
<223> OTHER INFORMATION: colE7

<400> SEQUENCE: 144

Lys Arg Asn Lys Pro Gly
1               5

<210> SEQ ID NO 145
<211> LENGTH: 6
<212> TYPE: PRT
<213> ORGANISM: Artificial Sequence
<220> FEATURE:
<223> OTHER INFORMATION: Furin cleaveage sequence designated
      R/-/Kr/R+s/-/-/-
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 145

Arg Xaa Lys Arg Ser Xaa
1               5
```

```
<210> SEQ ID NO 146
<211> LENGTH: 6
<212> TYPE: PRT
<213> ORGANISM: Artificial Sequence
<220> FEATURE:
<223> OTHER INFORMATION: Within ColE3

<400> SEQUENCE: 146

Asn Lys Pro Arg Gly Lys
1               5

<210> SEQ ID NO 147
<211> LENGTH: 6
<212> TYPE: PRT
<213> ORGANISM: Artificial Sequence
<220> FEATURE:
<223> OTHER INFORMATION: Weak furin site

<400> SEQUENCE: 147

Asn Lys Pro Arg Lys Ser
1               5

<210> SEQ ID NO 148
<211> LENGTH: 6
<212> TYPE: PRT
<213> ORGANISM: Artificial Sequence
<220> FEATURE:
<223> OTHER INFORMATION: Strong furin site

<400> SEQUENCE: 148

Asn Arg Pro Arg Lys Ser
1               5

<210> SEQ ID NO 149
<211> LENGTH: 6
<212> TYPE: PRT
<213> ORGANISM: Artificial Sequence
<220> FEATURE:
<223> OTHER INFORMATION: Factor Xa, ia/e/Gfp/R+sti/vfs/-/g

<400> SEQUENCE: 149

Ile Glu Gly Arg Ser Val
1               5

<210> SEQ ID NO 150
<211> LENGTH: 6
<212> TYPE: PRT
<213> ORGANISM: Artificial Sequence
<220> FEATURE:
<223> OTHER INFORMATION: Furin, R/-/Kr/R+s/-/-/-
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 150

Arg Xaa Lys Arg Ser Xaa
1               5

<210> SEQ ID NO 151
<211> LENGTH: 6
<212> TYPE: PRT
<213> ORGANISM: Artificial Sequence
<220> FEATURE:
<223> OTHER INFORMATION: Plasminogen activator, -/-/-/R+R/iv/N/-
```

```
<220> FEATURE:
<221> NAME/KEY: misc_feature
<222> LOCATION: (1)..(2)
<223> OTHER INFORMATION: Xaa can be any naturally occurring amino acid

<400> SEQUENCE: 151

Xaa Xaa Arg Arg Ile Asn
1               5

<210> SEQ ID NO 152
<211> LENGTH: 6
<212> TYPE: PRT
<213> ORGANISM: Artificial Sequence
<220> FEATURE:
<223> OTHER INFORMATION: Urokinase, -/sg/Gs/Rk+-/r/-/-
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 152

Xaa Ser Gly Arg Xaa Arg
1               5

<210> SEQ ID NO 153
<211> LENGTH: 7
<212> TYPE: PRT
<213> ORGANISM: Artificial Sequence
<220> FEATURE:
<223> OTHER INFORMATION: MMP1, -/pa/-/g+li/-/-/-
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 153

Gly Pro Xaa Gly Leu Xaa Gly
1               5

<210> SEQ ID NO 154
<211> LENGTH: 7
<212> TYPE: PRT
<213> ORGANISM: Artificial Sequence
<220> FEATURE:
<223> OTHER INFORMATION: MMP8, g/Pas/-/g+l/-/g/-

<400> SEQUENCE: 154

Gly Pro Gln Gly Leu Arg Gly
1               5

<210> SEQ ID NO 155
<211> LENGTH: 7
<212> TYPE: PRT
<213> ORGANISM: Artificial Sequence
<220> FEATURE:
<223> OTHER INFORMATION: MMP 13, g/P/-/g+l/-/ga/-
<220> FEATURE:
<221> NAME/KEY: misc_feature
<222> LOCATION: (6)..(6)
<223> OTHER INFORMATION: Xaa can be any naturally occurring amino acid

<400> SEQUENCE: 155
```

```
Gly Pro Pro Gly Leu Xaa Gly
1               5

<210> SEQ ID NO 156
<211> LENGTH: 8
<212> TYPE: PRT
<213> ORGANISM: Artificial Sequence
<220> FEATURE:
<223> OTHER INFORMATION: Membrane matrix metalloprotease 1,
      -/p/-/-+1/-/-/-
<220> FEATURE:
<221> NAME/KEY: misc_feature
<222> LOCATION: (8)..(8)
<223> OTHER INFORMATION: Xaa can be any naturally occurring amino acid

<400> SEQUENCE: 156

Leu Pro Ala Gly Leu Val Leu Xaa
1               5

<210> SEQ ID NO 157
<211> LENGTH: 7
<212> TYPE: PRT
<213> ORGANISM: Artificial Sequence
<220> FEATURE:
<223> OTHER INFORMATION: PSA, si/sq/-/-/yq+s/s/-/-

<400> SEQUENCE: 157

Ser Ser Gln Tyr Ser Ser Asn
1               5

<210> SEQ ID NO 158
<211> LENGTH: 8
<212> TYPE: PRT
<213> ORGANISM: Artificial Sequence
<220> FEATURE:
<223> OTHER INFORMATION: Kallikrein 2, g/-/-/R+-/-/-/gs

<400> SEQUENCE: 158

Gly Gly Leu Arg Ser Gly Gly Gly
1               5

<210> SEQ ID NO 159
<211> LENGTH: 7
<212> TYPE: PRT
<213> ORGANISM: Artificial Sequence
<220> FEATURE:
<223> OTHER INFORMATION: Granzyme A, t/-/-/RK+sa/-/-/-
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 159

Thr Xaa Xaa Pro Arg Ser Xaa
1               5

<210> SEQ ID NO 160
<211> LENGTH: 6
<212> TYPE: PRT
<213> ORGANISM: Artificial Sequence
<220> FEATURE:
<223> OTHER INFORMATION: Granzyme B, v/-/-/D+-/-/-/-
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: misc_feature
<222> LOCATION: (6)..(6)
<223> OTHER INFORMATION: Xaa can be any naturally occurring amino acid

<400> SEQUENCE: 160

Val Glu Xaa Asp Ser Xaa
1               5

<210> SEQ ID NO 161
<211> LENGTH: 5
<212> TYPE: PRT
<213> ORGANISM: Artificial Sequence
<220> FEATURE:
<223> OTHER INFORMATION: Granzyme M, Ka/vaye/Pa/LM+-/-/-/-
<220> FEATURE:
<221> NAME/KEY: misc_feature
<222> LOCATION: (5)..(5)
<223> OTHER INFORMATION: Xaa can be any naturally occurring amino acid

<400> SEQUENCE: 161

Lys Val Pro Leu Xaa
1               5

<210> SEQ ID NO 162
<211> LENGTH: 7
<212> TYPE: PRT
<213> ORGANISM: Artificial Sequence
<220> FEATURE:
<223> OTHER INFORMATION: Cathepsin B, -/-/l/r+-/-/g/-
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 162

Xaa Leu Arg Xaa Xaa Gly Gly
1               5

<210> SEQ ID NO 163
<211> LENGTH: 7
<212> TYPE: PRT
<213> ORGANISM: Artificial Sequence
<220> FEATURE:
<223> OTHER INFORMATION: Cathepsin S, -/-/flv/r+-/-/-/-
<220> FEATURE:
<221> NAME/KEY: misc_feature
<222> LOCATION: (6)..(6)
<223> OTHER INFORMATION: Xaa can be any naturally occurring amino acid

<400> SEQUENCE: 163

Ser Gly Phe Arg Ser Xaa Gly
1               5

<210> SEQ ID NO 164
<211> LENGTH: 7
<212> TYPE: PRT
<213> ORGANISM: Artificial Sequence
<220> FEATURE:
<223> OTHER INFORMATION: Thrombin, -/-/pla/R+sag/-/-/-
<220> FEATURE:
<221> NAME/KEY: misc_feature
<222> LOCATION: (7)..(7)
<223> OTHER INFORMATION: Xaa can be any naturally occurring amino acid

<400> SEQUENCE: 164
```

Ala Gly Pro Arg Ser Leu Xaa
1               5

<210> SEQ ID NO 165
<211> LENGTH: 6
<212> TYPE: PRT
<213> ORGANISM: Artificial Sequence
<220> FEATURE:
<223> OTHER INFORMATION: Plasmin, -/-/-/KR+-/-/-/-
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 165

Ala Xaa Leu Lys Ser Xaa
1               5

<210> SEQ ID NO 166
<211> LENGTH: 6
<212> TYPE: PRT
<213> ORGANISM: Artificial Sequence
<220> FEATURE:
<223> OTHER INFORMATION: Plasminogen, -/-/-/KR+-/-/-/-
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 166

Ala Xaa Leu Lys Ser Xaa
1               5

<210> SEQ ID NO 167
<211> LENGTH: 13
<212> TYPE: PRT
<213> ORGANISM: Artificial Sequence
<220> FEATURE:
<223> OTHER INFORMATION: Targets lung vasculature - MOSE Binds membrane
      dipeptidase (MDP)

<400> SEQUENCE: 167

Cys Gly Phe Glu Cys Val Arg Gln Cys Pro Glu Arg Cys
1               5                   10

<210> SEQ ID NO 168
<211> LENGTH: 54
<212> TYPE: PRT
<213> ORGANISM: Artificial Sequence
<220> FEATURE:
<223> OTHER INFORMATION: Targets EGFR

<400> SEQUENCE: 168

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg

```
                                    50

<210> SEQ ID NO 169
<211> LENGTH: 12
<212> TYPE: PRT
<213> ORGANISM: Artificial Sequence
<220> FEATURE:
<223> OTHER INFORMATION: DUP-1 peptide, targets prostate cancer

<400> SEQUENCE: 169

Phe Arg Pro Asn Arg Ala Gln Asp Tyr Asn Thr Asn
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Lymph node homing Cys-Ala-Tyr and cell
      penetrating Arg-Leu-Arg-Arg, proceeds thorugh macripinocytosis,
      Lymphnode homing and cell penetrating

<400> SEQUENCE: 170

Cys Ala Tyr His Arg Leu Arg Arg Cys
1               5

<210> SEQ ID NO 171
<211> LENGTH: 11
<212> TYPE: PRT
<213> ORGANISM: Artificial Sequence
<220> FEATURE:
<223> OTHER INFORMATION: RGD-containing peptide

<400> SEQUENCE: 171

Ala Cys Asp Cys Arg Gly Asp Cys Phe Cys Gly
1               5                   10
```